United States Patent [19]

Foged et al.

[11] Patent Number: 5,369,019
[45] Date of Patent: Nov. 29, 1994

[54] PASTEURELLA VACCINE

[75] Inventors: Niels T. Foged, Frederiksberg; Svend Petersen, Lyngby, both of Denmark

[73] Assignee: Intervet International B.V., Boxmeer, Netherlands

[21] Appl. No.: 582,945

[22] PCT Filed: Apr. 11, 1989

[86] PCT No.: PCT/DK89/00084

§ 371 Date: Oct. 12, 1990

§ 102(e) Date: Oct. 12, 1990

[87] PCT Pub. No.: WO89/09617

PCT Pub. Date: Oct. 19, 1989

[30] Foreign Application Priority Data

Dec. 4, 1988 [DK] Denmark ............................ 1995/88

[51] Int. Cl.$^5$ .................. C07H 15/12; C12P 21/06; C12P 21/04; C12N 1/00

[52] U.S. Cl. .................. 435/69.3; 536/23.7; 536/23.4; 435/69.1; 435/71.1; 435/252.33; 435/320.1; 424/190.1; 424/255.1

[58] Field of Search .................. 424/88, 92; 435/69.1, 435/71.1, 252.3; 536/27; 530/350

[56] References Cited

U.S. PATENT DOCUMENTS

4,677,070  6/1987  Larrick et al. ........................ 435/240

FOREIGN PATENT DOCUMENTS

| | | | |
|---|---|---|---|
| 036995 | 10/1981 | European Pat. Off. | ... A61K 39/102 |
| 085469 | 8/1983 | European Pat. Off. | ... A61K 39/102 |
| 109942 | 5/1984 | European Pat. Off. | ...... A61K 39/00 |

OTHER PUBLICATIONS

Young et al PNAS 80:1194–1198 1983 Efficient Isolation of Genes Using Antibody Probes.
Foged et al Femus Microb Letter 43:45–51 1987 Characterization & Biological Effects of the Past, Mult Toxin.
Itakura et al.G350102 Science 209:1401–1405 1980.
Maniates et al Molecular Cloning A Laboratory Manual 1982.
Nakai et al Inf & Immun. 46:429–434 1984.
Nakai et al Research in Vet Science 42:232–237, 1987.
Chanter et al Journ of Microbiol. 132:1089–1097 1986 Partial Purification of an Osteolytic Toxic from P. Multocida.
Chemical Abstracts, vol. 107, (1987), Abstract No. 107:110786w, FEMS Microbiol. Lett. 1987, 43(a), 45–51 (Eng.).
Chanter et al. *J. Gen. Microbiol.*, "Partial Purification of an Osteolytic Toxin from *Pasteurella multocida*", 132: 1089–97 (1986).
Kim et al. Dialog, file Biosis, Dialog Accession No. 0017115392 (Biosis No. 83054453) Res Rep Rural Dev Adm (Suweon) 28 (Livest. and Vet), 1986, 77–93 (Kim J. Y.) "Studies on immunogenecity of Pasteurella ... ".
Nakai, et al. Reconstruction of *Pasteurella multocida* dermonecrotic toxin from three polypeptides, *FEMS Microb. Lett.*, 44: 259–265 (1987).
Dialog, file Medline, Dialog Accession No. 04970881 (NLM Accession No. 83203881) Avian Dis, Jan.–Mar. 1983, 27 (1) pp. 283–291, (Kodama H.) "Soluble fractions of *Pasteurella multocida:* ... ".
Dialog, file Medline, Dialog Accession No. 05389686 (NLM Accession No. 85005686) Infect. Immun. Oct. 1984, 46(1) pp. 48–54, (Lugtenberg B.) "Atrophic rhinitis in swine: correlation of ... ".

(List continued on next page.)

*Primary Examiner*—Christine M. Nucker
*Assistant Examiner*—H. F. Sidberry
*Attorney, Agent, or Firm*—Foley & Lardner

[57] ABSTRACT

A vaccine for immunizing animals against diseases caused by microorganisms producing an osteolytic toxin is disclosed. The vaccine contains a *Pasteurella multocida* toxin or derivative thereof that has been rendered non-toxic by genetic and/or biochemical means. The toxin or derivative is encoded by a nucleotide sequence from *Pasteurella multocida* toxin which is inserted in an expression vector capable of replicating in a suitable host microorganism in which the sequence may be expressed.

9 Claims, 31 Drawing Sheets

OTHER PUBLICATIONS

Pedersen et al. "The aetiological significance of *Bordetella bronchiseptica* and *P. multocida* in atrophic rhinitis of swine", Nord. Vet. Med. 33, pp. 513–522, (1981).

Rutter et al. "Atrophic rhinitis in piglets: Differences in the pathogenicity of *Pasteurella multocida* in combined infections . . . ", Vet. Rec. 110: pp. 531–535, (1982).

Elling et al. "The pathogenesis of persistent turbinate atrophy induced by toxigenic *Pasteurella multocida* in pigs", Vet. Pathol. 22: pp. 469–474, (1985).

Pedersen, et al. "Atrophic rhinitis in pigs: Proposal for a revised definition", Vet. Rec. 22: pp. 190–191, (1988).

Pedersen et al. "The pathogenesis of atrophic rhinitis in pigs induced by toxigenic *Pasteurella multocida*", J. Comp. Pathol. 94: pp. 203–214, (1984).

Foged et al. "Characterization and biological effect of the *P. multocida* toxin", FEMS Microbiol. Lett. 43: pp. 45–51, (1987).

Kamp et al. "Purification of a heat labile dermonecrotic toxin from culture fluid of *Pasteurella multocida*" Vet. Microbiol. 13: pp. 235–248, (1987).

Nakai et al. "Purification of dermonecrotic toxin from a sonic extract of *Pasteurella multocida* SP-72 serotype D", *Infect. Immun.*, 46: 429–434, (1984).

Trummel et al. "Stimulaton of bone resorption by a factor from *Actinomyces viscosus*", J. Perdont, Res. 14: pp. 263–264, (1979).

```
AACAAGGGAAAATAGCTAGATTAGACGATATCGATAATATCATAAATAATATTTAAAAAT
     10        20        30        40        50        60

TACGCCCCTTGACCTAGAGGGGCTTTTTTATTACATCAAAAAAATAAACCCAAACACTGC
     70        80        90       100       110       120

GAATGTTTGGGGTTTTATTTATAACCAAAATACATTAATATGTTTATTAAGTAAGCATTA
    130       140       150       160       170       180

M   K   T   K   H   F   F   N
TCTTACTTTAGGAATAAACTAACATAGAGGTTATGGATATGAAAACAAAACATTTTTTA
    190       200       210       220       230       240

S   D   F   T   V   K   G   K   S   A   D   E   I   F   R   R   L   C   T   D
ACTCAGATTTTACTGTAAAAGGAAAAAGTGCCGATGAAATTTTTAGAAGATTGTGTACTG
    250       260       270       280       290       300

H   P   D   K   Q   L   N   N   V   K   W   K   E   V   F   I   N   R   F   G
ATCATCCTGACAAGCAATTAAACAATGTAAAATGGAAAGAAGTTTTTATTAATCGTTTTG
    310       320       330       340       350       360

Q   M   M   L   D   T   P   N   P   R   K   I   V   E   K   I   I   N   E   G
GTCAGATGATGCTAGATACTCCTAATCCGAGAAAGATTGTAGAAAAAATTATTAATGAAG
    370       380       390       400       410       420
```

```
              L   E   K   Q   G   L   K   N   I   D   P   E   N   T   Y   F   N   I   F   S

GGCTTGAAAAACAAGGCCTGAAAAATATAGATCCTGAAAACACATATTTCAACATTTTTT
              430       440       450       460       470       480

S   S   D   S   S   D   G   N   V   F   H   Y   N   S   L   S   E   S   Y   R

CATCTTCTGACAGCTCCGATGGGAACGTTTTTCATTATAACTCTTTATCAGAATCCTATC
              490       500       510       520       530       540

V   T   D   A   C   L   M   N   I   F   V   E   R   Y   F   D   D   W   D   L

GAGTTACTGATGCCTGCCTAATGAATATTTTTGTGGAGCGTTATTTTGATGATTGGGACT
              550       560       570       580       590       600

L   N   S   L   A   S   N   G   I   Y   S   V   G   K   E   G   A   Y   Y   P

TGCTAAATAGCTTAGCCAGTAATGGAATATATTCAGTAGGAAAAGAAGGAGCTTATTATC
              610       620       630       640       650       660

D   H   D   Y   G   P   E   Y   N   P   V   W   G   P   N   E   Q   I   Y   H

CTGATCATGATTATGGTCCAGAATATAACCCTGTTTGGGGACCAAACGAACAAATTTACC
              670       680       690       700       710       720

S   R   V   I   A   D   I   L   Y   A   R   S   V   W   D   E   F   K   K   Y

ATTCTAGAGTGATTGCAGATATCCTTTATGCTCGCTCCGTATGGGATGAATTTAAAAAAT
              730       740       750       760       770       780

F   M   E   Y   W   Q   K   Y   A   Q   L   Y   T   E   M   L   S   D   T   F

ACTTCATGGAGTATTGGCAAAAATATGCTCAGCTTTATACCGAAATGTTATCTGATACAT
              790       800       810       820       830       840
```

TTCTTGCAATGGCTATTCAGCAATATACACGACAAACGCTTACTGATGAAGGCTTTCTTA
           850       860       870       880       890       900

V   C   N   T   Y   Y   G   N   K   E   E   V   Q   I   T   L   L   D   I   Y

TGGTTTGTAACACATATTATGGCAATAAGGAAGAAGTTCAAATAACTCTACTAGATATCT
           910       920       930       940       950       960

G   Y   P   S   T   D   I   I   C   I   E   Q   K   G   L   P   T   P   K   V

ATGGATACCCTTCCACTGATATAATTTGTATAGAGCAAAAAGGGCTTCCTACTCCTAAAG
           970       980       990      1000      1010      1020

I   L   Y   I   P   G   G   T   Q   P   F   V   E   F   L   N   T   D   D   L

TGATACTTTACATTCCTGGAGGAACACAACCATTTGTTGAATTTCTTAATACAGATGATC
          1030      1040      1050      1060      1070      1080

K   Q   W   I   A   W   H   L   K   D   N   K   H   M   V   R   F   R   K   H

TGAAACAATGGATTGCATGGCATTTAAAAGATAACAAACATATGGTCCGATTCCGCAAAC
          1090      1100      1110      .1120     1130      1140

F   S   L   K   Q   R   Q   E   G   E   T   F   T   G   I   D   K   A   L   Q

ATTTCTCGCTAAAACAACGTCAGGAAGGAGAAACGTTTACAGGTATAGATAAAGCACTTC
          1150      1160      1170      1180      1190      1200

Y   I   A   E   E   S   P   E   W   P   A   N   K   Y   I   L   Y   N   P   T

AATATATTGCAGAAGAGTCCCCTGAATGGCCTGCCAATAAATACATCCTTTATAATCCGA
          1210      1220      1230      1240      1250      1260
```

CACATTTAGAAACAGAAAATTTATTTAACATCATGATGAAGCGAACAGAACAGCGGATGC
     1270        1280        1290        1300        1310        1320

E   D   S   D   V   Q   I   R   S   N   S   E   A   T   R   D   Y   A   L   S

TTGAAGATAGTGATGTACAGATTAGATCAAATTCAGAAGCTACCCGTGACTATGCTCTTT
     1330        1340        1350        1360        1370        1380

L   L   E   T   F   I   S   Q   L   S   A   I   D   M   L   V   P   A   V   G

CATTACTCGAAACCTTTATTTCACAGTTATCTGCAATAGATATGTTAGTACCAGCAGTAG
     1390        1400        1410        1420        1430        1440

I   P   I   N   F   A   L   S   A   T   A   L   G   L   S   S   D   I   V   V

GTATCCCAATTAATTTTGCCCTATCAGCTACAGCATTAGGACTTAGCTCGGATATTGTAG
     1450        1460        1470        1480        1490        1500

N   G   D   S   Y   E   K   R   K   Y   G   I   G   S   L   V   Q   S   A   L

TTAATGGAGATTCATATGAAAAGAGAAAATATGGAATTGGGTCCTTAGTGCAATCTGCAT
     1510        1520        1530        1540        1550        1560

F   T   G   I   N   L   I   P   V   I   S   E   T   A   E   I   L   S   S   F

TATTCACAGGAATTAATCTTATTCCAGTTATTTCGGAAACCGCAGAAATTTTATCTTCTT
     1570        1580        1590        1600        1610        1620

S   R   T   E   E   D   I   P   A   F   F   T   E   E   Q   A   L   A   Q   R

TCTCTAGAACAGAAGAAGATATTCCAGCTTTTTTCACTGAAGAACAAGCTTTAGCTCAAC
     1630        1640        1650        1660        1670        1680

GCTTTGAAATAGTAGAAGAAGAATTACATTCTATCTCACCTGATGATCCTCCTCGAGAAA
      1690        1700        1710        1720        1730        1740

TTACTGACGAAAATTTACATAAAATTCGTCTGGTACGTCTTAACAATGAAAATCAACCTT
      1750        1760        1770        1780        1790        1800

V   V   L   R   R   L   G   G   N   K   F   I   R   I   E   P   I   T   F   Q

TAGTTGTGTTACGAAGATTAGGAGGAAATAAATTTATCAGAATCGAGCCTATAACATTCC
      1810        1820        1830        1840        1850        1860

E   I   K   G   S   L   V   S   E   V   I   N   P   V   T   N   K   T   Y   Y

AGGAAATAAAAGGTTCTTTAGTAAGTGAAGTTATAAATCCAGTGACTAATAAAACGTACT
      1870        1880        1890        1900        1910        1920

V   S   N   A   K   L   L   G   G   S   P   Y   S   P   F   R   I   G   L   E

ACGTAAGCAATGCTAAACTATTAGGGGGCTCTCCTTATAGTCCTTTCCGTATTGGATTAG
      1930        1940        1950        1960        1970        1980

G   V   W   T   P   E   V   L   K   A   R   A   S   V   I   G   K   P   I   G

AAGGTGTTTGGACACCAGAGGTATTAAAAGCAAGAGCTTCCGTTATTGGAAAGCCTATTG
      1990        2000        2010        2020        2030        2040

E   S   Y   K   R   I   L   A   K   L   Q   R   I   H   N   S   N   I   L   D

GAGAATCATATAAAAGAATATTAGCCAAACTACAAAGAATACATAACAGTAATATCTTAG
      2050        2060        2070        2080        2090        2100

```
ATGAGCGACAAGGTTTAATGCATGAACTCATGGAGCTTATTGATCTTTATGAAGAATCGC
        2110      2120      2130      2140      2150      2160
```

```
   P  S  S  E  R  L  N  A  F  R  E  L  R  T  Q  L  E  K  A  L
```

```
AACCTTCTTCAGAGCGTTTGAATGCTTTTCGTGAACTGCGTACTCAATTAGAAAAAGCGC
        2170      2180      2190      2200      2210      2220
```

```
   Y  L  P  E  M  E  A  L  K  K  Q  I  L  Q  I  P  N  K  G  S
```

```
TTTATCTTCCTGAAATGGAAGCATTAAAAAAACAAATACTACAGATTCCTAACAAAGGTT
        2230      2240      2250      2260      2270      2280
```

```
   G  A  A  R  F  L  L  R  T  A  M  N  E  M  A  G  K  T  S  E
```

```
CTGGTGCCGCTCGATTTTTACTTCGTACAGCCATGAATGAAATGGCTGGAAAAACCAGTG
        2290      2300      2310      2320      2330      2340
```

```
   S  T  A  D  L  I  R  F  A  L  Q  D  T  V  I  S  A  P  F  R
```

```
AAAGCACGGCTGATTTAATACGCTTTGCCTTGCAAGATACAGTAATTTCAGCGCCTTTTC
        2350      2360      2370      2380      2390      2400
```

```
   G  Y  A  G  A  I  P  E  A  I  D  F  P  V  K  Y  V  I  E  D
```

```
GCGGATATGCTGGTGCGATTCCAGAGGCAATAGACTTTCCTGTAAAATATGTAATAGAAG
        2410      2420      2430      2440      2450      2460
```

```
   I  S  V  F  D  K  I  Q  T  N  Y  W  E  L  P  A  Y  E  S  W
```

```
ACATATCTGTATTTGATAAAATACAGACAAATTACTGGGAACTTCCTGCTTATGAAAGCT
        2470      2480      2490      2500      2510      2520
```

```
   N  E  G  S  N  S  R  L  L  P  G  L  L  R  E  S  Q  S  K  G
```

```
GGAACGAAGGAAGTAATAGCCGATTACTGCCTGGTTTGTTACGTGAATCGCAAAGCAAGG
```

GGATGTTAAGTAAGTGTCGTATCATAGAAAATAGCCTTTATATTGGACATAGCTATGAAG
               2590       2600       2610       2620       2630       2640

M  F  Y  S  I  S  P  Y  S  N  Q  V  G  G  P  Y  E  L  Y  P

AAATGTTTTACAGCATTTCTCCATATTCAAACCAGGTTGGAGGGCCTTATGAATTATATC
               2650       2660       2670       2680       2690       2700

F  T  F  F  S  M  L  Q  E  V  Q  G  D  L  G  F  E  Q  A  F

CTTTCACTTTTTTCAGTATGCTTCAAGAAGTACAAGGTGATTTAGGATTTGAGCAGGCCT
               2710       2720       2730       2740       2750       2760

A  T  R  N  F  F  N  T  L  V  S  D  R  L  S  L  M  E  N  T

TTGCCACACGTAACTTTTTCAATACTCTTGTTTCTGATCGACTATCCTTAATGGAAAATA
               2770       2780       2790       2800       2810       2820

M  L  L  T  E  S  F  D  Y  T  P  W  D  A  I  Y  G  D  I  N

CGATGTTACTTACAGAAAGTTTTGATTATACACCTTGGGATGCTATTTATGGAGATATTA
               2830       2840       2850       2860       2870       2880

Y  D  E  Q  F  A  A  M  S  I  N  E  R  I  E  K  C  M  N  T

ATTATGATGAACAATTTGCTGCAATGTCTATTAATGAACGCATAGAAAAATGTATGAATA
               2890       2900       2910       2920       2930       2940

Y  R  G  V  A  F  Q  N  S  S  K  S  I  D  F  F  L  N  N  L

CCTATAGAGGTGTGGCATTCCAAAACTCTTCAAAAAGTATTGACTTTTTCCTAAATAATC
               2950       2960       2970       2980       2990       3000
```

TAACCACATTCATTGATAATGGACTAACCGAAATTGCTATATCTGATTTACCGTATGATA
    3010        3020        3030        3040        3050        3060

V   Q   Q   E   I   S   Q   F   L   Q   G   S   N   E   W   K   T   L   D   A

TTGTGCAACAAGAAATCTCTCAATTCTTACAAGGAAGTAATGAATGGAAAACACTTGATG
    3070        3080        3090        3100        3110        3120

M   L   F   N   L   D   K   G   D   I   N   G   A   F   R   K   L   L   Q   S

CCATGTTATTTAACTTAGATAAAGGAGATATTAATGGTGCTTTCAGAAAGCTTCTGCAAT
    3130        3140        3150        3160        3170        3180

A   K   D   N   N   I   K   F   R   A   I   G   H   S   D   N   S   V   P   P

CAGCAAAAGATAATAATATAAAATTTAGAGCTATAGGGCATTCAGATAATTCTGTTCCGC
    3190        3200        3210        3220        3230        3240

F   N   N   P   Y   K   S   L   Y   Y   K   G   N   I   I   A   E   A   I   E

CATTTAATAACCCTTATAAGTCTTTATATTATAAAGGAAATATAATAGCTGAAGCAATTG
    3250        3260        3270        3280        3290        3300

K   L   D   R   E   G   Q   K   F   V   V   F   A   D   S   S   L   L   N   S

AAAAACTAGATCGAGAAGGTCAAAAATTTGTTGTATTTGCTGATAGTTCTCTGCTCAACA
    3310        3320        3330        3340        3350        3360

T   P   G   T   G   R   P   M   P   G   L   V   Q   Y   L   K   I   P   A   T

GCACGCCTGGGACAGGTCGTCCTATGCCAGGACTAGTTCAATATTTAAAAATACCAGCAA
    3370        3380        3390        3400        3410        3420
```

CTGTAGTAGATAGCGATGGTGCATGGCAATTTCTTCCAGATGTAGCTTCAAGCAGAGTTC
     3430      3440      3450      3460      3470      3480

I   E   V   T   E   L   E   N   W   Q   V   L   T   P   P   Q   G   K   I   L

CTATTGAAGTTACAGAGTTAGAAAATTGGCAAGTCTTAACTCCTCCACAAGGTAAGATTC
     3490      3500      3510      3520      3530      3540

G   L   K   Q   F   K   L   T   A   G   F   P   T   E   Q   S   R   L   P   L

TTGGATTAAAGCAATTTAAGTTAACGGCAGGTTTTCCAACAGAACAAAGTCGCTTACCTC
     3550      3560      3570      3580      3590      3600

L   E   N   S   V   S   E   D   L   R   E   E   L   M   Q   K   I   D   A   I

TTTTAGAGAATTCGGTTTCTGAAGATTTAAGGGAAGAATTAATGCAAAAGATTGATGCAA
     3610      3620      3630      3640      3650      3660

K   N   D   V   K   M   N   S   L   V   C   M   E   A   G   S   C   D   S   V

TAAAAAATGATGTGAAAATGAATAGTTTAGTGTGTATGGAAGCTGGCTCTTGTGATTCAG
     3670      3680      3690      3700      3710      3720

S   P   K   V   A   A   R   L   K   D   M   G   L   E   A   G   M   G   A   S

TAAGCCCTAAGGTAGCTGCCCGTCTTAAAGATATGGGGTTAGAAGCTGGGATGGGTGCTT
     3730      3740      3750      3760      3770      3780

I   T   W   R   R   E   G   G   M   E   F   S   H   Q   M   H   T   T   A

CTATTACCTGGTGGAGACGTGAAGGCGGGATGGAATTTTCACATCAGATGCATACTACTG
     3790      3800      3810      3820      3830      3840
```

CTTCCTTTAAATTTGCTGGTAAAGAGTTTGCCGTGGATGCTTCACATTTACAATTTGTAC
    3850        3860        3870        3880        3890        3900

D   Q   L   D   T   T   I   L   I   L   P   V   D   D   W   A   L   E   I   A

ACGACCAATTAGATACAACTATCCTGATACTACCTGTAGATGATTGGGCTTTAGAAATAG
    3910        3920        3930        3940        3950        3960

Q   R   N   R   A   I   N   P   F   V   E   Y   V   S   K   T   G   N   M   L

CTCAAAGAAATCGGGCTATTAATCCTTTTGTGGAATATGTTAGTAAAACAGGAAACATGT
    3970        3980        3990        4000        4010        4020

A   L   F   M   P   P   L   F   T   K   P   R   L   T   R   A   L

TAGCACTCTTCATGCCTCCTCTTTTCACAAAGCCTCGCTTAACAAGAGCACTATAACTAA
    4030        4040        4050        4060        4070        4080

TTAAAAACTGTATTAAAGCCTTATATTATAAGGCTTTAATTTTCTTTCAAGAATTATTAA
    4090        4100        4110        4120        4130        4140

GTAGAAGAATCAAAATCAATGAGATAGATAAAATCAAATGTTATTACCAATACAACTTTC
    4150        4160        4170        4180        4190        4200

TTAAGTATACTTTTTGAATTTTTTGCGTTAATAAATTTATAATACCCTTAACTCAATAAA
    4210        4220        4230        4240        4250        4260

AGAAGTTATTGAGAAGTTTAAATCTTGTGAGCAAGATGAAGATATAATTTCAGCAATCGA
    4270        4280        4290        4300        4310        4320

TCTTATTAGCGCTTCATATAGAAGGGCTGTGGATGCAGTGGAACAAAGATTCGGTTCTAG
    4330        4340        4350        4360        4370        4380
```

FIG. 10j

PASTEURELLA VACCINE

FIELD OF INVENTION

The present invention relates to a vaccine for immunizing animals against diseases caused by microorganisms producing an osteolytic toxin, a DNA sequence encoding a *Pasteurella multocida* toxin useful for producing the toxin and as a diagnostic agent, methods of producing and isolating a *P. multocida* toxin, use of a *P. multocida* toxin, a monoclonal antibody directed against a *P. multocida* toxin, a diagnostic agent comprising said monoclonal antibody and the use of said monoclonal antibody for a variety of diagnostic and other purposes.

TECHNICAL BACKGROUND

Atrophic rhinitis is a disease which profoundly affects the bone structure of the porcine snout. The etiological agent which is currently considered to be the cause of growth retarding progressive atrophic rhinitis is toxigenic (toxin-producing) strains of *P. multocida* which colonize the nasal cavity of pigs (Pedersen and Barfod, 1981, (ref. 1), Rutter and Rojas, 1982, (ref. 2), Elling and Pedersen, 1985, (ref. 3), Pedersen et al. 1988 (ref. 4). It has been that the nasal mucosa are more easily colonized by *P. multocida* when the resistance to infection is lower such as when the pigs are concomitantly infected with *Bordetella bronchiseptica* or when the nasal mucosa are exposed to a mild chemical irritant (cf. Pedersen and Elling, 1984, (ref. 5).

The pathological effects of *P. multocida* infection may be ascribed to a toxin produced by this bacterium. The toxin which has an apparent molecular weight of 143 kd and an actual molecular weight of 146.5 kd induces bone resorption (osteolysis) of the nasal turbinates and other bone structures in the nasal cavity by stimulating osteoclast activity in porcine turbinate bones, and causes impaired osteoblastic bone formation.

The disease is of major economic importance to pig breeders all over the world, since apart from the pathological effects on the nasal (and occasionally facial) bones noted above, it causes a slower growth rate of the infected pigs and consequently higher production costs. Attempts have therefore been made to reduce the occurrence and the significance of *P. multocida* infection, for instance by the establishment of SPF (specific pathogen free) pigs via cesarean section, or by antibiotic treatment of infected animals or prophylactic vaccination.

Known vaccines for the immunization of animals, principally pigs, against diseases ascribable to *P. multocida* infection, especially atrophic rhinitis, comprise killed *P. multocida* cells optionally combined with killed *Bordetella bronchiseptica* cells (cf. EP 85 469) and/or an inactivated (usually by heat treatment or addition of formaldehyde) toxin-containing extract of toxigenic *P. multocida*. Vaccines of the latter type are commercially available from Northern Drugs & Chemicals Ltd., Copenhagen, Denmark, under the trademark Atrinord ®, as well as from Intervet International BV, Boxmoor, Holland, under the trademark Nobi-vacART ®.

The present inventors contemplate that an improved immunogenic effect relative to the known vaccine preparations may be obtained by using a purified and suitably modified toxin preparation for vaccination purposes either to replace the conventional vaccines or as a constituent thereof.

The purification of *P. multocida* toxin has previously been described. Thus, Foged et al., 1987, (ref. 6) disclose the purification of the toxin by chromatography and polyacrylamide gel electrophoresis. The purified toxin is used solely for studying its toxic and pathological effects. Kamp et al., 1987, (ref. 7) also disclose the purification of the *P. multocida* toxin for the purpose of clinical studies. They suggest that the purified toxin may be used as an antigen to raise specific antibodies useful for serological tests. Nakai et al., 1984, (ref. 8) disclose a method of purifying the *P. multocida* toxin by chromatography and polyacrylamide gel electrophoresis. They further disclose the production of polyclonal antibodies directed against the purified toxin which they use to analyse the purity of the purified toxin. It is suggested that the antibodies may be used to further study the role of the toxin in atrophic rhinitis.

None of these publications suggest the use of a purified toxin as a component of a vaccine for immunizing animals against Pasteurella infection, and this is believed to be a novel concept.

SUMMARY OF THE INVENTION

Accordingly, in one aspect the present invention relates to a vaccine for immunizing an animal, including a human being, against diseases caused by microorganisms producing an osteolytic toxin, the vaccine comprising an immunogenically effective amount of a recombinant, immunogenic, detoxified *P. multocida* toxin or toxin analogue together with an immunologically acceptable carrier or vehicle.

For the preparation of the known vaccines, a toxigenic Pasteurella strain is cultivated and the toxin is isolated from the culture medium or from a bacterial extract followed by detoxification by, for instance, thermal or chemical treatment. Compared to this procedure, the production of the toxin or toxin analogue by recombinant DNA techniques has a number of advantages: it is possible to produce the toxin or toxin analogue by growing a non-pathogenic organism, the toxin or toxin analogue may be produced in higher quantities than those produced by wild-type *P. multocida* strains, for instance by using a strong promoter to induce a high level of expression of the toxin gent or by using a high copy number vector for cloning the toxin gent, and it is possible to produce the toxin or toxin analogue in a detoxified form, e.g. by subjecting file gent encoding the toxin to treatment with a mutagen, or by deleting a part of the nucleotide sequence coding for the toxin or toxin analogue, substituting one or more nucleotides in the sequence, etc. The recombinant toxin or toxin analogue may be used in substantially pure form in the vaccine of the invention but may also be employed as a crude or partially purified preparation.

In the present context, the term "substantially pure" is understood to mean that the vaccine is substantially free from other immunogenically active components the presence of which might give rise to adverse immune reactions in the animals immunized with the vaccine and, most importantly, that no other components of the microorganisms producing the toxin or toxin analogue, such as cell debris or cellular proteins apart from the toxin or toxin analogue itself or a protein or polypeptide to which the toxin or toxin analogue is fused (vide below) are present in the vaccine preparation. A high purity of the detoxified toxin or toxin analogue is believed to result in a high antitoxin response on immunization with the vaccine of the invention and a lower dosage of the toxin or toxin analogue may consequently be required for immunization purposes than that used in crude or partially purified vaccine preparations. A substantially pure toxin or toxin analogue has the added advantage that the exact concentration thereof in a given vaccine preparation is known so that an exact dosage may be administered to the animal in question.

The microorganism producing an osteolytic toxin (i.e. a toxin directly or indirectly involved in bone resorption) against which the vaccine confers immunity is preferably P. multocida. Other microorganisms which have shown osteolytic effects or regulation of specific markers of bone metabolism are e.g. Actinomyes viscosus and Bordetella pertussis (Trummel et al., 1979, (ref. 9) and Price (ref. 10).

Due to the toxic activity of the P. multocida toxin, it is not possible to use the native toxin in a vaccine of the invention. Rather, it must be present in detoxified form. The term "detoxified" should be understood to mean that the toxic activity has been removed from at least a sufficient number, but not necessarily all, of the toxin molecules present in the vaccine preparation so that the vaccine, when administered to an animal to be immunized, will not produce any adverse toxic effects in the animal in question, while still giving rise to a satisfactory immune response.

The detoxification of the P. multocida toxin or toxin analogue may be carried out in a variety of ways. Thus, it is possible to subject the toxin or toxin analogue to thermal treatment, the toxin being known to be heat labile and to be inactivated (i.e. detoxified) at 70° C. Furthermore, the toxin or toxin analogue may be subjected to treatment with a chemical, such as formaldehyde, glutaraldehyde or a suitable proteolytic enzyme, e.g. trypsin. Detoxification may also be brought about by mutagenizing the gone coding for the P. multrocida toxin or toxin analogue by means of, for instance, ultra-violet radiation, ionizing radiation or a chemical mutagen such as mitomycin C, 5-bromouracil, methylmethane sulphonate, nitrogen mustard or a nitofuran. Furthermore, the toxin may be detoxified by substitution, deletion, addition or insertion of one or more amino acids in the toxin or toxin analogue, or by substitution, addition, deletion or insertion of one or more base pairs in the nucleotide sequence coding for the toxin or toxin analogue, or a combination of these measures.

In contrast to detoxification by thermal or chemical treatment, the genetic procedure as the obvious advantage of resulting in a uniform population of equally detoxified molecules.

It should be noted that the terms "substitution, deletion, addition or insertion" should be interpreted with reference to the full-length toxin protein. Thus, "substitution" is intended to mean the replacement of any one or more amino acids or nucleotides in the full amino acid or nucleotide sequence with one or more others, "addition" is understood to mean the addition of one or more amino acids or nucleotides at either end of the full amino acid or nucleotide sequence, "insertion" is intended to mean the introduction of one or more amino acids or nucleotides within the full amino acid or nucleotide sequence, and "deletion" is intended to indicate that one or more amino acids or nucleotides have been deleted from the full amino acid or nucleotide sequence whether at either end of the sequence or at any suitable point within it. It should be understood that the detoxification of the toxin or toxin analogue may also be brought about by a combination of two or more of these procedures.

The term "toxin analogue" is used in the present context to indicate a protein or polypeptide of a similar amino acid composition or sequence as the P. multocida toxin allowing for variations which do not have an adverse effect on the immunogenicity of the analogue. The analogous polypeptide or protein may be derived from a microorganism of another species than P. multocida or may be partially or completely of synthetic origin. The analogous polypeptide or protein may also be one which comprises at least one epitope reactive with anti-P. multocida toxin antibodies found in samples from individuals with atrophic rhinitis and/or which elicits antibodies reactive with native P. multocida toxin. The term is further intended to mean any immunogenic subsequence, functional equivalent or derivative of the toxin.

The term "immunogenic subsequence" is intended to indicate a sequence of the full-length toxin which from the outset is produced in a truncated form relative to the full-length toxin protein or which subsequent to production of the full-length protein is generated, for instance by proteolytic cleavage thereof or by expression of a nucleotide sequence shorter than the full nucleotide sequence encoding P. multocida toxin. The minimum subsequence is one which at least comprises a relevant epitope of the toxin, i.e. an epitope which gives rise to a relevant immune response in an animal immunized with the vaccine of the invention.

The term "functional equivalent" is intended to include all immunogenically active substances with the ability to evoke an immune response in animals to which a vaccine containing the equivalent has been administered which is similar to the immune response evoked by the detoxified P. multocida toxin, in that it is able to confer immunity to diseases caused by microorganisms producing an osteolytic toxin. The functional equivalent may be derived from a microorganism of another species than P. multocida or may partially or completely be of synthetic origin. It should be understood that the similarities between the P. multocida toxin and the functional equivalent are qualitative rather than quantitative, relating to the nature rather than the level of activity of the functional equivalent.

The term "derivative" is understood to mean a modification of the toxin such as one produced by substitution, insertion, addition or deletion of one or more amino acids or nucleotides or a combination of these measures, as defined above, or by fusion with another polypeptide.

In a further aspect, the present invention relates to a DNA fragment comprising a nucleotide sequence coding for a P. multocida toxin or toxin analogue, as defined above. The DNA fragment may for instance be used in a method of preparing the toxin or toxin analogue by recombinant DNA techniques or as a diagnostic agent (i.e. a DNA probe).

In a still further aspect, the present invention relates to a monoclonal antibody which is directed against or reactive with a P. multocida toxin or a toxin analogue as defined above, or a fragment of said antibody. It should be noted that the antibody may be reactive with both the toxic and detoxified toxin, thus making it useful for a variety of diagnostic, immunization and isolation purposes as will be described in further detail below.

DETAILED DISCLOSURE OF THE INVENTION

The toxin produced by *P. multocida* (in the following occasionally abbreviated to PMT) which, as noted above, is generally believed to be the causative agent of porcine atrophic rhinitis, has in the prior literature been variously termed "dermonecrotic toxin", "osteolytic toxin", "turbinate atrophy toxin" and "heat labile exotoxin", but it would appear to be the same toxin as the amino acid composition, isoelectric point and biological activities of the variously termed toxins show basic similarities, although minor variations in the properties of toxins isolated from different strains of *P. multocida* appear to exist. The estimated amino acid composition of PMT (as deduced from the DNA sequence) is as follows:

Ala is found 76 times - 5.91%
Cys is found 8 times - 0.62%
Asp is found 71 times - 5.53%
Glu is found 100 times - 7.78%
Phe is found 69 times - 5.37%
Gly is found 71 times - 5.53%
His is found 19 times - 1.48%
Ile is found 92 times - 7.16%
Lys is found 70 times - 5.45%
Led is found 127 times - 9.88%
Met is found 36 times - 2.80%
Asn is found 73 times - 5.68%
Pro is found 62 times - 4.82%
Gln is found 56 times - 4.36%
Arg is found 58 times - 4.51%
Ser is found 97 times - 7.55%
Thr is found 66 times - 5.14%
Val is found 63 times - 4.90%
Trp is found 18 times - 1.40%
Tyr is found 53 times - 4.12%

The total number of amino acid residues is 1285, and the full-length toxin has a molecular weight of 146.5 kd.

The recombinant toxin or toxin analogue used in the vaccine of the invention may more specifically be one encoded by a DNA sequence substantially as shown in FIG. 10 (a)-(j) (SEQ. ID. NO. 1) or a subsequence thereof coding an immunogenic subsequence of the toxin or toxin analogue. It should be noted that the amino acid sequence (SEQ. ID. NO. 2) deduced from the DNA sequence is also shown in FIG. 10 (a)-(j) above the DNA sequence. A suitable analogue may be one which has a DNA sequence which differs from that of the native toxin by one or more base pairs and which may be derived by substituting one or more nucleotides in the toxin DNA sequence either giving rise to the same amino acid sequence, but where the nucleotide substitutions make the sequence conform to the codon usage of the microorganism in which the sequence is inserted. or giving rise to a somewhat different amino acid sequence which, however, is functionally similar to that of the native toxin.

Apart from the toxin or toxin analogue as defined above, the vaccine of the invention also comprises an immunologically acceptable carrier or vehicle. This vehicle may be any vehicle usually employed in the preparation of vaccines, e.g. a diluent such as isotonic saline, suspending agent etc. The vaccine may be prepared by mixing an immunogenically effective amount of the toxin or toxin analogue with the vehicle in an amount resulting in the desired concentration of the toxin or toxin analogue in the vaccine preparation. Although the amount of toxin or toxin analogue per unit dose of the vaccine will differ according to the age of the animals to be immunized (for instance according to whether sows or piglets are to be immunized against *P. multocida*), the route and form of administration, and the immunogenicity of the particular toxin present in the vaccine, a suitable amount of toxin or toxin analogue is contemplated in range of 0.1–500 µg per dosage of the vaccine.

The vaccine may further comprise an adjuvant in order to increase the immunogenicity of the vaccine preparation. The adjuvant may be selected from Freund's complete or incomplete adjuvant, aluminium hydroxide, *Bordetella pertussis*, a saponin, a muramyl dipeptide, an iscom (immune stimulating complex: cf. for instance EP 109 942) and an oil, such as a vegetable oil, e.g. peanut oil, or a mineral oil, e.g. silicone oil.

In some cases it may be advantageous to couple the toxin or toxin analogue to a carrier, in particular a macromolecular carrier. The carrier is usually a polymer to which the toxin is bound by hydrophobic non-covalent inneraction, such as a plastic, e.g. polystyrene, or a polymer to which the toxin is covalently bound, such as a polysaccharide, or a polypeptide, e.g. bovine serum albumin, ovalbumin or keyhole limpet hemocyanin. The carrier should preferably be non-toxic and non-allergenic. The toxin or toxin analogue may be multivalently coupled to the macromolecular carrier as this provides an increased immunogenicity of the vaccine preparation. It is also contemplated that the toxin or toxin analogue may be presented in multivalent form by polymerizing the toxin or toxin analogue with itself.

In a particular embodiment of the vaccine of the present invention, the toxin or toxin analogue as defined above is fused to another polypeptide. Techniques for preparing fused polypeptides are known from, e.g. Casadaban and Cohen, 1983, (ref. 11). Alternatively, the fusion may be provided by fusing the nucleotide sequence encoding the toxin to a nucleotide sequence encoding another polypeptide so that the fused nucleotide sequence, when inserted in an appropriate vector, is expressed as a fusion polypeptide on transformation of the vector to a suitable microorganism and growth of the microorganism under conditions favorable to the expression of the fused sequence. The polypeptide to which the toxin is fused may, for instance, be a carrier polypeptide as suggested above, lysozyme or another immunogenic peptide such as a Ty protein from *Saccharomyces cerevisiae*, protein A from *Scaphylococcus aureus*, Hepatitis B core antigen, etc.

It is also contemplated that the vaccine may be in the form of tablet, granule or capsule intended for oral administration since there is some evidence that immunogens may be absorbed through the intestinal wall and stimulate B-lymphocytes which then migrate to local epithelial regions where they transform into immunoglobulin-secreting plasma cells. An oral vaccine should be provided with an enteric coating in order to protect the toxin or toxin analogue from substances present in gastric juice which might be deleterious to the toxin or toxin analogue, such as pepsin. The enteric coating may be selected from shellac, cellulose acetate esters such as cellulose acetate phthalate, hydroxypropylmethyl cellulose esters such as hydroxypropylmethyl cellulose phythalate, polyvinyl acetate esters such as polyvinyl acetate phthalate, and polymers of methacrylic acid and (meth)acrylic acid esters. Newly developed methods of encapsulations. based on microspheres with a diameter of about 5–15 µm are of special interest since such particles containing an immunogenic substance after administration will be selectively delivered to Peyers's patches thereby providing immunity on mucosal surfaces. Stimulation of the immune response on respiratory mucosal surfaces may also be obtained through intranasal immunizations. (Mestecky, 1987, (ref. 12).

The DNA fragment of the invention comprising the nucleotide sequence encoding the toxin or toxin analogue may be derived from complementary cDNA obtained by preparing a cDNA library on the basis of mRNA from a toxin-producing P. multocida strain by standard methods. Alternatively and preferably, the nucleotide sequence may be derived from a P. multocida genome, by screening for genomic sequences hybridizing to a DNA probe prepared on the basis of the full or partial amino acid sequence of the toxin in accordance with established procedures or by establishing a toxin gene library and screening for toxin-producing clones by means of a toxin-specific antibody (for a more detailed description of this procedure, see Example 4). In the case of PMT, it is not possible to prepare a DNA probe on the basis of its N-terminal amino acid sequence since PMT is blocked in the N-terminal and therefore is not degraded by procedures for the sequencing of amino acids.

Another routine screening method which has proven to be difficult in the case of PMT is screening for toxin-producing clones by means of an anti-PMT serum. When using serum from a rabbit repeatedly immunized with PMT, the present inventors found 5 E.coli clones by the Colony bloc method in the gene library described in Example 5. Further studies of the above 5 clones, however, showed that none of them were producing PMT. These results indicate the importance of performing the screening with anti-PMT monoclonal antibodies as described in Example 5.

The nucleotide sequence may also be derived from a bacteriophage infectious for P. multocida, i.e. one which has been transferred from one bacterial strain which originally carried the sequence to another strain which did not originally carry the sequence by bacteriophage transfection. Similarly, the nucleotide sequence may be derived from a plasmid or other genetic element transferred from one strain to another by conjugation, transformation or the like.

Furthermore, the nucleotide sequence coding for the toxin may be a synthetic sequence, that is, one prepared according to standard procedures, e.g. as described in Matches et al., 1984, (ref. 13). Finally, the nucleotide sequence may be a mixed genomic and synthetic or mixed cDNA and synthetic sequence prepared by ligating DNA fragments of genomic, cDNA or synthetic origin (as appropriate) which DNA fragments each contain part of the nucleotide sequence encoding the toxin, in accordance with established methods.

In accordance with the explanation given above, the DNA fragment may be one which has been modified by substitution, addition, insertion or deletion of one or more nucleotides in the sequence with the purpose of establishing a sequence which, when expressed, results in the production of a detoxified toxin or toxin analogue.

In particular, the invention relates to a DNA fragment which comprises a nucleotide sequence substantially as shown in FIG. 10 (a)-(j) (SEQ. ID. NO. 1) or a modification thereof as indicated above. The sequence coding for the full-length toxin starts at position 219 (or 213) of the sequence shown in the figure, while the end of the sequence is at position 4073. The DNA sequence shown in FIG. 10 (a)-(j) (SEQ. ID. NO. 1) has been established by well-known methods as described in Example 7 below.

The DNA fragment of the invention may further comprise a nucleotide sequence encoding another polypeptide fused to the nucleotide sequence encoding the toxin or toxin analogue with the purpose of producing a fused polypeptide, as explained above. A further purpose of preparing a fused polypeptide may be to facilitate purification of the toxin. In this case, the fused sequence may be inserted into an appropriate vector which is transformed to a suitable host microorganism which is grown under conditions ensuring expression of the fused sequence after which the fused polypeptide is recovered from the culture by subjecting the fused polypeptide to affinity chromatography involving an antibody or any other ligand reacting with the second polypeptide. After purification, the second polypeptide may then be removed, for instance by suitable proteolytic cleavage followed by separation of the two polypeptides.

In a further aspect, the invention relates to an expression vector which is capable of replicating in a host microorganism and which carries a DNA fragment as described above. The vector may either be one which is capable of autonomous replication, such as a plasmid, or one which is replicated with the host chromosome, such as a bacteriophage. Specific examples of expression vectors of the invention are the plasmids pSPE A-R described in Example 9 below and shown in the appended FIG.13.

In a still further aspect, the invention relates to a microorganism which is capable of expressing a DNA fragment as defined above and which carries a vector as described above. The microorganism is preferably a bacterium, especially a gramnegative bacterium such as E. coli.

The invention also relates to a method of producing an immunogenic detoxified P. multocida toxin or toxin analogue, the method comprising a) isolating a nucleotide sequence coding for the P. multocida toxin or toxin analogue, b) inserting said sequence, optionally in suitably modified form resulting in the expression of the detoxified toxin or toxin analogue or a subsequence coding for an immunogenic subsequence of the toxin to toxin analogue, in an expression vector, c) transforming a suitable host microorganism with the vector produced in step b), d) cultivating the microorganism produced in step c) under suitable conditions for expressing the toxin or toxin analogue, e) harvesting the toxin or toxin analogue from the culture, and f) optionally subjecting the toxin to posttranslational modifications to produce the detoxified toxin or toxin analogue.

In step a) of the method, the nucleotide sequence may for instance be isolated by establishing a P. multocida gene library and screening for toxin-positive clones in accordance with established methods as indicated above as well as described in detail in Example 4 below.

In step b) of the method, the modification of the sequence optionally carried out may be performed before or after the sequence has been inserted in the vector. The modification may comprise substitution, addition, insertion or deletion of one or more nucleotides in the sequence or a combination thereof, as explained above.

The transformation in step c) of the method may be carried out by standard procedures, such as disclosed in Maniatis et al. (ref 14).

The cultivation of the host microorganism in step d) of the method may be carried out in a culture medium conventionally used for fermentation purposes, e.g. Luria Broth medium, and under conditions with respect to pH, temperature, aeration, etc. suited to the type of microorganism in question. e.g. as disclosed in Maniatis et al. (ref. 14).

In step e) of the method, the harvesting of the toxin or toxin analogue may proceed by well-known methods such as by precipitation, gel filtration, ion exchange or HPLC reverse phase chromatography or immunoaffinity chromatography.

If the nucleotide sequence coding for the toxin or toxin analogue has not been modified in step b) of the method to result in expression of the detoxified toxin or toxin analogue, the toxin or toxin analogue should be subjected to posttranslational modifications in step f) of the method, for instance thermal treatment, treatment with a chemical such as formaldehyde, glutaraldehyde or a suitable proteolytic zyme, e.g. trypsin. or substitution, addition, insertion or deletion of one or more amino acids in the toxin or toxin analogue.

In a still further aspect, the invention concerns a method of producing a vaccine for immunizing an animal, including a human being, against diseases caused by microorganisms producing an osteolytic toxin, the method comprising formulating the toxin or toxin analogue produced by recombinant DNA techniques or by peptide synthesis as described above with an immunologically acceptable carrier or vehicle, such as those indicated above.

In a further, interesting aspect, the present invention relates to a non-pathogenic microorganism which carries and is capable of expressing an inserted nucleotide sequence coding for an immunogenic detoxified *P. multocida* toxin or toxin analogue for use as a live vaccine for the immunization of an animal against diseases caused by microorganisms producing an osteolytic toxin. The use of a live vaccine might be advantageous since there is some indication that vaccines based on living organisms show an excellent immunogenicity, often conferring a lifelong immunity against the disease in question. Live vaccines also tend to be less expensive to produce than those based on a purified protein, no purification step being required.

In order to provide expression of the toxin or toxin analogue in detoxified form, the nucleotide sequence coding for the toxin or toxin analogue may be suitably modified, either before or after introduction into the host microorganism, by substitution, addition, insertion or deletion of one or more nucleotides in the sequence or a combination of these measures, as explained above.

In a particularly advantageous embodiment of the live vaccine of the invention, the nucleotide sequence coding for the toxin or toxin analogue is expressed on the outer surface of the host cell. This provides a favorable presentation of the toxin epitope(s) which will be recognized by the immune defense mechanisms of the animal to which the live vaccine is administered, thus provoking an appropriate immune response. One way of providing the expression of the toxin or toxin analogue on the cell surface is to fuse the nucleotide sequence encoding the toxin or toxin analogue to another nucleotide sequence encoding a surface protein or a subsequence thereof (e.g. a signal peptide) which cause the toxin or toxin analogue to be expressed on the outer surface of the host cell, optionally as a fused polypeptide. Examples of useful surface proteins are adhesins, fimbrial proteins, e.g. the *E. coli* K88 or Type 1 fimbrial protein, or the LamB protein of *E. coli*.

The invention also relates to the use of a recombinant, detoxified immunogenic *P. multocida* toxin or toxin analogue for preparing a vaccine for the immunization of an animal, including a human being, against diseases caused by microorganisms producing an osteolytic toxin. The toxin or toxin analogue used for immunization may be one encoded by the DNA sequence shown in FIG.10 (a)–(j) (SEQ. ID. NO. 1) or a modification thereof as explained above.

Similarly, the present invention relates to a method of immunizing an animal, including a human being, against diseases caused by microorganisms producing an osteolytic toxin, the method comprising administering to the animal an immunogenically effective amount of a recombinant detoxified immunogenic *P. multocida* toxin or toxin analogue, such as the one encoded by the DNA sequence shown in FIG. 10 (a)–(j) (SEQ. ID. NO. 1) or a modification thereof. The toxin or toxin analogue may be administered intravenously, intramuscularly, subcutaneously, intraperitoneally, orally or intranasally. It is contemplated that a suitable dosage range will be 0.1–500 µg, dependent on the age and condition of the animal in question, the route and form of administration and the immunogenicity of the toxin or toxin analogue.

In a preferred embodiment, the monoclonal antibody of the present invention is one raised against the *P. multocida* toxin produced by *P. multocida* ssp. multocida 45/78, which is publicly available from the National Collection of Type Cultures (NCTC), Central Public Health Laboratory, London, England, with the accession number NCTC 12178.

In connection with the research leading to the present invention, several different monoclonal antibodies to the toxin produced by this Pasteurella strain have been prepared (vide Example 1 below), representative examples of which are the ones produced by the hybridoma cell lines P3F37 and P3F51. Samples of these cell lines were deposited in accordance with the provisions of the Budapest Treaty on the International Recognition of the Deposit of Microorganisms for the Purpose of Patent Procedure, on 3 Dec., 1987, in the European Collection of Animal Cell Cultures (ECACC), Centre for Applied Microbiology and Research, Porton Down, Salisbury, Wiltshire, Great Britain, with the accession numbers ECACC 87120301 and ECACC 87120302. respectively.

The monoclonal antibody of the invention may be prepared by a method comprising:

a) Immunizing a suitable animal or animal cell with an immunogenic *P. multocida* toxin or toxin analogue to obtain cells producing an antibody to said toxin or toxin analogue, b) fusing cells producing the antibody with cells of a suitable myeloma cell line,and selecting and cloning the resulting hybridoma cells producing said antibody, or c) immortalizing an unfused cell line producing said antibody, e.g. by viral transformation, followed by d) growing the cells of step b) or c) in a suitable medium to produce said antibody and harvesting the antibody from the growth medium.

The initial immunization of the animals in step a) of the method requires a modification of the conventional method of producing monoclonal antibodies disclosed by Köhler. and Milstein, Nature 256, 1975, p. 495, since, PMT, even when it is administered to mice in sublethal doses, will cause an atrophy of the spleen which seriously complicates the hybridoma technique. The animals must therefore initially be immunized with a detoxified toxin preparation as it has been found that any subsequent booster immunizations may be carried out with the native toxin which need not be detoxified before use. The immunization may otherwise be carried out according to conventional procedures, e.g. by administering a solution or suspension of the (detoxified) toxin or toxin analogue in a suitable solvent such as isotonic saline or phosphate buffered saline optionally containing an adjuvant such as one of those indicated above. Animals suited for immunization purposes are, for instance, mice, rabbits, goats, sheep, guinea pigs. etc. The bleeding of the animals and recovery of the polyclonal antibodies may be performed by conventional procedures.

The antibody-producing cells used for fusion to the myeloma cells are preferably spleen or lymph cells (e.g. lymphoblasts, B-lymphocytes, plasma cells or related cells isolated from spleen, lymph nodes or functionally related tissues). The fusion of antibody-producing cells and myeloma cells may be performed substantially as described by Köhler and Milstein, supra, that is, preferably in the presence of a fusion promoter such as polyethylene glycol. A ratio of about 3 antibody-producing cells per myeloma cell is preferred. The myeloma cell line employed is preferably of a type unable to survive in selective medium and unable to produce immunoglobulins by itself; one type of cell line frequently used for cell fusions is one which lacks the enzyme hypoxanthine-guanine phosphoribosyltransferase and which is consequently unable to grow in a medium containing hypoxanthine, aminopterin and thymidine (HAT medium).

The selection of hybridoma cells which produce an antitoxin-antibody may then be carried out by culturing unfused antibody-producing cells, unfused myeloma cells and supposedly fused cells in a selective medium (such as HAT) in which the unfused myeloma cells cannot grow and eventually die out. The unfused antibody-producing cells can only survive for a limited period of time after which they also die out. On the other hand, successfully fused cells continue to grow as they have inherited permanent growth properties from the parent myeloma cells and the ability to survive in the selective medium from the parent antibody-producing cells.

Alternatively to the production of hybridomas, immortalized unfused antibody-producing cells may be produced either by transferring the genes responsible for production of immunoglobulin from the hybridoma to another (more viable) cell line or by vital transformation as described by Klein et al., (ref. 16).

The resulting antibody-producing cells (whether hybridomas or unfused cells) may be grown in vitro after cloning, e.g. as described in Example 1 below, in a suitable medium, such as RPMI 1640. This results in the production of monoclonal antibodies of a very high purity as these are secreted into the culture supernatant by the cells. The antibodies may then be isolated by conventional methods such as centrifugation, filtration, precipitation, chromatography, or a combination thereof.

In an alternative method, the monoclonal antibodies may also be produced in the body cavity of an animal such as a mouse. In this embodiment, the antibody-producing cell is injected into an animal such as a mouse resulting in the formation of an ascites tumour which releases high concentrations of the antibody in the ascites of the animal. Although the animals will also produce normal antibodies, these will only amount to a minor percentage of the monoclonal antibodies which may be purified from ascites by standard purification procedures such as centrifugation, filtration, precipitation, chromatography or a combination thereof.

In a further aspect, the invention relates to a diagnostic agent which comprises a monoclonal antibody as defined above.

Although in some cases such as when the diagnostic agent is to be employed in an agglutination assay in which solid particles to which the antibody is coupled agglutinate in the presence of a *P. multocida* toxin in the sample subjected to testing, no labelling of the monoclonal antibody is necessary, it is preferred for most purposes to provide the antibody with a label in order to detect bound antibody. In a double antibody ("sandwich") assay, at least one of the antibodies may be provided with a label. Substances useful as labels in the present context may be selected from enzymes, fluorescers, radioactive isotopes and complexing agents such as biotin.

Examples of enzymes which may be used as label substances are peroxidases, e.g. horseradish peroxidase, or phosphatases. e.g. alkaline phosphatases. As enzymes are not directly detectable, they must be combined with a substrate to form a detectable reaction product which may, for instance, be fluorescent or coloured. Examples of useful substrates are $H_2O_2$/o-phenylene diamine, $H_2O_2$/azinodiethylbenzthiazoline sulphonic acid and p-nitrophenylphosphate.

Examples of fluorescers useful as label substances are $H_2O_2$/p-hydroxyphenylacetic acid and methylumbelliferyl phosphate. Such substances may be detected by means of a fluorescence spectrophotometer in a manner known per se.

Examples of radioactive isotopes useful as label substances are I-125, S-35 and P-32. The radioactivity emitted by these isotopes may be measured in a gamma-counter or a scintillation counter in a manner known per se.

In a favoured embodiment, the diagnostic agent comprises at least one antibody covalently or non-covalently coupled to a solid support. This may be used in a double antibody assay in which case the antibody coupled to the solid support is not labelled. The solid support may be composed of a polymer or may comprise a matrix on which the polymer is applied. The solid support may be selected from a plastic, e.g. latex, polystyrene, polyvinylchloride, nylon, polyvinylidene difluoride, cellulose, e.g. nitrocellulose and magnetic carrier particles (e.g. iron particles coated with polystyrene).

For use in a diagnostic assay, the solid support may have any convenient shape. Thus, it may be in the form of a plate, e.g. a thin layer or, preferably, microtiter plate, a strip, film, paper or solid particles such as latex beads or the like.

Rather than being coupled directly to the solid support, the monoclonal antibody may be coupled to a ligand immobilized on a solid support. Examples of ligands include Protein A, or an immunoglobulin-specific antibody.

It should be noted that practically all methods or applications based on intact monoclonal or polyclonal antibodies could instead be performed using fragments of the monoclonal or polyclonal antibody, e.g. F(ab')$_2$ or Fab fragments (cf. Goding, 1978 (ref. 17).

For use in a sandwich assay, the diagnostic agent may additionally comprise a polyclonal antibody. This antibody may be labelled and/or coupled to a solid support as described above in connection with the monoclonal antibody.

The monoclonal antibody of the invention may be used in a method of determining the presence of a P. multocida toxin or toxin analogue in a sample, the method comprising incubating the sample with a monoclonal antibody as described above and detecting the presence of bound toxin or toxin analogue resulting from said incubation. The antibody may be provided with a label as explained above and/or may be bound to a solid support as exemplified above.

In a favoured embodiment of the method, the sample is incubated with a first monoclonal antibody coupled to a solid support and subsequently with a second monoclonal or polyclonal antibody provided with a label. An example of this embodiment is the sandwich ELISA (enzyme linked immunosorbent assay) assay described in Example 2 below.

In an alternative embodiment (a so-called competitive binding assay), the sample may be incubated with a monoclonal antibody coupled to a solid support and simultaneously or subsequently with a labelled P. multocida toxin or toxin analogue the latter competing for binding sites on the antibody with any toxin or toxin analogue present in the sample.

The sample subjected to the present method may be any sample suspected of containing a P. multocida toxin or toxin analogue. Thus, the sample may be selected from bacterial suspensions, bacterial extracts, culture supernatants, animal body fluids (e.g. serum, colostrum or nasal mucous) and intermediate or final vaccine products.

Apart from the diagnostic use of the monoclonal antibody of the invention, it is contemplated to utilize the well-known ability of certain monoclonal antibodies to inhibit or block the activity of biologically active antigens by incorporating the monoclonal antibody in a composition for the passive immunization of an animal, including a human being, against diseases caused by microorganisms producing an osteolytic toxin, which comprises a monoclonal antibody as described above and a suitable carrier or vehicle. The composition may be prepared by combining an effective immunizing amount of the antibody or fragment thereof with a suitable carrier or vehicle. Examples of suitable carriers and vehicles may be the ones discussed above in connection with the vaccine of the invention. The composition may further comprise an adjuvant such as one of those indicated above.

Based on experiments with mice (cf. Example 11 below) where the monoclonal antibody induced passive immunity against PMT, it is contemplated that a PMT-specific antibody may be used for prophylactic or therapeutic treatment of atrophic rhinitis in pigs. It may be administered intravenously, subcutaneously or intramuscularly as well as orally in suitably protected form or by means of an intranasal aerosol.

A further use of the monoclonal antibody of the invention is in a method of isolating a P. multocida toxin or toxin analogue, the method comprising adsorbing a biological material containing said toxin or toxin analogue to a matrix comprising an immobilized monoclonal antibody as described above, eluting said toxin or toxin analogue from said matrix and recovering said toxin or toxin analogue from the eluate.

The matrix may be composed of any suitable material usually employed for affinity chromatographic purposes such as agarose, dextran, controlled pore glass, DEAE cellulose, optionally activated by means of CNBr, divinylsulphone, etc. in a manner known per se.

The present invention further relates to a diagnostic agent for the detection of PMT-producing microorganisms, which comprises a labelled DNA sequence homologous with a DNA sequence coding for a Pasteurella multocida toxin or toxin analogue. In this context, the tea "homologous with" is intended to indicate than the DNA sequence comprises at least one stretch of deoxyribonucleotides of at least 15 bases with 80% homology to a part of the shown sequence or to a part of the sequence encoding a toxin analogue.

In a method employing the diagnostic agent, probe DNA is labelled, and the DNA is denatured to separate the strands in both probe and sample DNA; the DNAs are mixed and the strands are left to reform the double helical structure, but in case of homology, some of the probe DNA will have combined with the sample DNA. This is known as hybridization and is described by for instance Southern, 1980, (ref. 18). The DNA used as the probe should have a unique nucleotide sequence of a certain length in order to be sufficiently specific as a diagnostic agent. The probe DNA may advantageously be labelled with a radioactive isotope such as H-3, I-125, S-35 or P-32 as described e.g. by Rigby et al., 1977, (ref. 19); a complexing agent such as biotin (Gebeyechu et al., 1987, (ref. 20); or with digoxygenin-dUTP according to the method described by the manufacturer of the reagent, Boehringer, Mannheim.

In a particular embodiment of the invention, detection of the presence of Pasteurella multocida toxin producing microorganisms in a sample is performed by use of a DNA probe in the polymerase chain reaction procedure described by Seiki et al., 1985, (ref. 21). The polymerase chain reaction (PCR) is a procedure used for the amplification of DNA present in a sample. The procedure involves the use of two oligonucleotide primers which flank the DNA segment to be amplified. The oligonucleotide primers may e.g. comprise the regions of the gene coding for Pasteurella multocida toxin or toxin analogue and may thus be used to amplify the said gene or part of it present in a sample. The oligonucleotide primers hybridize to opposite strands of the DNA sequence to be amplified, and the primers are extended by using DNA polymerase, e.g. the Klenow fragment of E.coli DNA polymerase I or another useful DNA polymerase such as the Taq DNA polymerase, so as to synthesize a DNA sequence which is complementary to the DNA sequence to which the primers are annealed. Subsequent to the synthesis of these complementary sequences, the DNA synthesized is denatured, e.g. by heating, from the "parent DNA strings", and the parent strings as well as the newly synthesized DNA strings are subjected to a new PCR amplification cycle. In this manner, it is possible to obtain a substantial amplification of specific DNA sequences which are present in a sample. By use of the PCR amplification method, it may be possible to amplify and then detect originally very small and undetectable amounts of DNA sequences present in a sample.

In a still further aspect, the present invention relates to a method of determining the presence of antibodies against a *P. multocida* toxin or toxin analogue in a sample, the method comprising incubating the sample with a *P. multocida* toxin or toxin analogue and detecting the presence of bound antibody resulting from said incubation.

A diagnostic agent comprising the toxin or toxin analogue used in this method may otherwise exhibit any of the features described above for diagnostic agents comprising the monoclonal antibody and be used in similar detection methods although these will detect bound antibody rather than bound toxin as such. The diagnostic agent may be useful, for instance as a reference standard or to detect anti-toxin antibodies in body fluids, e.g. serum, colostrum or nasal mucous, from animals exposed to the toxin or toxin analogue.

A still further use of a *P. multocida* toxin or toxin analogue is for the preparation of a toxin reference standard which may be useful, as a standard of comparison in qualitative or quantitative analytical procedures. In a qualitative procedure, the standard toxin in a known concentration may be reacted with a monoclonal or a polyclonal antibody raised against the toxin or toxin analogue, a positive reaction indicating the specificity of the antibodies. In another aspect, the reference standard preparation is applied in a quantitative analytical procedure by which different concentrations of the preparation is reacted with a monoclonal or a polyclonal antibody in order to provide a calibration curve which may allow the precise amount of toxin or toxin analogue in a sample to be estimated.

BRIEF DESCRIPTION OF THE DRAWINGS

The invention is further disclosed in the following with reference to the drawings in which

FIG. 9 is a restriction enzyme cleavage map of the pmt gene. The shaded area denotes the pmt gene, the vertically hatched area denotes a probable promoter, and the hatched area denotes a probable terminator.

FIG. 10 (a)-(j) (SEQ. ID. NO. 1) shows the DNA sequence of the pmt gene region and the amino acid sequence deduced on the basis of the DNA sequence. The amino acids are identified with single-letter codes according to conventional usage. The amino acid sequence has been shown to start at position 213 or 219.

. . . negative
- - - infected

_vaccinated

Figure 18:
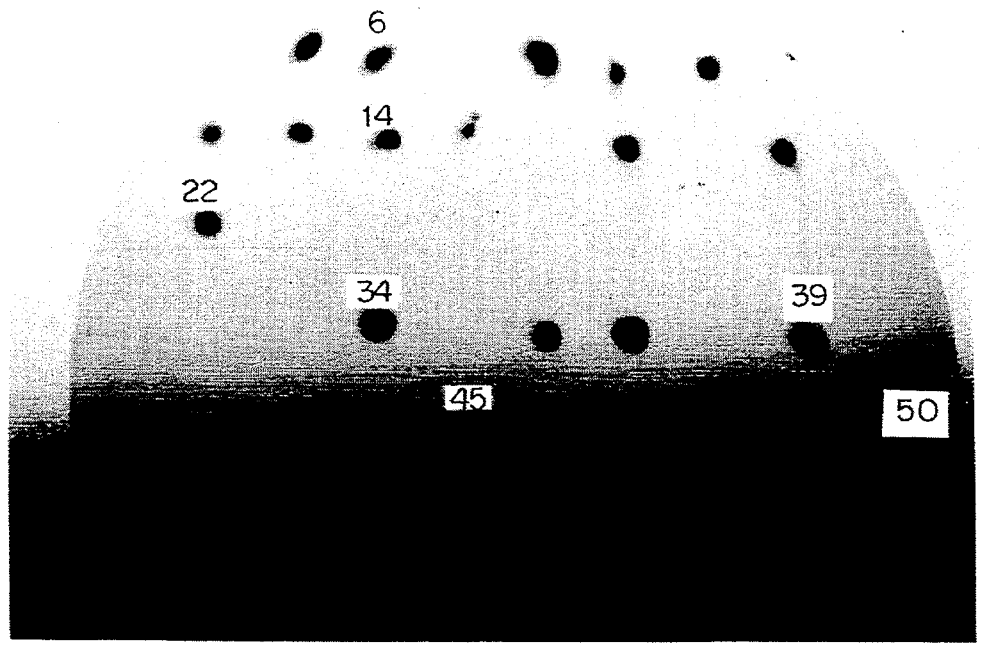

FIG. 18 shows the colony hybridization of P. multocida isolates, testing 17 toxin-positive and 18-toxin-negative strains as determined by the ELISA and EBL cell tests for the presence of the pmt gene.

Figure 19A:
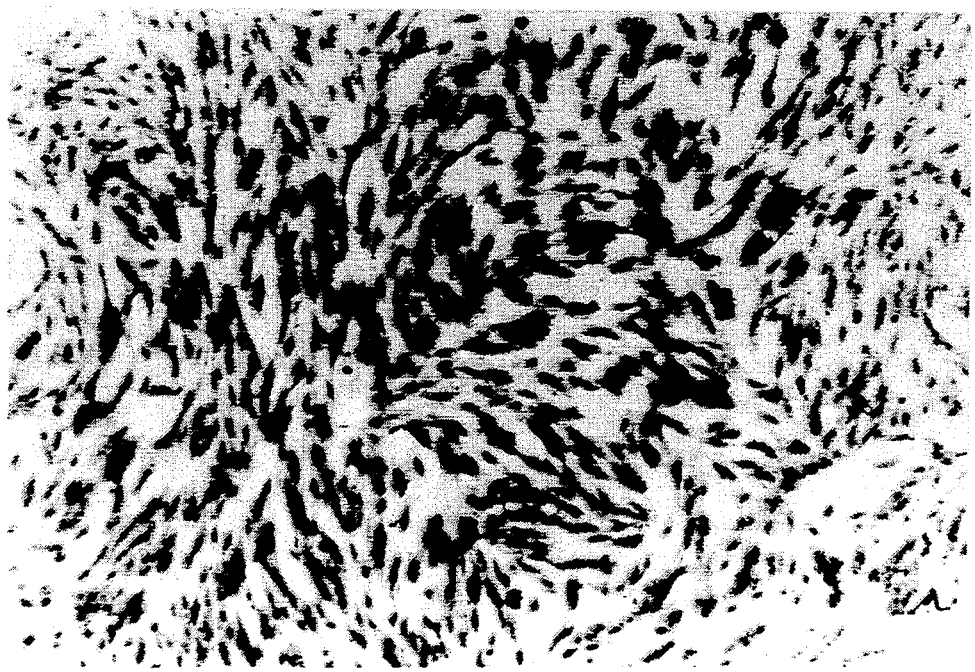
Figure 19B:
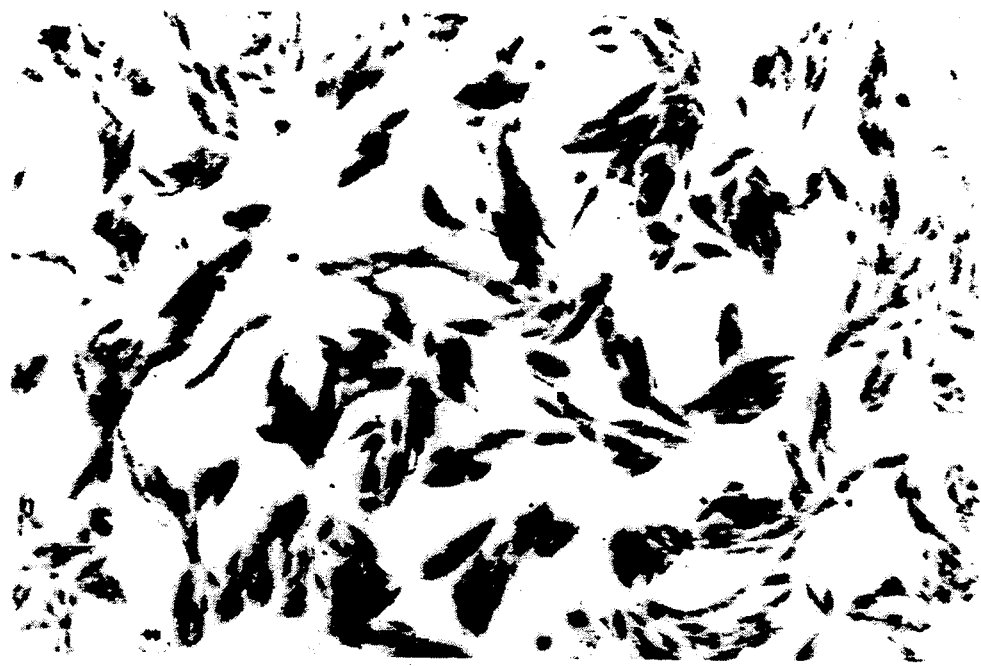
Figure 19C:
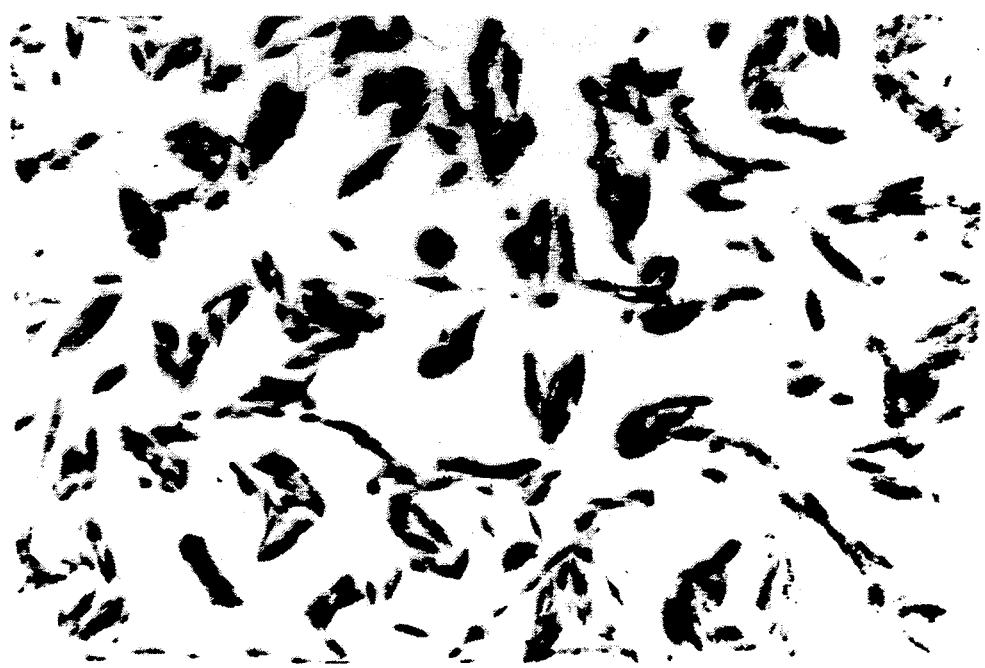

FIG. 19 a-c shows the determination of toxic activities of cell-free sonicates of recombinant E.coli clones. E.coli strain MT102 with PUN121 had no cytopathic effect on EBL-cells when diluted 1/25 in PBS (a). Sonicates of E.coli SPE312 (b) and toxigenic P. multocida (NCTC 12178) (c) diluted 1/3125 showed significant and identical effects (80 X magnification).

Figure 20:
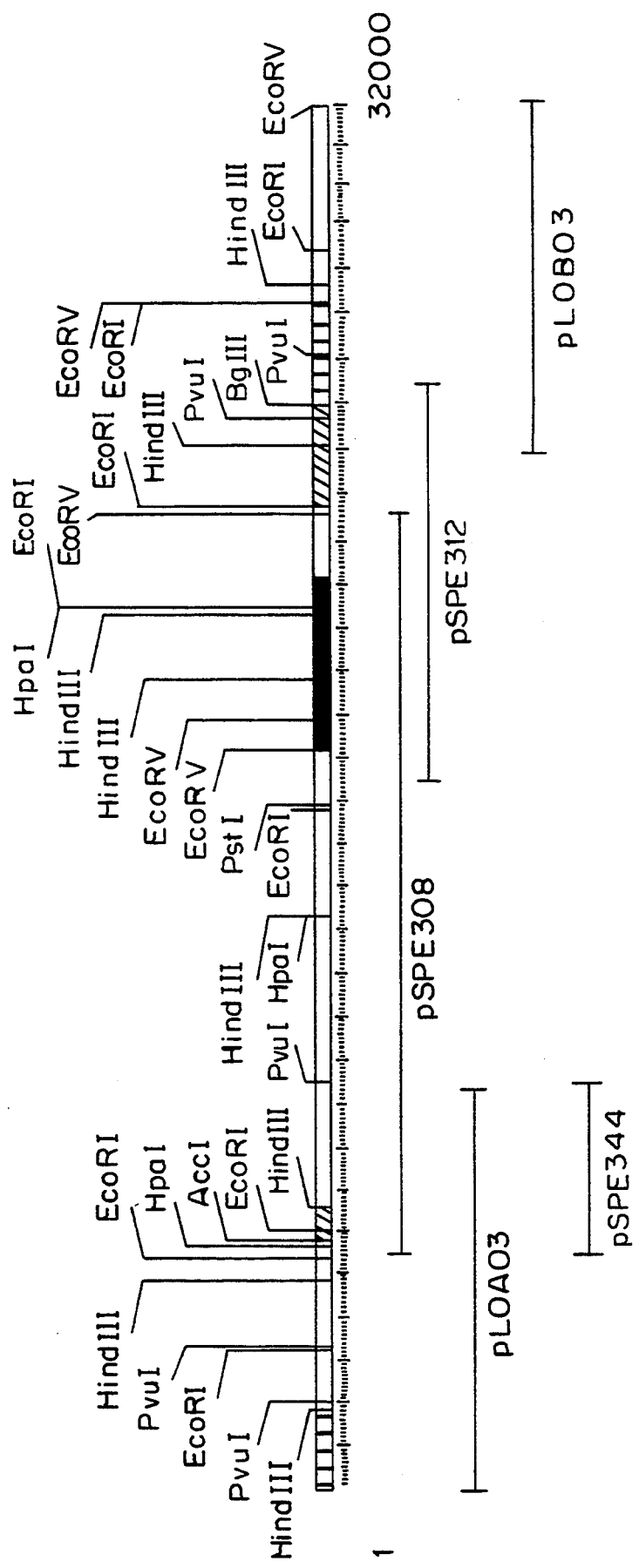

FIG. 20 shows the P. multocida DNA flanking the pmt-gene (black area). The extension of the inserts of the plasmids pSPE308, pSPE312, pSPE344, pLOA03 and pLOB03 are indicated. The DNA contained in the probes used for the blotting (slant hatched area). and the fragments which contain the two homologous sequences (vertically hatched area) are shown.

Figure 21:
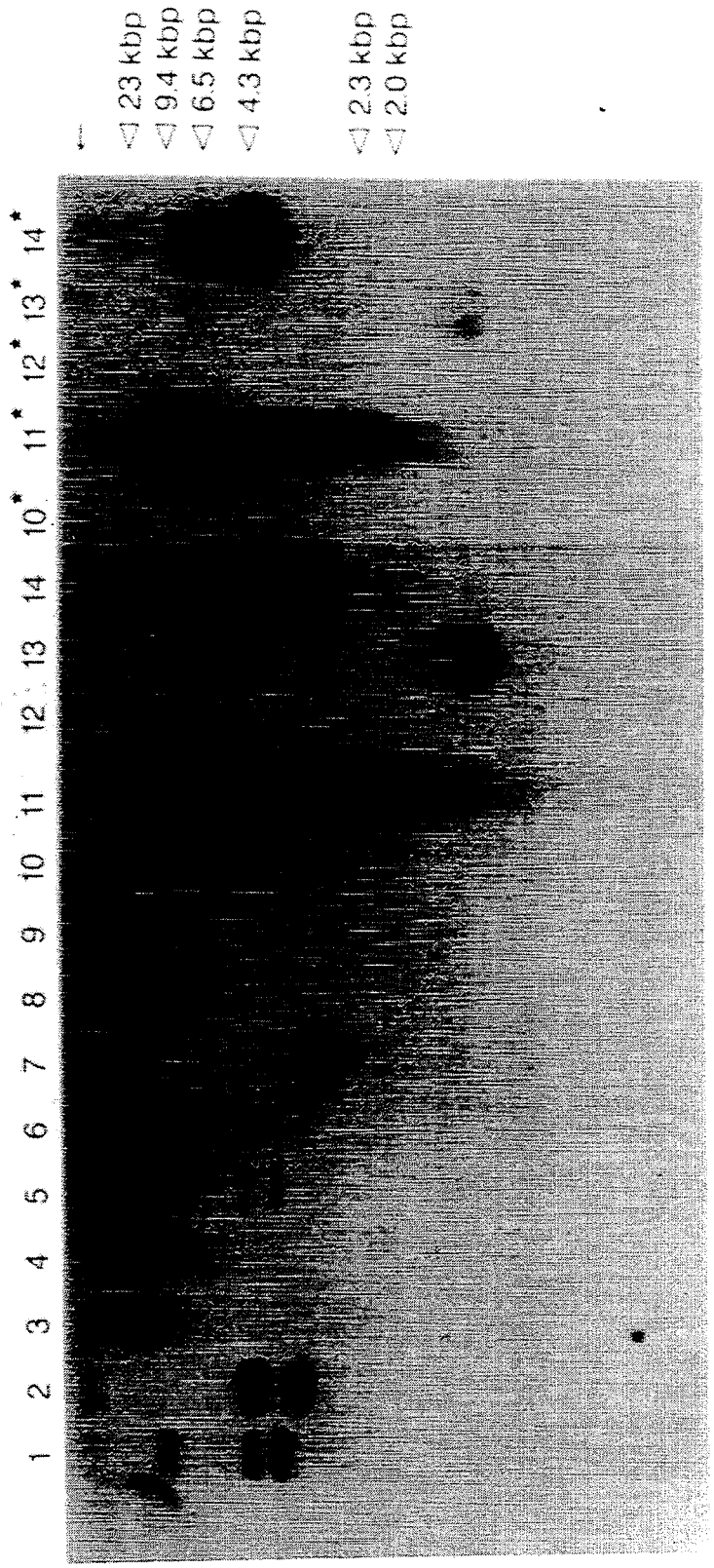

FIG. 21 shows a Southern blot of restriction enzyme digested P. multocida DNA. Probe: 2,4 kb BglII-EcoRI fragment of pLOB03. lanes 10*–14* is a short time exposure of lanes 10–14.

Lanes 1–4: Toxigenic P. multocida 45/78. Lanes 5–9: Nontoxtgenic P. multocida MH81 P8. Lane 10: pSPE308. Lane 11: pLOA03. Lane 12: pLOA02. Lane 13: pSPE312. Lane 14: pLOB03.

Restriction enzymes used: HindIII: Lanes 1, 5, 10, 11, 12 and 13.

EcoRI: Lanes 2, 6 and 14. BglII: Lanes 3 and 7. PvuII: Lanes 4 and 8.

PstI: Lane 9.

Figure 22:
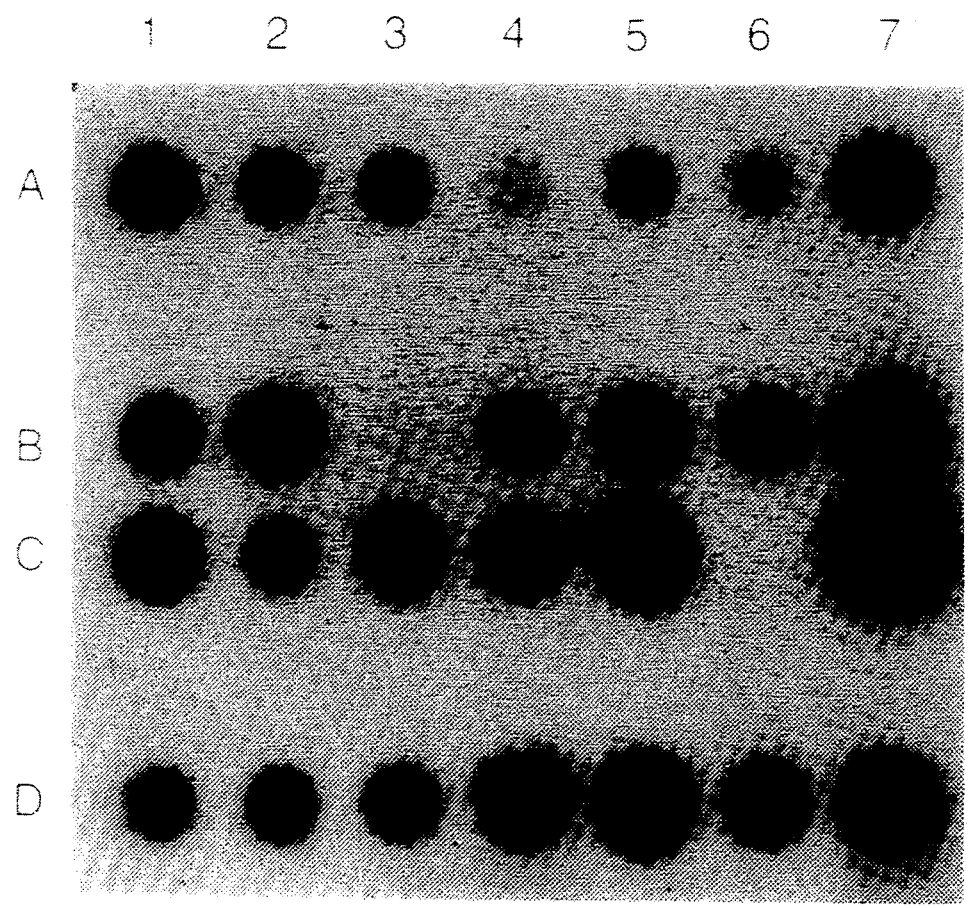

FIG. 22 shows a dot blot of 24 different P. multocida bacteriophage genomes. Probe: pLOA03. The probe does not hybridize to B2 and C5. A7: pSPE308; B7: pSPE312, C7:pLOA03 and D7:pLOB03 are positive controls.

EXAMPLE 1

Preparation of monoclonal antibodies against P. multocida toxin

Immunization

P. multocida toxin (PMT) was purified as described by Foged et al. (ref. 6), i.e., by 50% $(NH_4)_2SO_4$-precipitation of a cell-free extract of the toxigenic type D strain of P. multocida ssp. multocida 5/78 (refs. 3, 22) followed by DEAE-Sephacel ® chromatography and preparative polyacrylamide gel electrophoresis (PAGE) in a manner known per se.

A suspension of the $(NH_4)_2SO_4$-precipitate prepared as described above and containing approx. 25 μg/ml of PMT was detoxified by incubation with 0.37% formaldehyde at 37° C. for 1 h. Female BALB/c mice (8–12 weeks old) were immunized subcutaneously on day 0 and 14 with 300 μl of a 1:1 dilution of the crude preparation of detoxified P. multocida toxin and Freund's incomplete adjuvant (day 0) or PBS (day 14). On day 30 and 45 1 μg of native PMT in 200 μl PBS was injected subcutaneously and on day 60 the mice were boosted intravenously with 0.5 μg of PMT in 100 μl PBS. Three days after the booster injection the mice were sacrified and their spleens removed for fusion.

Production of hybridoma cell lines and monoclonal antibodies

According to procedures described by Fazetas et al. (ref. 23) and Gebeychu et al. (ref. 20), the spleen cells and P3-X63-Ag8.653 myeloma cells were fused using 50% PEG 4000 GK (Merck) and the resulting hybridoma cells were grown selectively in hypoxanthine/aminopterin/-thymine (HAT) -supplemented RPMI 1640 medium containing 15% fetal calf serum (FCS) and 4% human endothelial cell supernatant (Costar, The Netherlands).

Hybridoma cell lines were selected by analyzing their respective monoclonal antibodies by ELISA and immunoblotting.

ELISA for detection and titration of monoclonal antibodies

Microtitre plates (96-well Immuno Plate II Nunc, Denmark) were coated with 50 μl/well of a 0.75 μg/ml solution of purified PMT in PBS at 4° C. for 16 h. and at 20° C. for 1 h. The wells were emptied and blocked with 200 μl PBS-T-BSA (PBS containing 0 05% (v/v) Tweene ®20 and 1% (w/v) bovine serum albumin) per well at 20° C. for 1 h., then washed 3 times with PBS-T. Fifty μl/well of hybridoma culture supernatant was applied at 20° C. for 1 h., and the plates were washed as described above. The anti-PMT antibody activity was measured colorimetrically after incubating at 20° C. for 1 h. with 50 μl/well of sheep anti-mouse immunoglobulin conjugated with horseradish peroxidase (Amersham International, U.K.) diluted 1:1,500 in PBS-T-BSA and (after 3 further PBS-T washes as above) with 50 μl of an o-phenylene diamine (OPD)-$H_2O_2$ substrate solution. The reaction was stopped with 150 μl of 2 M $H_2SO_4$ after 5 min. and absorbance was determined in a Kontron SLT-210 photometer (SLT Lab-instr., Zürich, Switzerland) at 492 nm (ref. 620 nm).

The mean absorbance at the saturation level of the titration curve ($A_{sat}$) and the mean concentration of the MAb that resulted in 50% of the $A_{sat}$(C50%) was determined by ELISA as described above, except that serial dilutions of the protein-A purified MAb in PBS-T-BSA was used. All results were based on at least duplicate determinations.

Immunoblotting

To determine the specificity of the monoclonal antibodies, the proteins contained in a crude cell-free extract of P. multocida 5/78, were separated by SDS-PAGE before transfer to a nitrocellulose membrane and immunological detection. Polyacrylamide gels (total acrylamide: 10%, relative bis-acrylamide: 3%) and an electrophoresis buffer were prepared according to Laemmli (ref. 24). Electrophoresis was performed vertically at 10° C. at a constant voltage of 60 V for 16 h. or 250 V for 4 h. Protein-bands on gels were either visualized by silver staining with a detection limit of less than 1 ng of protein per band (8) or transferred to a nitrocellulose membrane (0.45 μm) using a semidry electroblotter (Artcos, Ølstykke, Denmark (9)). The proteins on the nitrocellulose membrane were either detected by a colloidal gold silver enhancement staining method (detection limit: approx. 0.5 ng of protein per band) (ref. 25) or immunologically by a modification of the method previously described by Bjerrum et al. (ref. 26). A positive reaction in immunoblotting was recorded as + or (+), when an intense (or weak) staining of the PMT-band but no other protein band was observed. Staining of other bands or no reaction was recorded as -.

The molecular weight of PMT was estimated by comparison with known markers: ovalbumin (43.0 kd), BSA (66.3 kd), phosphorylase B (97.4 kd), β-galactosidase (116.2 kd), RNA-polymerase β(150.6 kd) and β'(155.2 kd) and myosin (approx. 200 kd).

ELISA for estimating epitope specificity

Estimation of apparent epitope specificity of anti-PMT MAbs was done by a competitive ELISA similar to a method described by Anderson et al. (ref. 27). Microtitre plates were coated with PMT and blocked as described above. Fifty µl of the competing MAb diluted to 10 µg/ml in PBS-T-BSA was added and incubated for 1 h. at 20° C. Without aspiration of the wells 25 µl biotinylated monoclonal antibody was added and the mixture was incubated for 20 min. at 20° C. After washings 50 µl of a 1:2,500 dilution of horseradish peroxidase-conjugated avidin (Kem-En-Tec, Denmark) was added and the plates incubated for 45 min. at 20° C. The substrate, reaction time and determination of absorbance were as described above.

The biotinylated MAb was used at a working dilution resulting in approx. 75% of the absorbance at the saturation level on the titration curve. This curve was obtained by using a diluent instead of the competing MAb and serial dilutions of the biotinylated MAb. The extent of blocking by a competitive MAb was calculated according to the formula $(1-A/A_o) \times 100\%$, where A is the mean of the absorbance for three wells with the competing MAb and $A_o$ is the mean of the absorbance of eight wells containing diluent instead of the competing MAb.

The date of 10 representative monoclonal antibodies (Mabs), all of the IgG$_1$ subclass, out of 92 ELISA-positive supernatants are shown in Tables 1 and 2.

TABLE 1

| Characterization of 10 representative MAbs | | | | |
|---|---|---|---|---|
| Hybridoma group No. | Representative MAb | $A_{sat}$ | $c_{50\%}$ ng/ml | Immunoblotting |
| 1 | P3F51 | 1.2 | 110 | + |
| 2 | P3F64 | 0.4 | 250 | + |
| 3 | P3F37 | 0.7 | 30 | (+) |
| 4 | P4F58 | 0.7 | 110 | + |
| 5 | P3F22 | 0.6 | 35 | + |
| 6 | P4F46 | 1.3 | 55 | + |
| 7 | P4F38 | 1.9 | 40 | + |
| 8 | P4F55 | 1.3 | 33 | + |
| 9 | P3F50 | 1.8 | 315 | + |
| 10 | P3F53 | 0.9 | 300 | (+) | a) $A_{sat}$ is the mean absorbance at 492 nm at the saturation level in the ELISA titration.

grown in "cell factories" (Nunc, Denmark) at 37° C. in RPMI 1640 medium supplemented with 10% FCS as well as injected about $5 \times 10^6$ cells/mouse into Balb/c mice which after a certain incubation time leads to the formation of a tumour in the peritoneum of the mouse releasing high quantities of antibody in its ascites (about 5–10 ml containing 5–25 mg/ml).

The hybridoma cell culture supernatants were passed through a protein A agarose column (Kem-En-Tec, Denmark). Bound antibodies were eluted with 0.05M acetic acid, pH 4.0, or 0.03M citric acid, pH 3.0, and immediately neutralized with an appropriate buffer. Purified antibodies were biotinylated as described by Guesdon et al., 1979, (ref. 28).

Two hybridoma cell lines, P3F37 and P3F51 shown in Table 1 to produce MAb, were deposited on 3 Dec., 1987 in the European Collection of Animal Cell Cultures, Centre for Applied Microbiology and Research. Porton Down, Salisbury, Wiltshire SP4OJG, U.K., with the Accession numbers ECACC 87120301 and ECACC 87120302, respectively.

EXAMPLE 2

Quantification of PMT

Quantification of PET was carried out by a sandwich ELISA procedure. The sandwich ELISA was initiated by coating each well of a microtitre plate (96 wells Immuno Plate II, Nunc, Denmark) with 50 µl of 2 µg/ml of the anti-PMT MAb, P3F51 (produced in Example 1) in 0.05M carbonate buffer, pH 9.6 for 16 hours at 4° C. and 1 hour at 20° C. Each well was incubated for 1 hour with 200 µl of phosphate-buffered saline containing 0.05% Tween 20 and 1% bovine serum albumine (PBS-T-BSA). The plates could be stored for at least 6 months by applying 20 µl/well of PBS-sorbitol and sealing with adhesive tape. The analysis was initiated by two PBS-T washings followed by incubation of 50 µl/well of solutions expected to contain PMT. The solutions were appropriately diluted in PBS-T-BSA and incubated for 1 hour at 20° C. After 3 PBS-T washings each well was incubated with 50 µl of 0.5 µg/ml of the biotin conjugated MAb, P3F37, for 1 hour at 20° C. followed by another 3 PBS-T washings and incubation with 50 µl/well of a 1:2,500 dilution of horseradish-peroxidase conjugated avidin (Kem-En-Tec, Denmark) for 45 min. at 20° C. Finally, 50 µl/well of an o-phonylene diamine/H$_2$O$_2$ solution was added. The reaction

TABLE 2

| Extent of blocking by 10 representative MAbs in the competitive ELISA | | | | | | | | | | | |
|---|---|---|---|---|---|---|---|---|---|---|---|
| Competing MAb (hybridoma group No.) | | Biotinylated detector MAb (% decrease in $A_o^a$) | | | | | | | | | |
| | | 1 | 2 | 3 | 4 | 5 | 6 | 7 | 8 | 9 | 10 |
| P3F51 | (1) | 92 | b | | | | | | | | |
| P3F64 | (2) | | 95 | 44 | | | | | | | |
| P3F37 | (3) | | 63 | 95 | 78 | | | | | | |
| P4F58 | (4) | | | 91 | 96 | 73 | | | | | |
| P3F22 | (5) | | | | 71 | 88 | | | | | |
| P4F46[c] | (6) | | | | | | 92 | 90 | 93 | 16 | |
| P4F38[c] | (7) | | | | | | 93 | 92 | 95 | 27 | |
| P4F55[c] | (8) | | | | | | 92 | 92 | 95 | 15 | |
| P3F50 | (9) | | | | | | 16 | 24 | 13 | 84 | 91 |
| P3F53 | (10) | | | | | | | | | 56 | 83 |
| $A_o$ | | 1.43 | 0.19 | 0.53 | 0.80 | 0.64 | 0.64 | 0.85 | 1.01 | 0.26 | 0.52 | a) $A_o$ is the mean absorbance with diluent instead of competing MAb
b) No blocking (between 12% increase and 9% decrease in $A_o$)
c) The closely related hybridoma groups 6, 7 and 8 were differentiated by a two-site competitive ELISA using a catching MAb (method not described). Results indicated that group 6 was related to groups 3 and 4, group 7 to no other groups and group 8 to group 1.

The selected hybridoma cell lines were then cloned until they were stable. The resulting clones were then was stopped with 2M H$_2$SO$_4$ after 5 min. and absorbance was determined in an Kontron SLT-210 photometer (SLT Labinstr., Zurich, Switzerland) at 492 nm (ref. 620 nm).

Calibration was performed with a PMT-preparation quantified by amino acid analysis (ref. 6) and all quantitative data were means of at least dual determinations.

Figure 1:
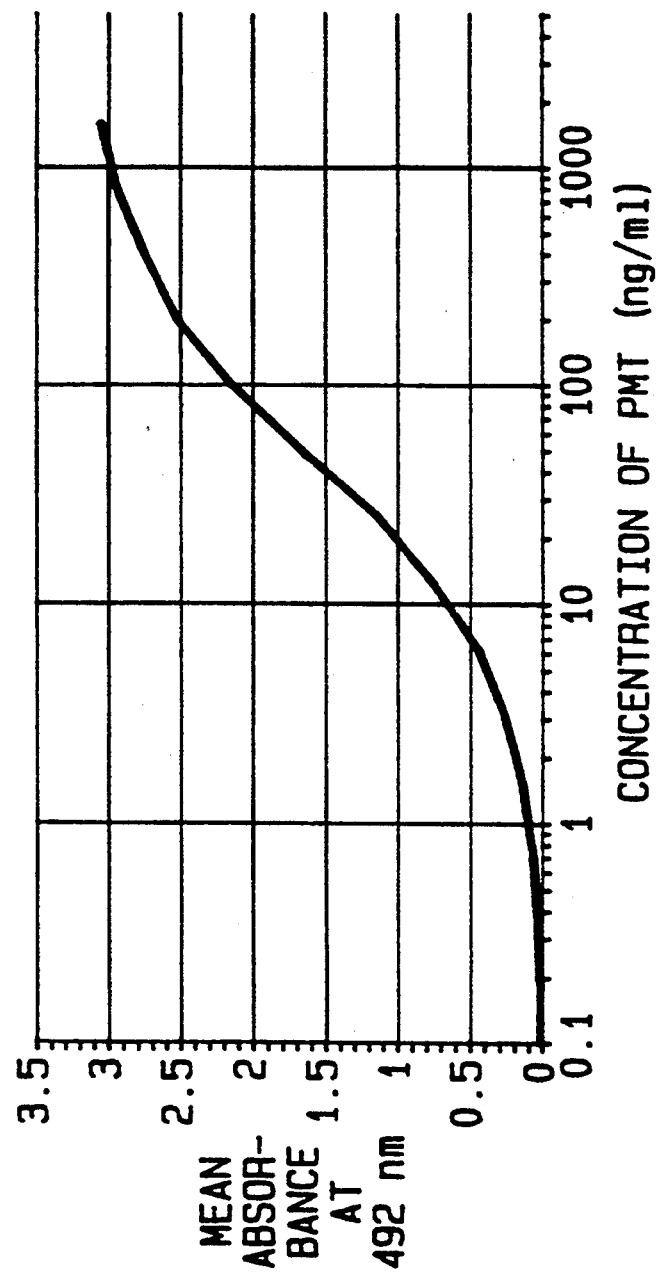
FIG. 1 is a graph showing the titration of PMT in a quantitative sandwich ELISA. The absorbance at 492 nm obtained in the ELISA is plotted against the PMT concentration. The minimum detectable concentration of PMT is about 1 ng/ml corresponding to about 50 pg or 0.35 fmol.

Using a sandwich ELISA, with the MAb P3F51 as catching antibody and biotinylated Mab P3F37 as detecting antibody, it was possible to detect less than 50 pg of PMT in a 50 μl sample. PMT at a concentration of 1 ng/ml resulted in an $A_{492}$ of approx. 0.1 corresponding to more than 8 times the background absorbance (cf. FIG. 1).

EXAMPLE 3

Affinity purification of PMT

About 100 mg of the protein-A purified MAb P3F51 prepared as described in Example 1 was coupled to 40 ml divinyl sulphone agarose (Mini-Leak, Kem-En-Tec, Denmark) as described by the manufacturer and loaded on a column (2.5×10 cm). The supernatant obtained by cultivation of the toxigenic type D strain *P. multocida 45/78* was centrifuged (12,000×g for 30 min. at 4° C.), filtered (Gelman, 0.45 μm), mixed with 1/10 vol. of 1 M Tris-HCl, pH 7.7 and NaCl was added to 0.5 M before application to the affinity column. Repeated washings before elution of the column were carried out with an 0.1M Tris-HCl buffer containing first 1% Triton® X-100, then 1.5 M NaCl and finally 0.1 M NaCl. All washing buffers contained 0.1% sodium azide and had a pH of 7.8. The PMT was eluted by 0.1M glycine-HCl, pH 2.8 and immediately neutralized with 1M $K_2HPO_4$, pH 9.0.

Figure 2:
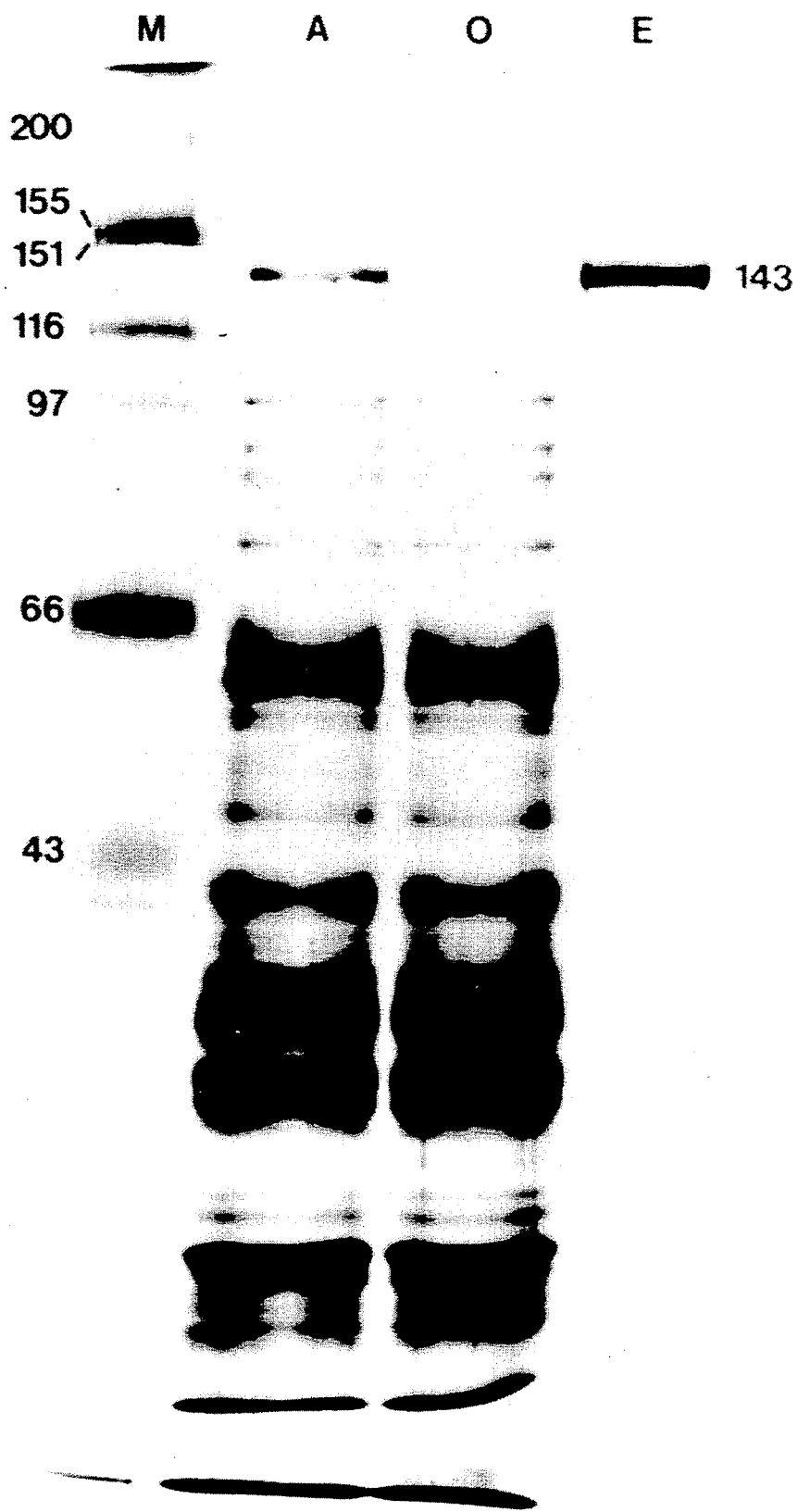
FIG. 2 shows an SDS-PAGE of fractions from the affinity chromatography described in Example 3. Lane A: the culture supernatant applied on the column, lane O: the effluent from the column, lane E: the eluted purified PMT, and lane M: molecular weight marker proteins.
Figure 3:
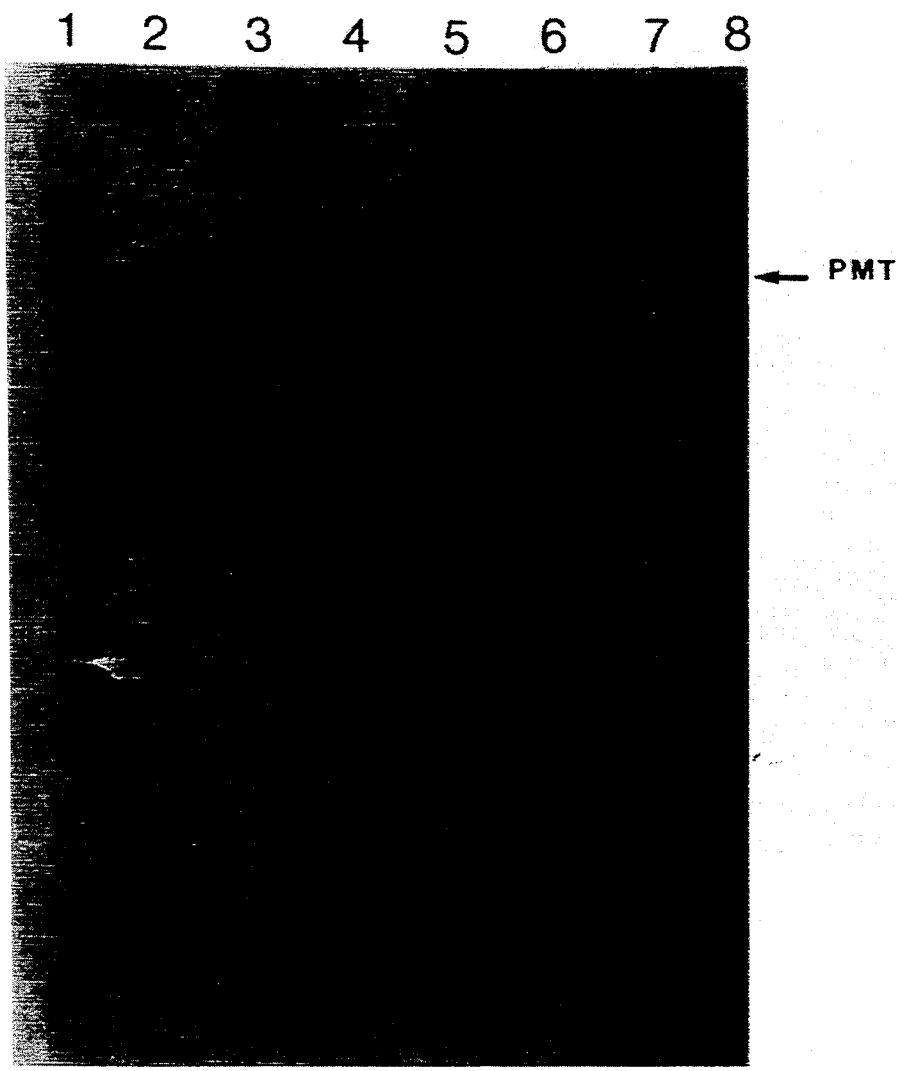
FIG. 3 is a Western blot showing PMT production by the 5 positive recombinant *E. Coli* clones detected in the screening procedure. Lane 1: SPE 301; lanes 2 and 3: SPE 308; lane 4: SPE 315; lanes 5 and 6: SPE 312; lane 7: SPE 311; lane 8: purified PMT.
Figure 4:
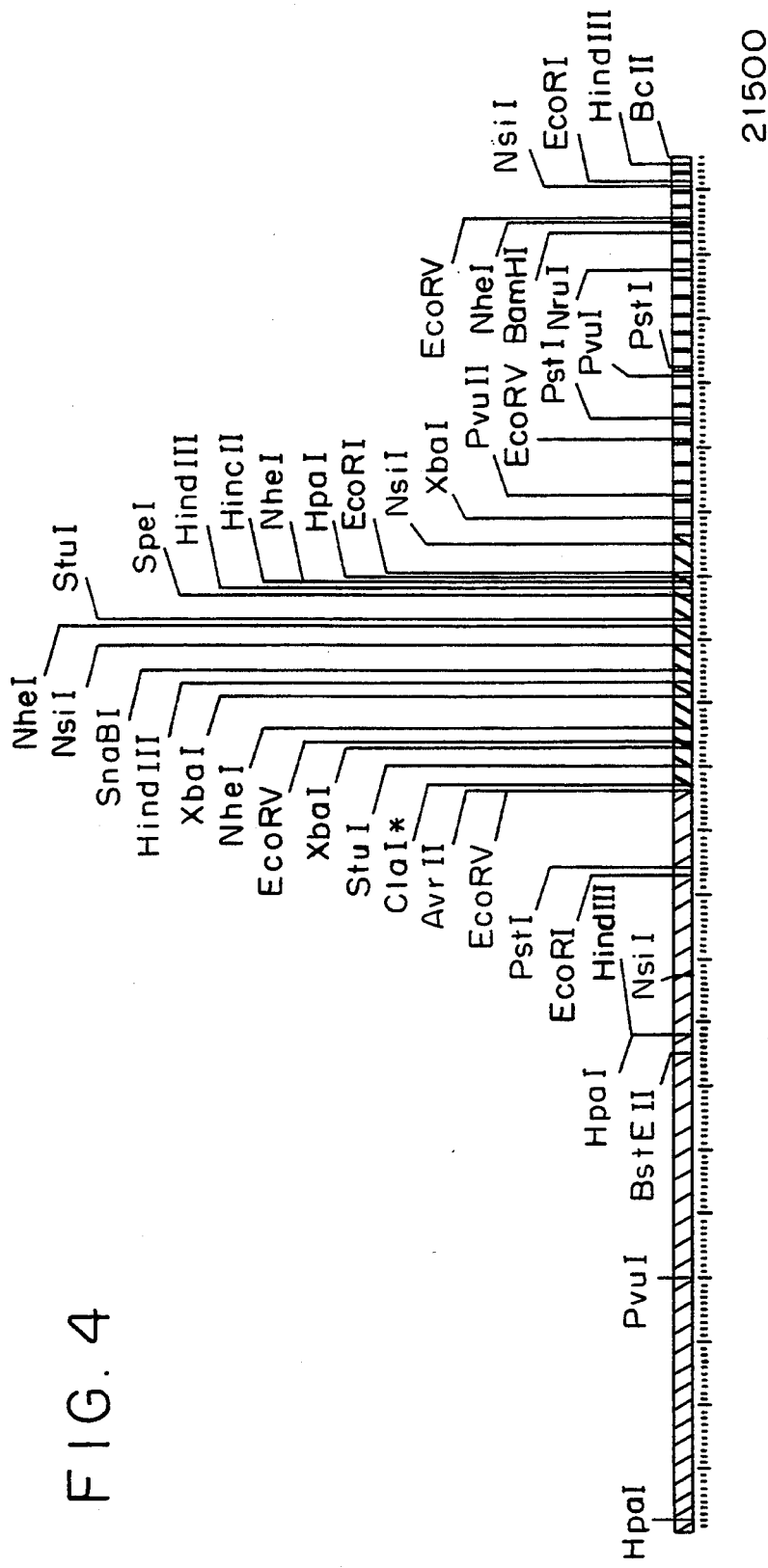
FIG. 4 is a restriction enzyme cleavage map of the plasmid pSPE 308 with a length of 21.5 kb (kilobase pairs), The hatched area denotes *P. multocida* DNA, the shaded area denotes the pmt gene and the vertically hatched area denotes plasmid pUN121 DNA.

The presence of PMT in the culture supernatant applied to the affinity column was indicated by the approx. 143 kd protein band seen by SDS-PAGE (FIG. 2). The staining pattern of proteins in the material passing through the column (i.e. the effluent) was identical to that seen with material before application, except for the 143 kd protein, which was retained on the column. Accordingly, the approx. 143 kd protein band is the only staining seen when the protein composition of the eluted material is visualized by SDS-PAGE (FIG. 2).

Approx. 2.67 mg of the 3.4 mg of PMT applied to the column was eluted in a final volume of 8 ml resulting in a 78% yield by affinity chromatography (Table 3). Nearly all the remaining 22% of PMT applied was eluted in fractions with PMT-concentrations below 50 μg/ml.

The specific purity (μg PMT/mg protein) was 284 times higher in the eluted material than in the culture supernatant (Table 3).

The average minimal dermonecrotic dose of affinity purified PMT in guinea pigs after intradermal injection and the average MCD of for embryonic bovine lung (EBL) cells in the standardized EBL-cell test (ref. 29) was approx. 35 ng and 30 pg, respectively. The $LD_{50}$ of PMT in BALB/c mice was 20 to 40 ng (corresponding to approx. 1.5 μg/kg) and in Wistar rats approx. 100 ng (corresponding to 0.5 μg/kg) when administered intraperitoneally in a single dose.

TABLE 3

Purification of PMT by affinity chromatography

| | Vol. (ml) | Protein (mg) | PMT (mg) | Purifica- factor | Recovery of PMT, % |
|---|---|---|---|---|---|
| Applied culture supernatant from | 13,200 | 970 | 3.41 | 1 | 100 |

TABLE 3-continued

Purification of PMT by affinity chromatography

| | Vol. (ml) | Protein (mg) | PMT (mg) | Purifica- factor | Recovery of PMT, % |
|---|---|---|---|---|---|
| *P. multocida* 45/78 | | | | | |
| Effluent from affinity column | 13,200 | 970 | <0.01 | N.D.[a] | <0.35 |
| Eluted material | 8 | N.D. | 2.67 | 284[b] | 78 | a) N.D. not determined
b) Estimated on the assumption of purity of PMT in the eluted material.

EXAMPLE 4

Establishment of a *P. multocida* gene library in *Escherichia coli*

Donor strain

*P. multocida* strain 45/78. The strain produces a dermonecrotic toxin as described by Foged et al. (ref. 6).

Recipient strain

*Escherichia coli* K-12 strain MT102. Genotype: thi, araD139, (araleu)Δ7697, lacΔX74, galU, rpsL, hsdR. This strain was constructed (by Mogens Trier Hnasen, Novo Industri A/S, Denmark) as follows:

| STRAIN | GENOTYPE | REFERENCE OR SOURCE |
|---|---|---|
| MC1000 | araD139, Δ(ara—Leu)7697, ΔlacX74, galU, galK, rpsL. | a) |
| So1386 | leu, Δ(deoO–deoC), Tn10-6 (91% co-transducible with deo | b) |
| MT85 | araD139, Δ(ara—leu)7697, ΔlacX74, galU, galK, rpsL, Tn10-6, Δ(deoO–deoC) | c) |
| ≠804 | met, supF, r−, m+, Δ(gal—lac) | d) | b) from Bente Mygind, Laboratoriet for Biologisk Kemi B, University of Copenhagen, Denmark.
c) constructed by Mogens Trier Hansen as shown above.
a): Casadaban and Cohen, 1980, (ref. 30).
d) Wood, 1966 (ref. 31).

Media

*P. multocida* was grown in Tryptic Soy Broth purchased from DIFCO. *E. coli* ws grown in LB medium (ref. 27).

Restriction enzymes and T4 DNA ligase were obtained from New England Biolabs and used as recommended by the manufacturer.

DNA extraction

To isolate chromosomal DNA from *P. multocida* strain 45/78, cells from a 250 ml overnight stationary culture were resuspended in 10 ml 50 mM Tris-HCl, pH 8.0, 100 mM EDTA, and incubated with 25 mg lysozyme for 20 minutes at 37° C. 2 ml of 10% (w/v) SDS were added to the mixture which was mixed and put on ice for 10 minutes. To the solution was then added 15 ml of phenol saturated with TE-buffer (10 mM Tris-HCl, pH 8.0, 1 mM EDTA), after which it was heated to 65° C., mixed gently and cooled on ice. After centrifugation for 30 minutes at 4000×g the aqueous phase was extracted with ether and ethanol precipitated, and the pellet resuspended in TE-buffer. The DNA was further purified by banding in a CsCl density gradient (ref. 27). After purification, the DNA was resuspended in 1 ml TE-buffer.

Preparation of clonable DNA fragments 9-22 kilobase pair (kb) DNA fragments with 5'GATC overhangs were prepared in the following way. Chromosomal DNA prepared as described above was digested partially by incubation with the restriction endonuclease Sau3A. At certain intervals after the incubation had been initiated, fractions of the incubation mixture were stopped with 1/20 volume 0.25 M EDTA. A sample of each fraction was run in a 1% agarose gel in TAE buffer as described in (ref. 27), and a fraction containing 4-22 kb fragments was identified. This fraction was further fractionated on a 8 ml sucrose gradient (40-10%) by layering the DNA on top of the gradient prior to ultracentrifugation at 41000 rpm for 7.5 hours. 0.5 ml subfractions were extracted, diluted with 1 volume TE-buffer, ethanol-precipitated and resuspended in TE-buffer. Two of these, containing 9-16 and 15-22 kb fragments respectively, were used in the following cloning steps.

Cloning procedure 9-16 kb and 15-22 kb DNA fragments with 5'GATC overhangs were ligated with BclI restricted pUN121 (refs. 27 and 19) by means of T4 DNA ligase. Insertion of DNA into the unique BclI site of this vector leads to inactivation of the cI gene, encoding the lambda cI repressor, which subsequently is unable to repress transcription from the plasmid-encoded λ PL promoter into the tetracycline resistance gene. The resulting plasmids were tranformed to competent E. Coli MT 102 cells as described in (ref. 27). Positive selection for clones with plasmid inserts is achieved by adding tetracycline to the medium (10 μg/ml). Using standard transformation techniques (ref. 27), 3332 tetracycline resistant recombinant E. coli clones were obtained, ~100% of them containing inserts, thus constituting a P. multocida strain 45/78 gene library in E. coil. Colonies of the E. coli clones were grown on LB-plates containing 10 μg/ml of tetracycline. A scrape of these colonies was stored at −80° C. in a 20% glycerol solution.

EXAMPLE 5

Identification of *P. multocida* toxin producing *E. coli* clones

Screening procedure

The gene library was screened using the colony blot method to transfer colonies to nitrocellulose (ref. 14).

PMT-producing clones were then detected by incubation of the nitrocellulose filters as follows: A) 15 min. in 50 mM Tris, pH 9.6,150 mM NaCl, 0.05% Tween-20 (washing buffer) and 2 μg/ml DNaseI, B) 2×10 min. in washing buffer without DNaseI, C) 30 min. in washing buffer and 3% gelatine and heated, D) 2×10 min. in washing buffer with 1% Triton X-100, E) 60 min. in a 10-fold dilution in washing buffer of a previously described hybridoma supernatant P3F51, F) 3×5 min. in washing buffer, G) 60 min. in washing buffer with horseradish peroxidase linked-anti-mouse Ig whole antibodies from Amersham (NA.931) diluted 1:1000, H) 3×5 min. in washing buffer, I) 1 min. in 10 mM $Na_2HPO_4$, 10 mM citric acid, pH 5.0 (C/P buffer), and J) approximately 5 min. in a staining solution mixed immediately prior to use consisting of 80 mg dioctylsodiumsulfosuccinate (DONS), 24 mg 3,3',5,5'-tetramethylbenzidine. 10 ml ethanol, 30 ml C/P buffer and 20 μl $H_2O_2$. The enzyme reaction was terminated by incubation in 100 mg DONS in 12.5 ml ethanol and 37.5 ml $H_{20.}$ The following clones were found to be positive by this procedure: SPE 301, 308, 311, 312 and 315.

Western blot

The positive clones obtained in the screening procedure were further analyzed using the Western blot technique (ref. 32).

In the Western blot procedure, one ml overnight cultures were pelleted (6000×E for 5 min.) and resuspended in 0.5 M Tris-HCL, pH 6.8 3% SDS, 15% glycerol, 5% mercaptoethanol and bromophenol blue. The samples were boiled for 5 minutes prior to loading on a gel. Proteins were separated by sodium dodecylsulfate polyacrylamide gel electrophoresis (SDS-PAGE) (11), the separating gel consisting of 7% (w/v) acrylamide (acrylamide/bisacrylamide ratio of 4.0:1) in 0.4 M Tris, pH 6.8, 0.1% SDS, 0.05% glycerol.

Subsequent transfer to nitrocellulose filters was performed in a semi-dry electroblotter as described by Kyhse-Andersen (25). Further handling of the filters was as described above in the screening procedure.

The results appear from FIG. 3 which shows a Western blot of the 5 positive clones.

The transformant strains SPE 308 (lanes 2 and 3) and SPE 312 (lanes 5 and 6) harbouring the plasmids pSPE 308 and pSPE 312, respectively, were shown to be PMT-producing, whereas SPE 301, SPE 315 and SPE 311 were shown not to be. Purified PMT (lane 8) was used as control. The recombinant toxin produced by SPE 308 and SPE 312 shows the same properties as the native protein with respect to recognition in the competitive ELISA as described in Example 1; the size and the toxic activity in the EBL test (ref. 29) are unchanged.

EXAMPLE 6

Restriction mapping and localization of the PMT gene

The plasmids pSPE 308 and pSPE 312 were analyzed for recognition sequences for restriction enzymes (restriction sites), testing for restriction sites for most of the known enzymes with a 6 base pair (bp) recognition sequence. The results are shown in FIG. 4 (pPSPE 308) and FIG. 5 (pSPE 312). It appears from the figures that the two plasmids carry an approximately 6 kb overlap (from position 11000 to 7000 in pSPE308). The pmt gene is therefore localized within this area.

By constructing end-point deletions in the overlapping areas in pSPE 308 and pSPE 312 a number of plasmids. the pSPE 308 derivatives pSPE 336, pSPE 341, pSPE 344 and pSPE 350 as well as the pSPE 312 derivatives pSPE 338, pSPE 343, pSPE 345, pSPE 347/349 and pSPE 525 were constructed. The extents of the resulting plasmids are shown in FIGS. 6 and 7.

These plasmids were transformed to *E. coli* strain MT 102 and analyzed for the production of PMT by Western blotting as described above.

Figure 5:
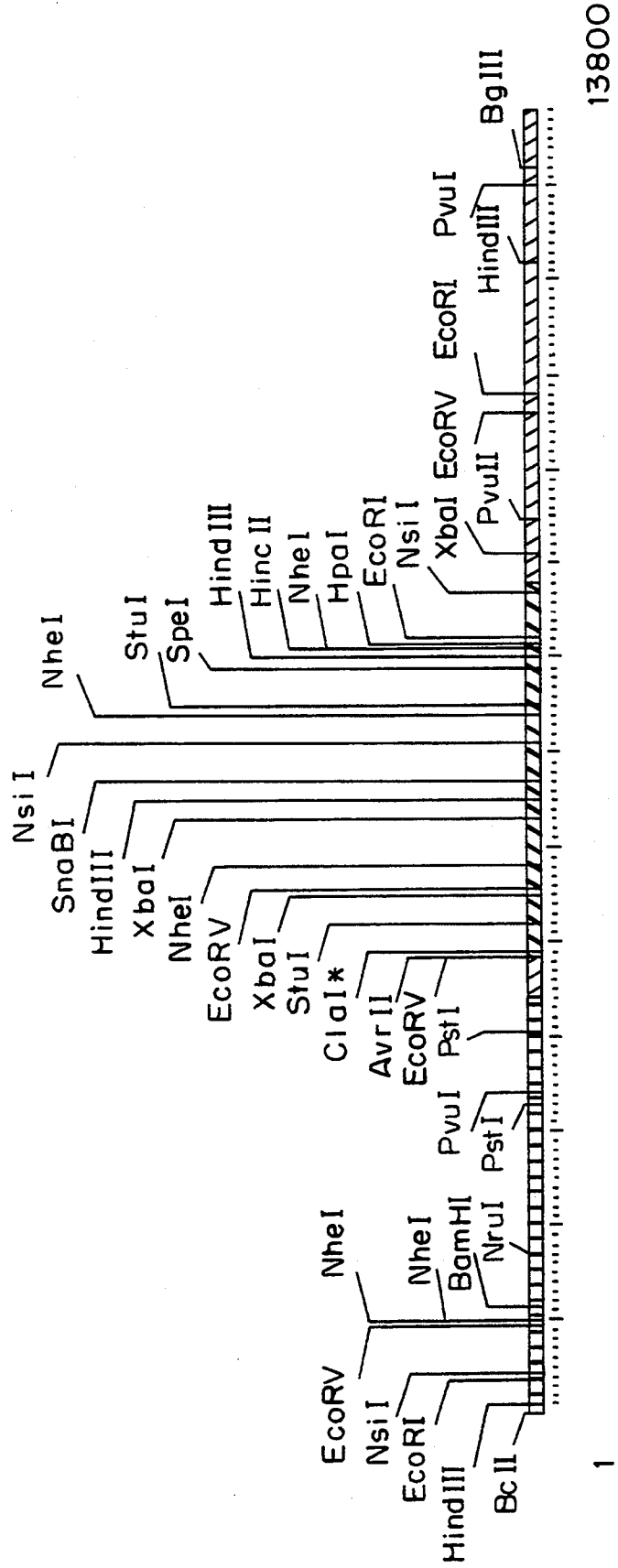
FIG. 5 is a restriction enzyme cleavage map of the plasmid pSPE 312 with a length of 13.8 kb. The hatched area denotes *P. multocida* DNA, the shaded area denotes the pmt gene and the vertically hatched area denotes plasmid pUN121 DNA.
Figure 6:
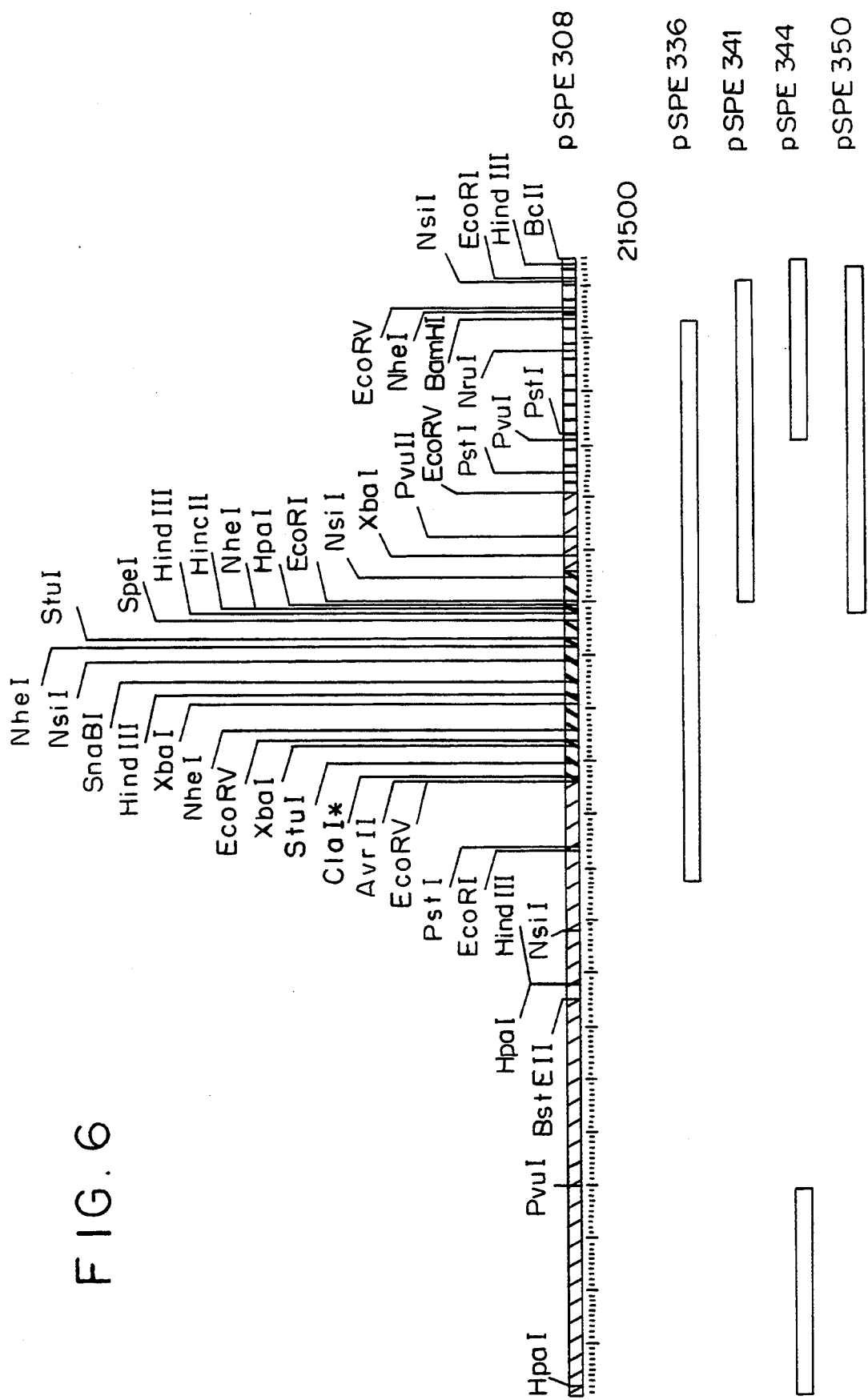
FIG. 6 is a restriction enzyme cleavage map of plasmids constructed by enzymatic cleavage of the plasmid pSPE 308. The hatched area denotes *P. multocida* DNA, the shaded area denotes the pmt gene, and the vertically hatched area denotes pUN121DNA.
Figure 7:
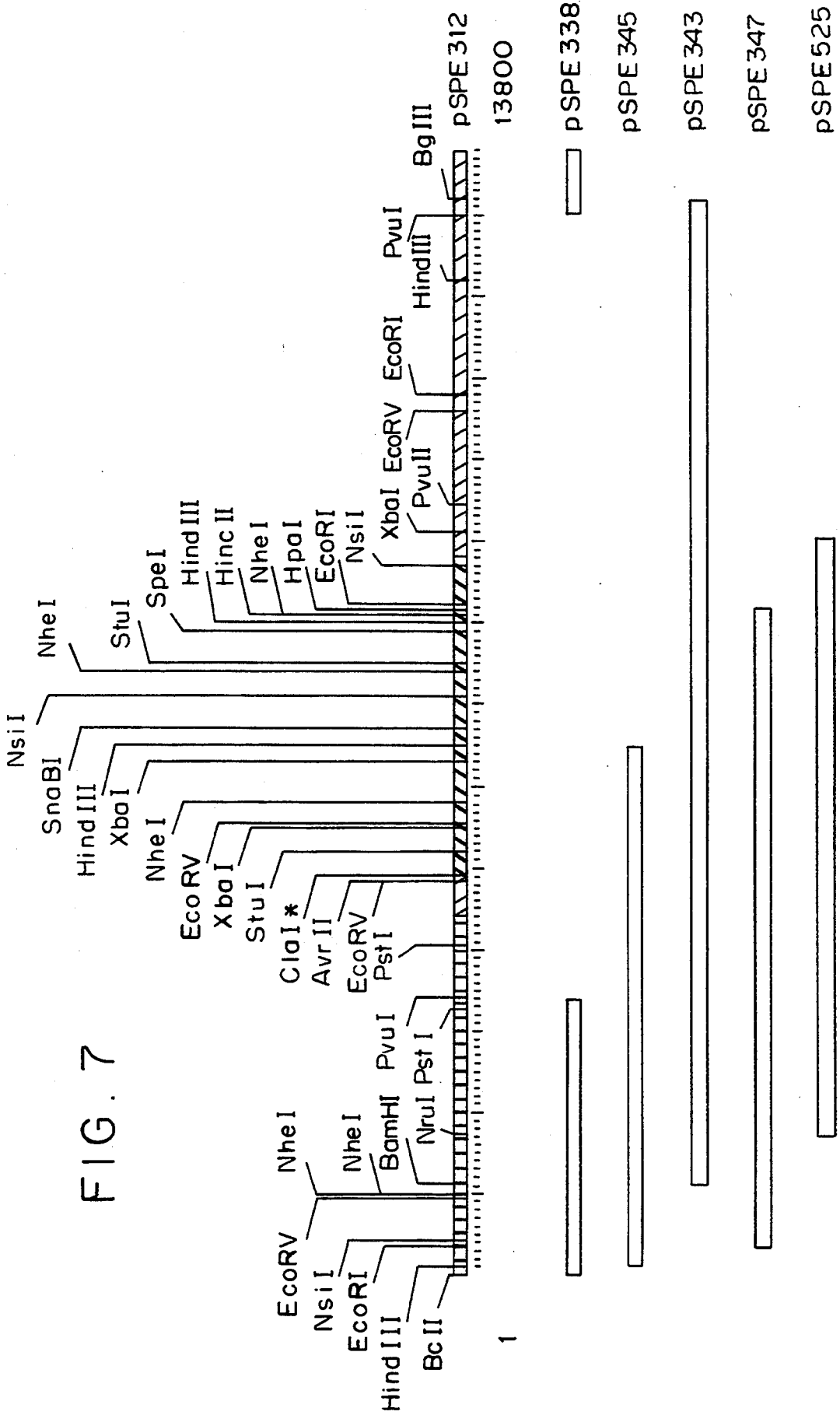
FIG. 7 is a restriction enzyme cleavage map of plasmids constructed by enzymatic cleavage of pSPE 312. The hatched area denotes *P. multocida* DNA, the vertically hatched area denotes pUN121 DNA, and the shaded area denotes the pmt gene.
Figure 8:
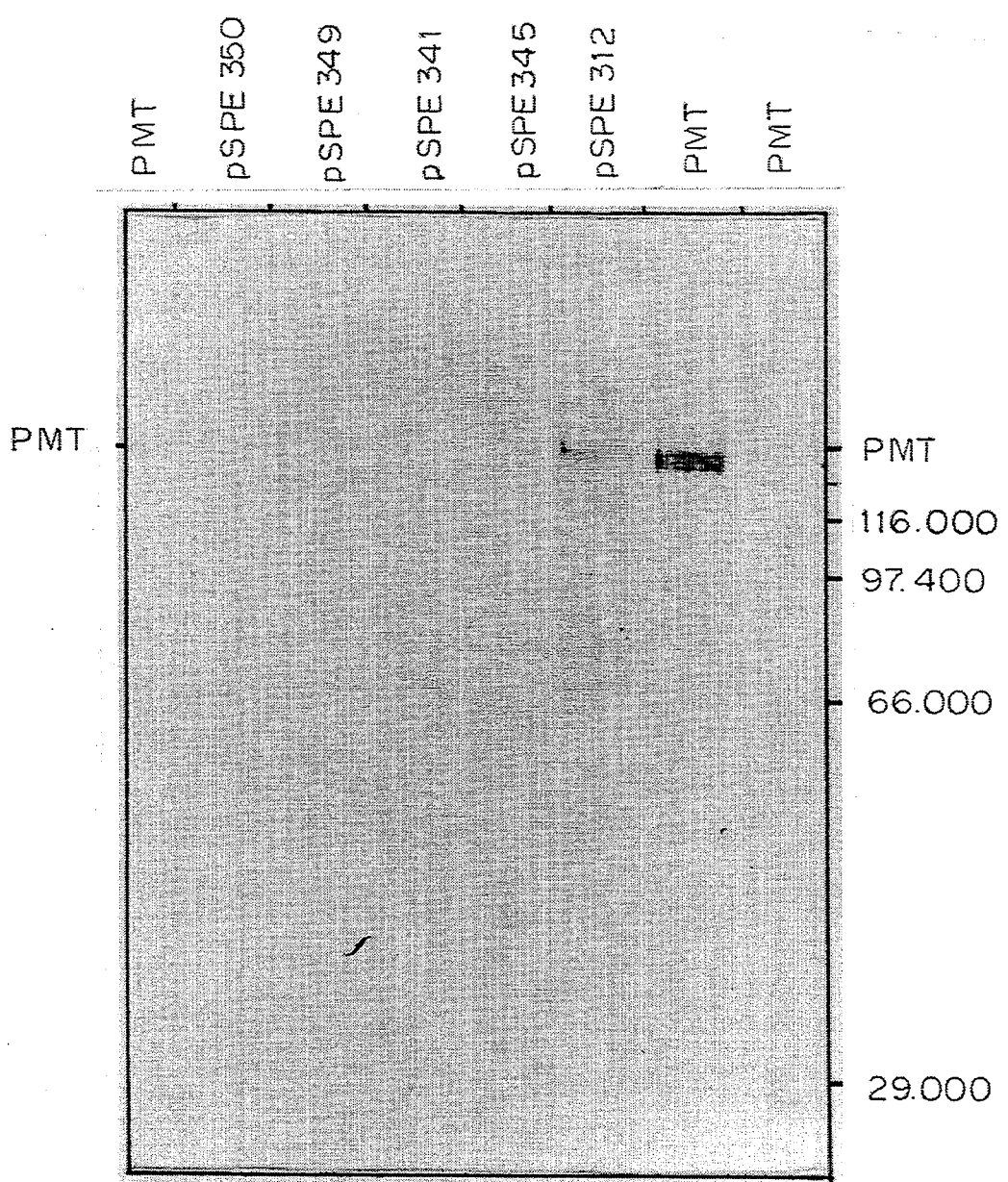
FIG. 8 is a Western blot showing PMT production by derivatives of plasmids pSPE 308 and pSPE 312. Lane 1: purified PMT; lane 2: pSPE 350; lane 3: pSPE 349; lane 4: pSPE 341; lane 5: pSPE 345; lane 6: pSPE 312; lanes 7 and 8: purified PMT. Plasmid pSPE 349 is identical to plasmid pSPE 347 shown in FIG. 7.
Figure 11:
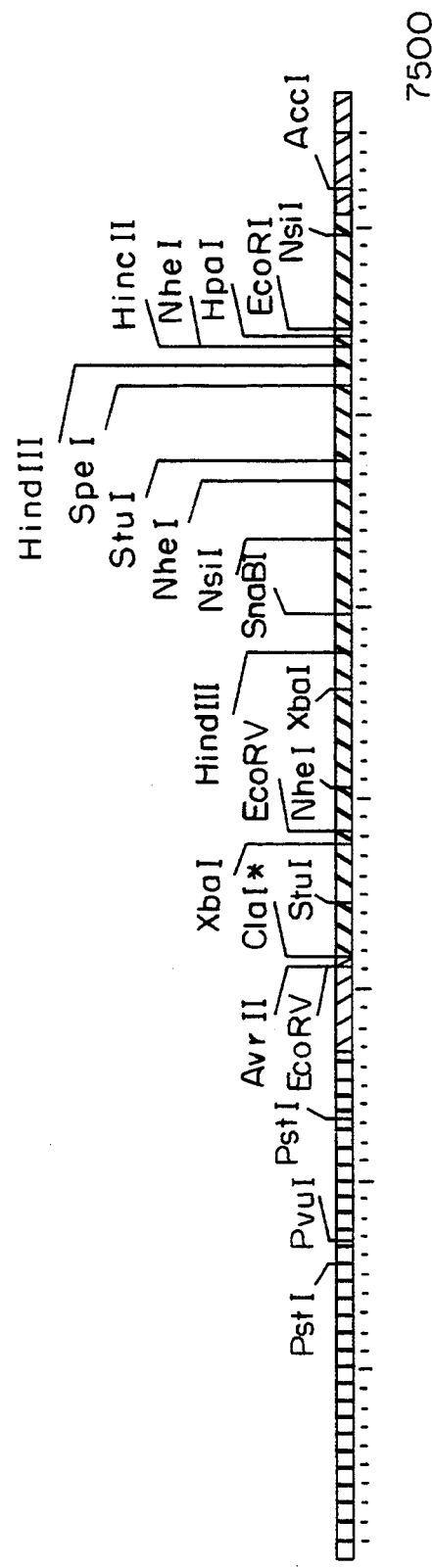
FIG. 11 is a restriction enzyme cleavage map of the plasmid pSPE 525 with a length of 7.7 kb. The hatched area denotes *P. multocida* DNA the shaded area denotes the pmt gene, and the vertically hatched area denotes pUN121DNA.
Figure 12:
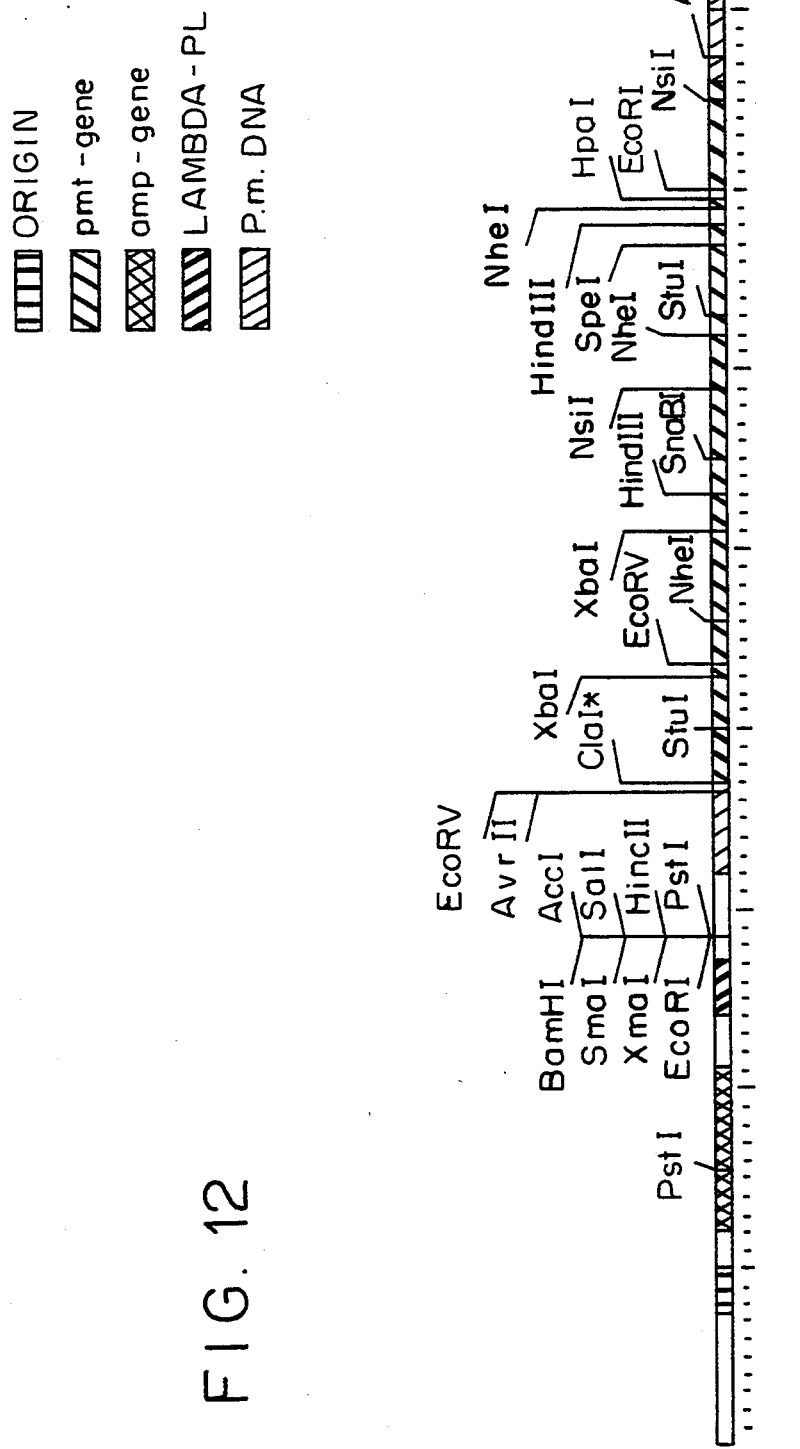
FIG. 12 is a restriction enzyme cleavage map of the expression vector pSPE 481 with a length of 8.25 kb. The hatched (towards the right) area denotes *P. multocida* DNA, the shaded area denotes the pmt gene, the hatched (towards the left) area denotes $\lambda P_L$ DNA the cross-hatched area denotes the amp gene, and the vertically hatched area denotes the origin of replication.

In the Western blot, a single protein with an apparent molecular weight of 125000 daltons was found. The blot is shown in FIG. 8. The plasmid pSPE 349 coding for this protein is deleted of a region to the right of the EcoR1 site at position 8200 in pSPE 312 (cf. FIG. 5 and 7). The gene product of plasmid pSPE 349 therefore localizes the position and orientation of the pmt gene (shown as shaded area in FIG. 5). The coding region begins about 3.3 kb upstream of the EcoR1 site at position 8200 in pSPE 312 i.e. around the ClaI site at position 4900. Since the total coding region is estimated to be about 3.9 kb the structural gene ends about position 8800 on the map shown in FIG. 5.

EXAMPLE 7

Sequencing of the pmt gene

The nucleotide sequence carrying the pmt gene as localized in Example 4 was determined using the method described by Sanger et al. (ref. 33). The sequence of 4381 consecutive bp were determined. The DNA sequence of the region is shown in FIG. 10 (*a*)-(*j*) (SEQ. ID. NO. 1) in which the deduced amino acid sequence (SEQ. ID. NO. 1) is indicated above the DNA sequence starting at position 219. The methionine codon of position 219–221 is preferred as a starting codon to the methionine codon of position 213–218 due to its perfect spacing to the putative ribosome binding site at position 201–210. The region containing the pmt gene was subjected to wore detailed restriction mapping by a computer search for all restriction sines for restriction enzymes with 6 bp recognition sequences.

The results are shown in FIG. 9 which shows a high degree of conformity with the previously constructed restriction map.

EXAMPLE 8

Figure 13:
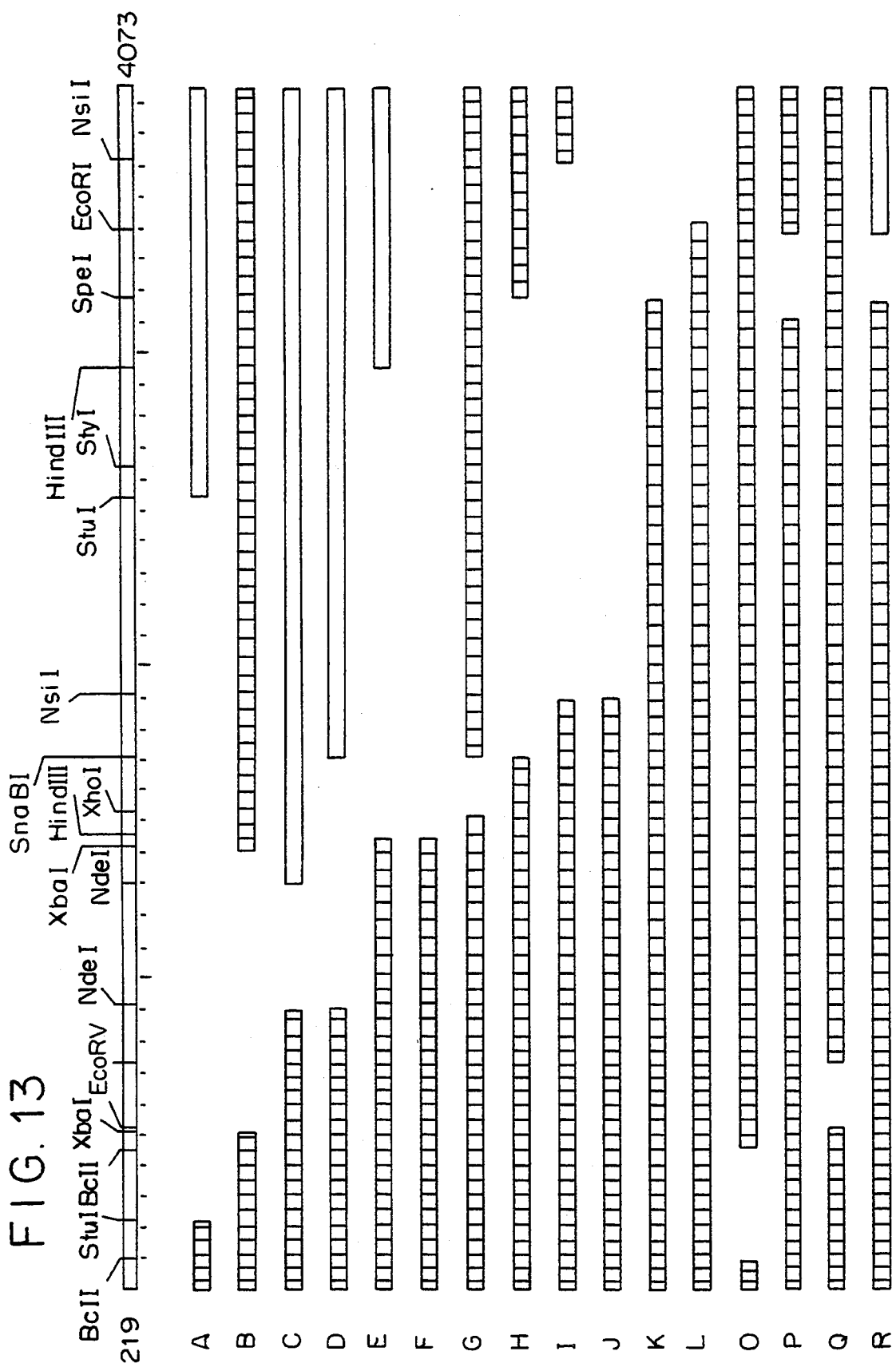
FIG. 13 is a restriction enzyme cleavage map of the toxA coding region. Extension of coding region present on each derivative plasmid (pSPE A-R) is indicated (A-R) by bars. Hatched bars: Coding region in correct reading frame; open bars: Coding region not in frame with the 5' part of the coding region.
Figure 14:
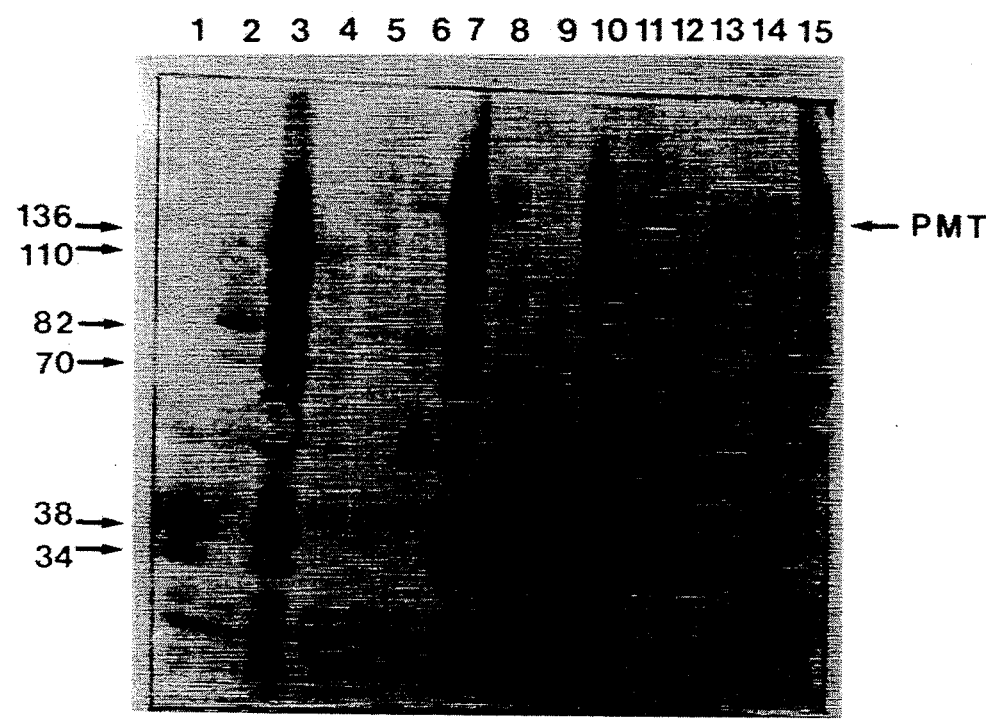
FIG. 14 is a Western blot showing the recognition by a mouse anti-PMT antiserum of PMT derivatives produced by the plasmids pSPE A-L. Lanes 7, 13, 14 and 15: different strains harbouring the entire pmt gene; lane 1: derivative A: lane 2: derivative I; lane 3: derivative B; lane 4: derivative J; lane 5: derivative L; lanes 6 and 9: derivative E; lane 8: derivative C; lane 10: derivative G; lane 11: derivative H; lane 12: derivative D. Approximate sizes (in kilodalton) of prominent full-length derivatives and degradation products are indicated.

Expression of *P. multocida* toxin in *E. coli*

The amount of PMT produced in different recombinant *E. coli* clones was determined by estimating the incorporation of S-35 labelled methionine using the following procedure. Cells were grown in AB minimal medium (ref. 22) supplemented with 0.2% glucose, 1 μg/ml thiamine and 50 μg/ml leucine at 37° C. At an optical density ($OD_{450}$) of 0.6, 1 μl of a 1 mCi/ml S-35 methionine solution (purchased from Amersham, SJ. 1015) was added to a 1 ml sample of the culture at 37° C. 3 minutes later, 50 μl of 10 mg/ml unlabelled methionine was added as a chase and after further 3 minutes, the sample was put on ice. Samples were pelleted (6000×g for 5 minutes) and resuspended in loading buffer (0.5SM Tris-HCl pH 6.8, 3% SDS, 15% glycerol, 5% mercaptoethanol, bromophenol blue). Subsequently, proteins were separated in SDS-PAGE as described in Example 5. Furthermore, the gel was dried and subjected to autoradiography overnight on a KODAK XAR-5 X-ray film. Relative amounts of PMT were estimated by scanning of the X-ray film, using the β and β' subunits of the *E. coli* RNA-polymerase as a reference.

Recombinant clones tested in this way were MT102 strains harbouring the plasmids pSPE 312, pSPE 525 (shown in FIG. 11) and pSPE 481 (shown in FIG. 12), respectively. Plasmid pSPE 481 consists of the kb PstI fragment of pSPE 525 ligated to a 1.3 kb PstI fragment of plasmid pPL 195, containing part of the ampicillin resistance gene and the lambda PL promoter and operator region. pPL 195 was constructed by inserting a pUC8 EcoRI-HindIII polylinker (ref. 33) into a EcoRI and HindIII restricted PLc28 vector (ref. 36). The resulting pSPE 481 plasmid carries the lambda PL promoter transcribing into pmt gene.

TABLE 4

| Estimated amount of PMT in the recombinant *E. coli* clones | | | |
|---|---|---|---|
| | SPE312 | SPE525 | SPE481 |
| molecules/cell | <500 | 3000–4000 | 12000–15000 |
| Data used in the above calculations | | | |
| | β | β' | PMT |
| Methionine content (%) | 2.76 (23) | 2.56 (24) | 2.80 |
| Size (kD) | 150 (23) | 155 (24) | 146.5 |
| Molecules/cell (at 2.5-3 doublings/hour) | 4500 (25) | 4500 (25) | |

Furthermore, the content of PMT in SPE481 was estimated using the following procedure. A 100 ml culture with an optical density ($OD_{450}$) of 5 was pelleted (6000×g for 5 minutes) and resuspended in 10 ml of 50 mM Tris-HCl pH 7.0. The supernatant, which did not contain any PMT, was discarded and the harvested cells were disrupted by sonication. PMT was then further purified on an anion-exchange column as described in ref. 6. The purified PMT was then subjected to a quantitative ELISA as described in Example 2, obtaining an estimated value of 2–5 μg PMT per ml of culture fluid.

The *Escherischia coli* K-12 strain MT102 harbouring the pSPE 481 plasmid has been deposited 21 Mar., 1988 according to the Budapest Treaty in Deutsche Sammlung von Mikroorganismen und Zellkulturen GmbH under the strain designation *Escherichia coli* K-12 SPE 481. The accession number is DSM 4488.

EXAMPLE 9

Production and characterization of toxin derivatives

The following derivatives of toxin-encoding plasmids were constructed with the purpose of producing truncated, i.e. detoxified, toxins which are potentially useful for immunogenic purposes. The constructions were prepared on the basis of the restriction mappings disclosed in Examples 6 and 7. The hypothetical toxin-derived proteins produced from plasmids pSPE A through pSPE Q, proteins A through R, are shown in FIG. 13. All derivatives were optimally expressed from the respective plasmids in strain SG 21059 kindly provided by Susan Gottesmann. The known genotype of this strain is Δgal 1on146:: ΔTn10 Δ1ac.

1) pSPE A. The plasmid was constructed by restricting pSPE 481 with the restriction enzyme StuI prior to ligation. This deletion causes a change of reading frame. However, as described below, a PMT derivative could be detected in Western blotting as well as in the EBL toxicity test. This could be due to a small amount of erroneous frame—shifting in the translation procedure. See FIG. 13.

2) pSPE B. The plasmid was constructed by restricting pSPE 481 with the restriction enzyme XbaI prior to ligation. The plasmid codes for a hypothetical PMT derivative of about 108 kD, lacking amino acids 169 through 468 of PMT. See FIG. 13.

3) pSPE C. The plasmid was constructed by restricting pSPE 481 with the restriction enzyme NdeI prior to ligation. This deletion causes a change of reading frame. However, as described below, a PMT derivative could be detected in small amounts. This could be due to erroneous frame-shifting in the translation procedure. See FIG. 13.

4) pSPE D. The plasmid was constructed by restricting pSPE 481 with the restriction enzymes NdeI and SnaBI and subsequently blunt-ending the resulting ends, using T4 polymerase (purchased from New England Biolabs) as described by the manufacturer, prior to ligation. This deletion causes a change of reading frame. However, as described below, a PMT derivative could be detected in small amounts. This could be due to erroneous frame-shirring in the translation procedure. See FIG. 13.

5) pSPE E. The plasmid was constructed by restricting pSPE 481 with the restriction enzyme HindIII prior to ligation. The plasmid codes for a hypothetical PMT derivative of about 53 kD, since this deletion causes a change of reading frame. See FIG. 13.

6) pSPE F. The plasmid was constructed by restricting pSPE 312 with the restriction enzyme HindIII prior to ligation. Like pSPE E, this plasmid codes for a hypothetical PMT derivative of about 53 kD. See FIG. 13.

7) pSPE G. The plasmid was constructed by restricting pSPE 481 with the restriction enzymes SnaBI and XhoI and subsequently blunt-ending the resulting ends as above, prior to ligation. The plasmid codes for a hypothetical PMT derivative of about 135 kD, lacking amino acids 507 through 568 of PMT. See FIG. 13.

8) pSPE H. The plasmid was constructed by restricting pSPE 481 with the restriction enzymes SnaBI and SpeI and subsequently blunt-ending the resulting ends as above, prior to ligation. The plasmid codes for a hypothetical PMT derivative of about 88 kD, lacking amino acids 569 through 1058 of PMT. See FIG. 13.

9) pSPE I. The plasmid was constructed by restricting pSPE 481 with the restriction enzyme NsiI prior to ligation. The plasmid codes for a hypothetical PMT derivative of about 79 kD, lacking amino acids 634 through 1204 of PMT. See FIG. 13.

10) pSPE J. The plasmid was constructed by restricting pSPE 312 with the restriction enzyme NsiI prior to ligation. The plasmid codes for a hypothetical PMT derivative of about 70 kD. See FIG. 13.

11) pSPE K. The plasmid was constructed by restricting pSPE 481 with the restriction enzyme SpeI and blunt-ending the resulting ends as above prior to ligation. The plasmid codes for a hypothetical PMT derivative of about 117 kD. See FIG. 13.

12) pSPE L. The plasmid was constructed by restricting pSPE 312 with the restriction enzyme EcoRI prior to ligation. The plasmid codes for a hypothetical PMT derivative of about 124 kD. See FIG. 13.

13) pSPE O. The plasmid was constructed by partially restricting non-methylated pSPE 481 with the restriction enzyme BclI prior to ligation. The plasmid codes for a hypothetical PMT derivative of 133 kD, lacking amino acids 30 through 150 of PMT. See FIG. 13.

14) pSPE P. The plasmid was constructed by restricting pSPE 481 with the restriction enzyme SpeI, subsequent treatment with the exonuclease Bal31, restriction with EcoRI and finally treatment with Klenow fragment of DNA polymerase I in the presence of all four deoxyribonucleotides prior to ligation. The plasmid codes for a hypothetical PMT derivative of about 136 kD, lacking amino acids 1043 through 1130 of PMT. See FIG. 13.

15) pSPE Q. The plasmid was constructed from a derivative of pSPE 481, pSPE 680. pSPE 680 was constructed by restricting pSPE 481 with the restriction enzymes BamHI and ClaI, and treatment with Klenow fragment of DNA polymerase I in the presence of all four deoxynucleotides prior to ligation. Subsequently, pSPE Q was constructed by restricting pSPE 680 with EcoRV prior to ligation. The plasmid codes for a hypothetical PMT derivative of 127 kD, lacking amino acids 175 through 246 of PMT.

16) pSPE R. The plasmid was constructed by restricting pSPE 481 with the restriction enzymes SpeI and EcoRI and blunt-ending the resulting ends, as described above, prior to ligation. The resulting plasmid codes for a hypothetical PMT derivative of about 117 kD, See FIG. 13.

The reactivity of selected derivatives with a panel of anti-PMT MAbs has been studied by sandwich ELISA's based on detection with non—competitive combination pairs of MAbs. By this method an antigen-code (Ag-code), i.e. a term indicating the epitope-difference of the derivative compared to PMT, was determined for each derivative.

The minimal cytopathic dose (MCD) on 120 $\mu$l of $1.5\times10^5$ embryonic bovine lung cells has been estimated for some affinity-purified PMT derivatives.

The results of the two studies are indicated in the following table (Table 5):

TABLE 5

| | Derivative | | | | | |
|---|---|---|---|---|---|---|
| | L | O | P | B* | C* | G* |
| Ag-code | PMT-$\alpha$ | PMT-$\beta$ | PMT-$\beta$ | PMT-$\gamma$ | PMT-$\gamma$ | PMT |
| MCD (ng) | 250 | 30000 | 5 | n.d. | n.d. | n.d. |

*not affinity-purified (sonicates)
n.d.: not done

The antigen-code "PMT" indicates that the derivative reacts indifferently compared to PMT by the sandwich-ELISA, i.e. all epitopes characterized by the panel of MAbs, which are present on PMT can be detected on the derivative The Ag-code "PMT-x", where x is $\alpha$, $\beta$ or $\gamma$ indicates that the MAb(s) reacting with epitope x on PMT are not reacting with the derivative. The results of these tests shows that epitope $\alpha$ is missing on derivative L, $\beta$ is missing on O and P and $\gamma$ is missing on B and C.

The MCD of PMT is approx. 0.01–0.03 ng and it is therefore obvious that the abovementioned derivatives L and O are practically non-cytopathic compared to PMT, whereas P shows slightly remaining cytopathic activity.

A Western blot was made using a mouse anti-PMT antiserum produced described in Example 1, and using horseradish perioxidase rabbit anti-mouse Ig whole antibody (purchased from Amersham) as the secondary antibody. Strains harbouring the plasmids pSPE A, B, C, D, E, G, H, I and L were shown to react with the anti-PMT antiserum (cf. FIG. 14).

Trials carried our on mice for elucidation of the immunogenic effect of the O-derivative Purpose To study the immunogenic effect of PMT after deletion in the N-terminal end (O-derivative).

Method
For the trials, BALB/c mice were used. Sexually against PMT and are protected against even high concentrations of PMT.

TABLE 6

SCHEME OF VACCINATION TRIALS WITH O-FRAGMENT IN MICE (ADULT)

| Trial | x, (s) (in titer) | CONC. (vaccine) | Amount of PMT (challenge) | | | | | | |
|---|---|---|---|---|---|---|---|---|---|
| | | | 200 ng | 250 ng | 800 ng | 3200 ng | 4000 ng | 8000 ng | 16000 ng |
| 1 | 6.49 (0.60) | 5 µg/ml | 0/2* | | 0/4 | 0/4 | | | |
| 2 | 1.27 (1.06) | 5 µg/ml | | | | | 1/3 | 3/4 | 4/4 |
| 3 | 1.06 (1.10) | 2.5 µg/ml | | 1/2 | | | 2/4 | | 3/4 |

*Number of dead mice/number of i.p. injected mice mature female mice were immunized subcutaneously 2 times at 14 days interval with 0.3 m O-derivative (2.5–5 µg/ml) in 20% $Al$hydrogel (cf. Example 12) in PBS+0.1% zero-mouse-serum.

Simultaneously with the 1st vaccination the female mice were mated. Thus, the 2nd vaccination took place about 1 week before expected birth.

1) About 10 days old the baby mice were divided into 2 groups. Half of them were dripped intranasally with PMT (totally 60 ng PMT), the other half was injected intraperitoneally (i.p.) with PMT in different concentrations. The number of dead animals was recorded.
2) All the adult female mice were bled after killing of the surviving baby mice. The blood samples were analysed by ELISA as described in Example 13 for the presence of antibodies against PMT. Immediately after blood sampling the mice were injected i.p. with different concentrations of PMT. The number of dead animals was recorded.

| | Schematic trial plan |
|---|---|
| Trial week No. | |
| 3 | 31 female BALB/c mice were mated and subsequently immunized with O-derivative |
| 2 | |
| 1 | 31 female BALB/c mice were immunized for the second time with O-derivative |
| 0 | 31 female mice delivered 122 baby mice |
| 1 | the baby mice were divided into group I (61) which was treated intranasally with PMT. Group II (61) which was treated i.p. with PMT |
| 2 | surviving baby mice were killed female BALB/c mice were bled female BALB/c mice were injected i.p. with PMT |
| 3 | the number of surviving female BALB/c mice was recorded and the animals killed Trial finished |

Results are shogun in tables 6 and 7.

$LD_{75}$ in non-protected baby mice was about 20 ng PMT injected i.p. $LD_{50}$ in non-protected adult mice was about 70 ng PMT injected i.p.

Conclusion

It can be concluded that mice born from mothers vaccinated with O-derivative vaccine in the doses described can survive i.p. injection of min. $25 \times LD_{50}$ of PMT. The protection is obtained via antibodies transferred via colostrum from mother to offspring.

Furthermore it can be concluded that O-derivative vaccinated animals develop antibodies against PMT, even if some variation is seen. The mice can survive i.p. injection of min. $50 \times LD_{50}$ of PMT.

Thus, mice vaccinated with O-derivative can transfer a considerable protection against PMT to the offspring via colostrum. The mice themselves develop antibodies

TABLE 7

SCHEME OF TRIAL WITH O-FRAGMENT IN MICE (OFFSPRING)

| Trial | Amount of PMT (challenge) | | | | | |
|---|---|---|---|---|---|---|
| | 20 ng | 30 ng | 100 ng | 150 ng | 500 ng | 750 ng |
| 1 | 0/4* | | 0/7 | | 0/7 | |
| 2 | | 0/9 | | 0/10 | | 8/8 |
| 3 | | 0/1 | | 0/10 | | 4/5 |

*Number of dead mice/number of i.p. injected mice

EXAMPLE 10

Differentiation of PMT+ and PMT− strains by PMT-ELISA 615 field isolates and 7 reference strains of *P. multocida* were examined. The field isolates were obtained from nasal swabs (603 isolates) and lungs (12 isolates) of pigs from 156 Danish herds and were identified by the following criteria: acid produced from glucose. saccharose, mannitol, sorbitol and not from maltose, arabinose, dulcitol and inositol; and production of indole, ornithine decarboxylase, catalase, oxidase and not of urease.

Extracts for toxin analyses were prepared by harvesting blood agar (9 cm Petri dish) overnight (37° C.) cultures into 2 ml of sterile water by means of a spatula. The suspensions were left for extraction at 37° C. for approximately 18 hours. One part of the extract was examined directly by PMT-ELISA as described in Example 2. All absorbances (A) were expressed as percentages of the absorbance obtained by a positive control ($A_O$). This control was a 1:1 dilution of an extract, freshly prepared for each test of the toxigenic type D reference strain *P. multocida ssp. multocida* 45/78.

Another part was-centrifuged (30 min. at $1500 \times g$), the supernatant sterile filtered and subsequently examined in the EEL-cell test as described earlier refs. 22 and 29).

The 615 field isolates were characterized as toxigenic (250) or non-toxigenic (365) by the F, EBL-cell test and were of capsular type A (119 toxigenic and 92 non-toxigenic isolates) or D (131 toxigenic and 273 non-toxigenic isolates).

Full agreement between the EEL-cell test and the PMT-ELISA was obtained for the 615 field isolates and the 7 reference strains (Table 8).

TABLE 8

| | EBL-cell-test a) | PMT-ELISA b) |
|---|---|---|
| 250 field isolates of *P. multocida ssp. multocida* | + | + |
| 365 field isolates of *P. multocida ssp. multocida* | − | − |

TABLE 8-continued

|  | EBL-cell-test a) | PMT-ELISA b) |
|---|---|---|
| Type strain (CCUG 17977) | − | − |
| P. multocida ssp. septica | | |
| Type strain (NCTC. 10204) | − | − |
| P. multocida ssp. galicida | | |
| Type strain (NCTC 10322) | − | − |
| P. multocida ssp. multocida, type A | | |
| Reference strain (ATCC 12945) | − | − |
| P. multocida ssp. multocida, type A | | |
| Reference strain (NCTC 12177) | + | + |
| P. multocida ssp. multocida, type A | | |
| Reference strain (ATCC 7707) | − | − |
| P. multocida ssp. multocida, type D | | |
| Reference strain (NCTC 12178) | + | + |
| P. multocida ssp. multocida, type D | | | a) All EBL-positive (+) bacterial extracts had EBL-titres above $10^3$ (median $10^4$, range $10^3$-$10^6$), in the EBL-cell test, EBL-negative (−) extracts were non-cytopathic.
b) All 1:1 diluted ELISA-positive (+) bacterial extracts had relative absorbances above 39% (mean ± SD: 94% ± 13%) in the PMT-ELISA, whereas all ELISA-negative (−) extracts had relative absorbances below 9% (2.1% ± 1.9%).

Figure 15:
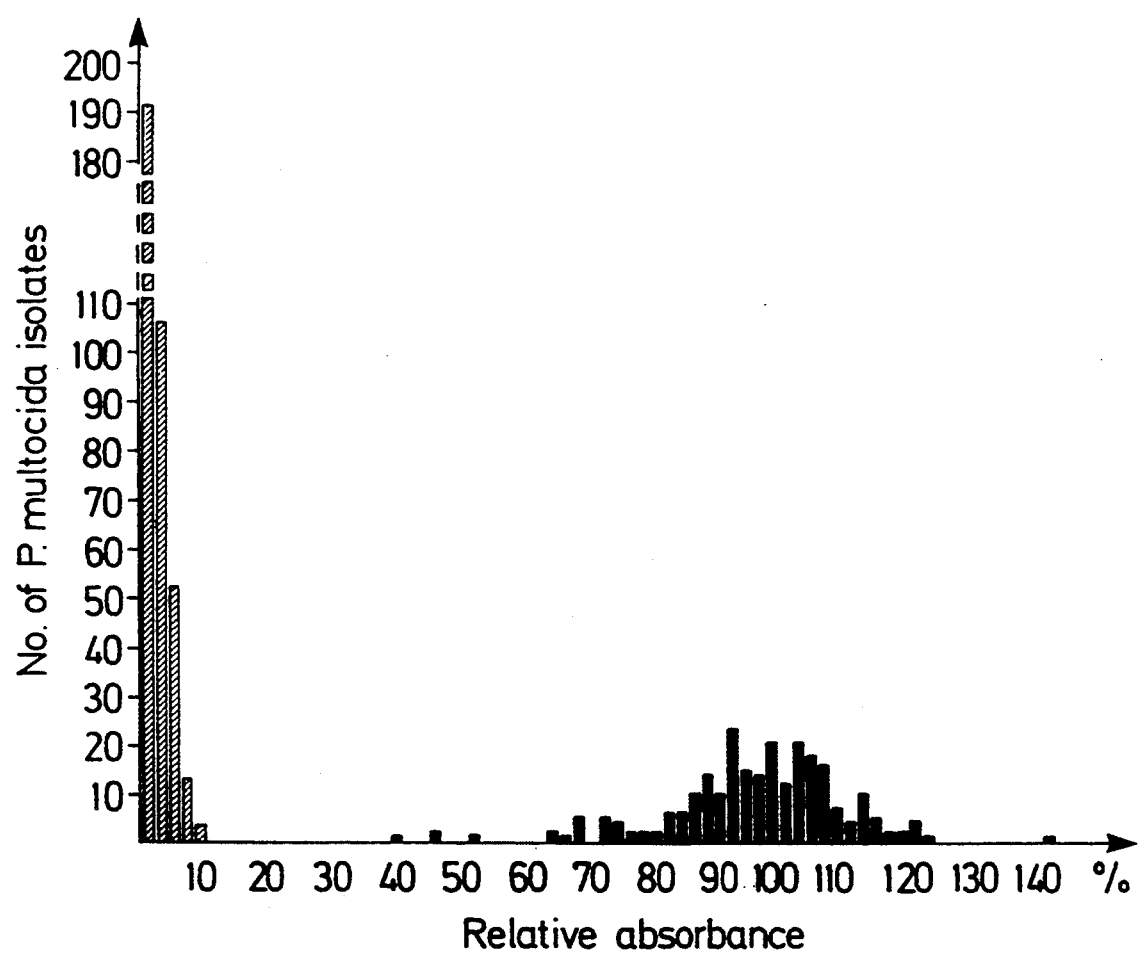
FIG. 15 is a graph showing the distribution of relative absorbances $(A/A_o)$ by PMT-ELISA of extracts of non-cytopathic (hatched bars) and cytopathic (black bars) field isolates of *P. multocida* diluted 1:1 in PBS-T-BSA.
Figure 16:
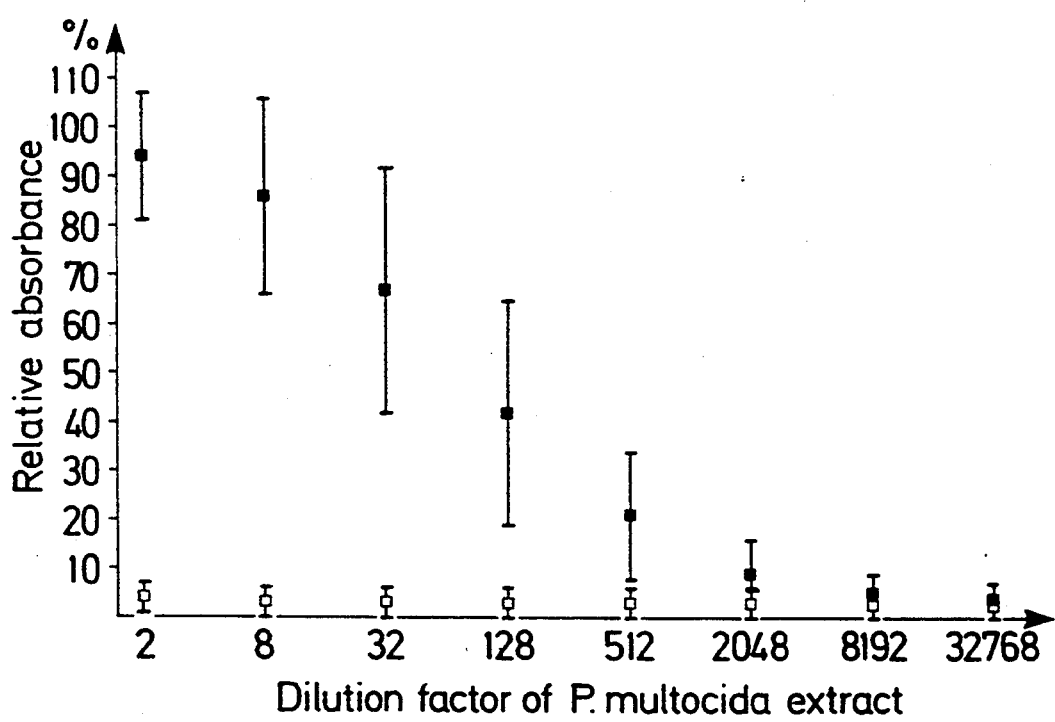
FIG. 16 is a graph showing the mean $\pm$SD of relative absorbances $(A/A_o)$ of dilutions of extracts of cytopathic (black squares) and non-cytopathic (open squares) field isolates of *P. multocida*.

The cytopathic and non-cytopathic extracts of the 615 field isolates were separated in two clearly distinguishable groups by the PMT-ELISA (FIG. 15). Since the means ± SD of the absorbances (A) obtained from the 1:1 diluted extracts of the 250 toxigenic isolates was 172±0.48, visual readings instead of photometric measurements of the ELI-SA-results would be satisfactory for the differentiation of extracts of P. multocida. The mean ± SD of the PMT-concentration in the extracts of the toxigenic isolates of P. multocida was estimated being 2.8±1.9 μg/ml, and since the detection limit of the PMT-ELISA is approx. 50 pg (1 ng/ml) PMT (cf. Example 2), dilutions of the extracts (FIG. 16) and extracts with low PMT-concentrations may appropriately be tested by PMT-ELISA. The main advantages of the PMT-ELISA compared to existing tests are the independence of cell culture or laboratory animal facilities, the ability of a single laboratory worker to handle several hundreds of samples per day and the possibility of obtaining quantitative objective results from bacterial extracts in 4 hours.

EXAMPLE 11

Neutralization of PMT which monoclonal anti-PMT-antibodies

Samples (30 μl) of either PMT in PBS or PMT in a crude cell-free extract of P. multocida 45/78 (ref. 6) containing PMT in amounts up 12 ng and 1 μg of purified MAb (P3F51) were incubated for 15 min. at 20° C. before application to embryonic bovine lung (EBL) cells (120 μl 1.5×10⁵ cells/ml) as described for the original EBL-cell test (ref. 29). The minimal cytopathic dose (MCD) of PMT was estimated when no MAb was present in the sample. The neutralization titer was recorded as the number of MCD which could be neutralized by 1 μg of MAb.

The results appear from Table 9 below.

TABLE 9

| Hybridoma group No. | Representative MAb | Neutralization in EBL-cell test (× MCD)$^a$ |
|---|---|---|
| 1 | P3F51 | 130 |
| 2 | P3F64 | 70 |
| 3 | P3F37 | <2 |
| 4 | P4F58 | 30 |
| 5 | P3F22 | 40 |
| 6 | P4F46 | 100 |
| 7 | P4F38 | 35 |

TABLE 9-continued

| Hybridoma group No. | Representative MAb | Neutralization in EBL-cell test (× MCD)$^a$ |
|---|---|---|
| 8 | P4F55 | 40 |
| 9 | P3F50 | 400 |
| 10 | P3F53 | 55 |

$^a$Neutralization of the cytopathic effect on PMT was estimated as the number of minimal cytopathic doses (MCD) neutralized by 1 μg of MAb. The MCD of PMT is about 30 pg.

As indicated in Table 9, addition of 1 μg of Mab to PMT 15 min. before addition to the EBL-cells resulted in a 30 to 400 times increase of the MCD for 9 out of the 10 representative Mabs, whereas Mab P3F37 had a very low neutralizing effect on PMT. The neutralization of the cytopathic effect of PMT was also achieved when a crude cell-free extract of P. multocida 45/78 was used instead of pure PMT.

Samples (200 μl) containing PMT in variable amounts up to 2.56 μg and purified Mab (P3F51) in amounts between 0.15 and 15 μg were incubated for 15 min. at 20° C. and injected intraperitoneally (i.p.) in female BALB/c mice (6 weeks old, 15 to 20 g). Mice dying within a week from the time of PMT injection were recorded and the lethal dose of PMT and the neutralizing effect of the MAb was estimated. When 1.5 or 15 μg of P3F51 were added the lethal dose of PMT increased about 4 and 32 times, respectively, whereas 0.15 μg of the MAb had no neutralizing effect.

To study the in vivo neutralization ability of anti-PMT monoclonal antibodies a 200 μl solution containing 15 μg of purified monoclonal antibody (P3F51) was injected (i.p.) in female BALB/c mice (6 weeks old, 15-20 g) 2 days before i.p. administration of a 200 μl solution containing PMT in varying amounts up to 2.56 μg either in a pure form or as a crude cell-free extract of P. multocida 45/78 (ref. 6). The neutralizing effect was estimated as described above.

The lethal dose of PMT increased about 32 times when mice were passively immunized with 15 μg of P3F51 2 days before challenge with PMT or a crude cell-free extract of P. multocida 45/78.

EXAMPLE 12

Vaccination with purified PMT or derivative O 15 mg of PMT purified as described in Example 3 in 45 ml of PBS was dialyzed against 0.35% formaldehyde in PBS, pH 7.3-7.9, for 36 hours at 4° C. after which 1 g/l lysine-HCl was added to the dialysis liquid, and after 18 hours the dialysis was continued with repeated changes of PBS. The thus produced detoxified PMT was analyzed for lack of (or sufficiently reduced) toxic activity in the mouse lethality test and the cytopathic test on EBL-cells described above as well as a dermonecrotic test in guinea pigs as described by Foged et al. (1).

10 mg of biologically inactive (detoxified) PMT in 40 ml PBS was then coupled to 10 ml aluminium hydroxide gel purchased from Superfos. Denmark, under the trade name Alhydrogel as recommended by the manufacturer and diluted in 20% aluminium hydroxide in PBS to a final concentration of about 5 μg/ml or 125 μg/ml detoxified PMT.

Gestating gilts were immunized subcutaneously 4–6 weeks and 2–3 weeks before farrowing with a dose of 3 ml of the detoxified PMT vaccine composition prepared above, After farrowing piglets were inoculated intranasally with *Bordetella bronchiseptica* and *P. multocida* as described in ref. 1 and the protective effect of the immunization of the sows was estimated by measuring the average daily weight gain before slaughtering of the pigs (at about 90 kg live weight) and determination of osteopathological conditions in the snout of the pigs at slaughtering. Pigs from immunized sows were compared to pigs from non-immunized sows and the protective effect of the immunization is shown in Table 10.

TABLE 10

|  | No. of animals (litters) | Mean daily weight gain after weaning | No. of animals with severe turbinate atrophy (%) |
|---|---|---|---|
| Pigs from non-immunized sows | 61 (8) | 781 g | 49 (80.3%) |
| Pigs from immunized sows | 174 (20) | 848 g | 20 (11.5%) |

In a study still in progress gilts were immunized with 50 μg/dose of affinity-purified derivative O from sonicates of an *E.coli* clone containing pSPE O as described in Example 9. No modifications of O were performed except for coupling to Alhydrogel. Preliminary results of the vaccination study indicates that:

a) the serum- and colostrum titres against native PMT are similar for gilts vaccinated with derivate O and formaldehyde treated PMT,
b) the specific antibodies are transferred to piglets through colostrum equally well in both vaccine groups.
c) the clinical symptoms of atrophic rhinitis are prevented equally well in the progeny from gilts vaccinated with O (O-piglets) and formaldehyde treated PMT (P-piglets), and that this prevention seems to be close to 100%, when compared to piglets born by unvaccinated gilts (control piglets).
d) the toxigenic *P. multocida* used for the experimental infection can be reisolated in significantly higher rates from control piglets than from O- or P-piglets at 5 weeks of age.

EXAMPLE 13

Detection of anri-PMT-antibodies

Figure 17:
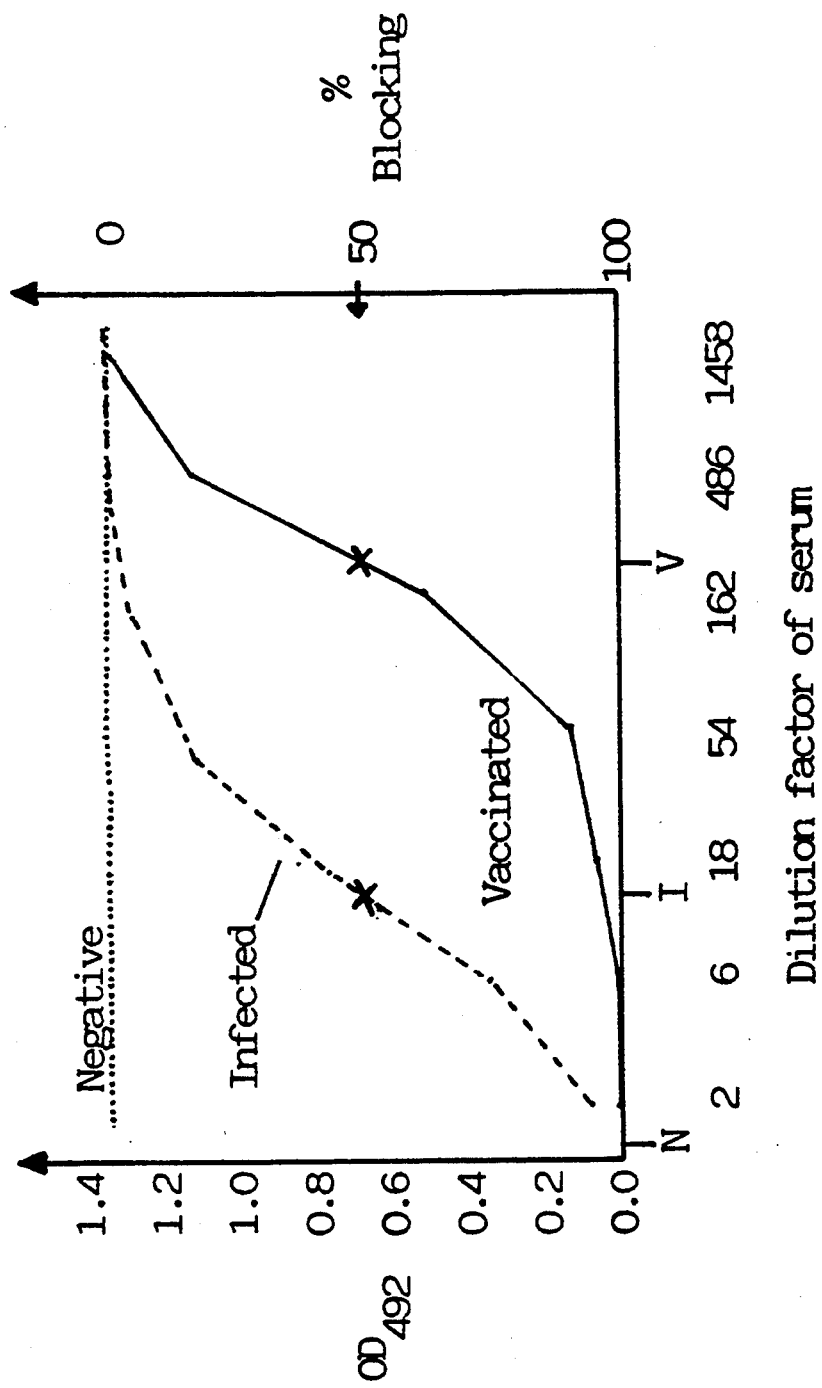
FIG. 17 is a graph showing the presence of anti-PMT-antibodies in serum samples from anti-PMT-antibody-negative, infected and vaccinated pigs detected by competive ELISA. The graph shows the 50% blocking titers at an absorbance of 492 nm.

By proceeding substantially as described in Example 2, but by incubating the coating monoclonal anti-PMT-antibody with a premixed preparation of serum and a constant amount of PMT, it is possible to detect anti-PMT-antibodies in serum of for instance pigs infected with *P. multocida* or of animals vaccinated with a vaccine of the invention. The mixture which was prepared for concentrated or diluted serum samples was incubated for 30 min. at 37° C. before incubation for 15 min. in the microtiter plate. The presence of anti-PMT-antibodies in the serum sample was detected by a decrease in absorbance measured substantially as described in Example 1 (the section entitled "ELISA for estimating epitope specificity"). The results are shown in FIG. 17 which shows the 50% blocking titers of serum from an anti-PMT-antibody negative pig (<2), a pig infected with a toxin-producing *P. multocida* strain (about 14) and a gilt vaccinated with the vaccine described in Example 12 (about 250).

EXAMPLE 14

Detection of PMT by colony blot and immunoblotting

The presence of PMT in samples may be detected by a colony blot method (ref. 14) as described in Example 5 (the section entitled "Screening procedure").

Similarly, the presence of PMT in samples may be detected by separating proteins in the samples electrophoretically by SDS-PAGE (as described in Example 1) and transferring them electrophoretically to a nitrocellulose membrane where PMT, if present, can be visualized by immunoblotting as described in Example 1 (in the section entitled "Immunoblotting"). The electrophoretic location of the stained protein band also gives the apparent molecular weights of PMT (approximately 143 kd).

EXAMPLE 15

Generic distinction between PMT+ and PMT- isolates of *P. multocida* as determined by colony hybridization

*P. multocida* isolates (17 toxin-positive and 18 toxin-negative strains as determined by ELISA and EBL tests as described above) were inoculated on Tryptic Soy Broth Agar plates (purchased from DIFCO). After incubation overnight at 37° C., a replica was made on a nitrocellulose membrane filter (Schleicher & Schull BA 85). This replica was placed (face up) on top of 4 consecutive Whatman 3MM filters which were soaked in 10% SDS, denaturation buffer (0.5M NaOH, 1.5 NaCl), neutralization buffer (0.5M Tris-MC1 pH 8.0, 1.5M NaCl) and 2×SSPE (360 mM NaCl, 20 mM NaH$_2$PO$_4$, 2 mM EDTA pH 7.4), respectively. Incubation was carried out for 5 minutes on each filter at room temperature. Subsequently, the nitrocellulose filter was dried and DNA was fixed to the filter by baking at 80° C. for 2 hours. Prehybridization and hybridizations were done in 6×SSC (0.15M NatCl, 0.015M sodium titrate, pH 7), 0.5% SDS and 5×Denhardt solution for 2 hours and overnight, respectively, at 65° C. The probe was a radioactively labelled XbaI fragment from position 1623 to 4376 in the sequence shown in FIG. 10 (*a*)–(*j*) prepared by the nick translation method (ref. 22). After hybridization the filter was washed at 25° C. in 2×SSC, 0.5% SDS for 2×15 min. and in 0.2×SSC, 0.5% SDS for 2×1 hour at 65° C. and left for autoradiography overnight.

The results appear from FIG. 18 which shows chat colonies at positions 5, 6, 8, 9, 10, 12, 13, 14, 15, 17, 19, 22, 34, 36, 37, 39, 45 and 50 were PMT+ and colonies at positions 7, 23, 24, 26, 28, 30, 32, 42, 44, 47, 48, 53, 56, 58, 63, 66, 73 and 75 were PMT−. These results are in accordance with the ELISA and EBL determinations. Hence, non-toxigenic strains of *P. multocida* owe their lack of toxin production to a lack of the PMT encoding pmt gene.

EXAMPLE 16

Purification of rPMT and comparison of rPMT with PMT

In the toxin purification procedure, cells harvested from a 1 l overnight stationary culture of SPE312 were resuspended in 10 ml of H$_2$O and sonicated several times for 0.5 min. at 0° C. using a Branson sonifier 250 (Branson, Conn., U.S.A.). The sonicate was diluted to 50 ml in 0.1M Tris-HCl, pH 7.8 containing 0.5 M NaCl before appliation to the affinity column which was prepared by immobilizing the anti-PMT Mab P3F5F51 as described in Example 3. After repeated washings of the affinity column, rPMT was eluted with 0.1M glycin-HCl, pH 2.8 as earlier described for the affinity purification of PMT from extracts of toxigenic *P. multocida*. All fractions were immediately neutralized with 1 M $K_2HPO_4$.

A diluted bacterial sonicate of SPE312 containing approximately 82 μg of rPMT as determined by the quantitative ELISA described in Example 2 was applied to a 1-ml affinity column to which was coupled approximately 5 mg of anti-PMT MAb P3F51. No rPMT could be detected in the effluent from the column. Upon elution approximately 75 μg of rPMT was obtained in the two main fractions of 1.4 ml each. This corresponds to a recovery of 91% of the applied rPMT.

PMT assays

Quantification of rPMT was done as described for PMT (Example 2) using the capture anti-PMT MAb P3F51 and the biotinylated detector MAb P3F37 in the PMT-ELISA, a sandwich ELISA based on the same technique as explained below for the study of epitopes on rPMT and PMT. Quantification by the PMT-ELISA was compared to results obtained in a modified Coomassie brilliant blue dye-binding microassay previously used for the determinations of protein concentrations and dye-binding ability of PMT compared to bovine serum albumine (BSA).

Comparison of epitopes on rPMT and PMT was done by sandwich ELISA's based on 10 anti-PMT MAbs (Example 1) purified from hybridoma supernatants on protein A-agarose columns. These MAbs have been shown to react with different epitopes on PMT. The sandwich-ELISA's were done as described in Example 2. Dual determinations were performed for both antigens in all 100 combinations of the 10 catching MAbs and the same biotinylated detecting MAbs. Combination pairs of MAbs resulting in absorbances below 0.3 were considered competitive. For the non-competitive combination pairs, the results were described as the mean of dual determinations of absorbance obtained for rPMT relative to the mean of dual determinations of absorbance for PMT.

The dermonecrotic and lethal effects of rPMT and PMT were determined by injecting 200 μl of dilutions of the previously ELISA-quantified samples intradermally into guinea pigs or intraperitoneally into BALB/c mice, respectively. Samples resulting in a dermal lesion of 10 mm or more at 48 h after intradermal injection were scored as dermonecrotic and samples resulting in death in less than 5 days after intraperitoneal injection were scored as lethal. All results were based on at least duplicate determinations.

Affinity-purified rPMT and PMT had very similar patterns of reactions in the structural ELISA test based on 100 combination pairs of 10 different anti-PMT MAbs and 100 ng/ml of affinity purified antigen. For PMT 25 pairs resulted in an absorbance value ($A_{492}$) below 0.3 which was considered to indicate competitiveness. The same 25 pairs showed competitive reactions when the antigen was 100 ng/ml rPMT. The remaining 75 non-competitive combination pairs resulted in $A_{492}$ values above 0.3 both when PMT and rPMT was used. The overall mean ± SD for the 75 calculated values of the relative absorbances of rPMT compared to PMT was 112%±8%. Only minor differences from the overall mean were observed for the mean values for the 10 catching MAbs and the 10 biotinylated detector MAbs.

PMT and rPMT reacted very similarly when tested for cytopathic effect on EBL-cells, for dermonecrotic activity in guinea pigs, and for lethality in mice, and their ability to bind Coomassie brilliant blue were equal and approximately 2.5 times weaker than the dye-binding ability of BSA (Table 11).

TABLE 11

| | Cytopathic, dermonecrotic, lethal and dye-binding effects of PMT and rPMT | | | |
|---|---|---|---|---|
| Sample | minimal cytopathic dose (pg) | minimal dermonecrotic dose (ng) | minimal lethal dose (ng) | dye-binding (%)[a] |
| PMT | 20–40 | 15–45 | 25–50 | 40–45 |
| rPMT | 20–40 | 35 | 30 | 35–45 |

[a]The concentration of BSA relative to the concentration of sample resulting in equal colour formation in the Coomassie brilliant blue dye-binding microassay.

EXAMPLE 17

Examination of *E.coli* and *P. multocida* sonicates for cytopathic activity.

Sonicates of *E.coli* SPE312 and *P. multocida* 45/78, prepared as described in Example 16 were tested for cytopathic effect in the embryonic bovine lung (EBL) cell test (ref. 29). A row of 5-fold dilutions was prepared for each sonicate and 30 μl of each sample was applied to $1.8 \times 10^4$ EBL-cells in 120 μl of culture medium and the mixture incubated for 3 days at 37° C. before fixation and staining. Samples which resulted in monolayers of EEL-cells morphologically discernible from the epithelial-like swirling patterns of negative control culture, were scored as cytopathic. The cytopathic effects for affinity purified rPMT and PMT in the EBL-cell test were determined in the same way. The minimal cytopathic dose (MCD) for the samples was calculated as minimal amount of rPMT or PMT, determined by the quantitative PMT-ELISA causing a cytopathic effect.

Neutralization of the cytopathic effect of *E.coli* SPE 313 sonicate by anti-PMT MAbs was compared to neutralization of pure PMT: Samples (30 μl) containing approximately 1 μg of MAb and varying amounts of sonicate or PMT were incubated for 15 min. at 20° C. before application to EBL-cells. The results were recorded as the number of MCDs neutralized by each MAb, and as the ratio bet-ween the number of neutralized MCDs of the sonicate and pure PMT for each MAb.

Sonicates of SPE308 and SPE312 were shown to cause morphological changes of embryonic bovine lung (EBL) cells, identical to those caused by toxigentc strains of *P. multocida* (FIG. 19 (data for SPE308 not shown)). As observed for pure PMT, the cytopathic effect of the sonicate of *E.coli* SPE312 could be neutralized by incubation with anti-PMT MAbs. Between 5 and 125 times MCD of the sonicate could be neutralized by various anti-PMT MAbs, whereas between 3 and 125 times MCD of the pure PMT were neutralized. The overall mean ± SD for the 10 calculated values of the relative number of neutralized MCDs of *E.coli* SPE312 sonicate compared to PMT was 95%±32%. A PMT-unrelated MAb used as a control did not neutralize the effects of the two cytopathic preparations.

EXAMPLE 18

Analysis of the nature of the DNA flanking the pmt gene

In an attempt to investigate the nature of the DNA flanking the pmt gene in *P. multocida 45/78*, chromosome walking was performed as described in ref. 37. By using a colony hybridization procedure plasmids carrying *P. multocida* DNA were isolated from the *P. multocida* gene library described in Example 4.

Probes

The plasmid pLOL03 was constructed by subcloning a 0.8 kb AccI-HindIII DNA fragment of pSPE344 (FIG. 20) in the vector pGEM-blue (Promega, Wis., USA). The plasmid pLOR02 was likewise constructed by subcloning the 2.4 kb EcoRI-BglIII fragment of pSPE312 (FIG. 20) in the vector pGEM-blue. The *E.coli* K12 strain DH5alpha (BRL, Md. USA) was used as host strain for pLOL03 and pLOR02. pLOL03 and pLOR02 in linearized forms were used for generating RNA probes of the *P. multocida* DNA carried by these plasmids. The RNA probes were radioactively labelled using the Riboprobe System II procedure (Promega, Wis., USA), and used in the colony hybridizations and Southern blots described below.

Colony hybridization

The *P. muitocida* gone library was spread in appropriate dilution on several lB-plates containing 10 μg/ml tetracycline, and incubated overnight at 37° C. Replicas of the plates were made on nitrocellulose membrane filters, and the cells were lysed and the DNA fixed to the filters as described in example 15.

Prehybridization and hybridization was performed at 65° C. in 50% formamide, 6×SSC (0.15 NaCl, 0.015 M tri-sodium citrate, pH 7.0), 0.1% SDS, 5×Denhardt's solution and 200 μg/ml denatured Salmon sperm DNA for at least 2 hours and overnight, respectively. After hybridization, the filters were washed twice at room-temperature in 1×SSC, 0.1% SDS, and twice at 65° C. in 0.1×SSC, 0.1% SDS. After washing, the filters were left overnight for autoradiography.

This procedure resulted in the isolation of a number of clones carrying *P. multocida* DNA flanking the inserts in pSPE308 or pSPE312. These clones were further analyzed using the Southern blot technique (ref. 17). The Southern blots showed that the following plasmids were recognized by the RNA probe coded for by pLOL03: pLOA01, pLOA02 and pLOA03. Similarly the plasmids pLOB01, pLOB02 and pLOB03 were recognized by the RNA probe coded for by pLOR02.

pLOA03 (approx. 14.2 kb) and pLOB03 (approx. 12.7 kb) carried the largest inserts. Their restriction maps and a Southern blot analysis show that pLOA03 and pSPE308 contain overlapping DNA of approximately 4.0 kb and that pLOB03 and pSPE312 contain overlapping DNA of approximately 1.7 kb as shown in FIG. 20.

A Southern blot was made using DNA extracted as described in Examples 4 (a KI gradient (0.875 g/ml) was used instead of the CsCl₂ gradient) from the toxigenic *P. multocida 45/78* and from a non-toxigenic *P. multocida* strain MH81P8, type D (ref. 36) and the plasmids pLOA03, pLOA02, pSPE308, pSPE312 and pLOB03 digested by restriction enzymes as indicated in FIG. 2. The probe was the 2.4 kb BglII-EcoRI fragment of pLOB03 radioactively labelled by nicktranslation (Rigby et al., 1977, (ref. 19)). The result shows that:

1) The probe recognizes a DNA sequence on each of the plasmids pLOA03 and pLOB03. Thus, there is a homologous sequence on each side of the pmt gene. The distance between these homologous sequences is approximately 25 kb.

2) The probe recognizes distinct fragments of the chromosomal DNA of both *P. multocida* strains used in this Southern blot.

The above findings could indicate that the DNA flanking the pmt gene and thus the pmt gene itself has originally been carried by a bacteriophage, a transposon, a plasmid or another genetic element which is integrated into the bacterial chromosome.

Dot blot

DNA from 24 bacteriophages isolated from *P. multocida* strains and all shown to be different in their lysis patterns towards a range of *P. multocida* strains were bound to a nylon filter by dot blotting. The plasmid pLOA03 was radioactively labelled by nicktranslation, and used as a probe against the filter. Hybridization and washing conditions were as described above. The results are shown in FIG. 22. The probe hybridized to 22 out of 24 bacteriophages and, as expected, to the four positive controls. By using pSPE308 and pLOB03 as probes, similar results were obtained. pSPE312 gave only a slight hybridzation to some of the bacteriophage genomes. The 4.5 kb pmt gene containing ClaI-PvuII fragment of pSPE312 (FIG. 5) did not show any homology to any of the bacteriophage genomes (autoradiographs are not shown).

These results show that there are sequences homologous to *P. multocida* bacteriophage DNA on both sides of the pmt gene. This further substantiates the notion that the pmt gene is carried by a prophage.

BIBLIOGRAPHY

1. K.B. Pedersen and K. Barfod, 1981. The aetiological significance of *Borderella bronchiseptica* and *P. multocida* in atrophic rhinitis of swine. Nord. Ver.-Med. 33: pp. 513-522.

5 2. J.M. Rutter and X. Rojas, 1982. Atrophic rhinitis in piglets: Differences in the pathogenicity of *Pasteurella multocida* in combined infections with *Borderella bronchiseptica*. Vet. Rec. 110: pp. 531-535.

3. F. Elling and K.B. Pedersen, 1985. The pathogenesis of persistent turbinate atrophy induced by toxigenic *Pasteurella multocida* in pigs. Vet. Pathol. 22: pp. 469-474.

4. K.B. Pedersen, J.P. Nielsen, N.T. Foged, F. Elling, N.C. Nielsen and P. Willeberg. 1988. Atrophic rhinitis in pigs: Proposal for a revised definition. Vet. Rec. 22: pp. 490-491.

5. K.B. Pedersen and F. Elling, 1984. The pathogenesis of atrophic rhinitis in pigs induced by toxigenic *Pasceurella multocida*. J. Comp. Pathol. 94: pp. 203-214.

6. N.T. Foged, K.B. Pedersen and F. Elling, 1987, Characterization and biological effect of the *P. multocida* toxin. FEMS Microbiol. Lett. 43: pp. 45-51.

7. E.M. Kamp, P.J. v.d. Heijden and B.J. Tetenburg, 1987, Purification of a heat labile dermonecrotic toxin from culture fluid of *Pasteurella multocida*. Vet. Microbiol. 13: pp. 235-248.

8. T. Nakai, A. Sawata, M. Tsuji, Y. Samejima and K. Kume, 1984. Purification of dermonecrotic toxin from a sonic extract of *Pasteurella multocida* SP-72 serotype D. Infect. Immun. 46: pp. 429–434.

9. C.L. Trummel, J.O. Cisar, M.J. Pabst and P. Goforth, 1979. Stimulation of bone resorption by a factor from *Actinomyces viscosus*. J. Perdont. Res. 14: pp. 263-264.

10. P.A. Price, 1987. Structure and function of vitamin K-dependent bone proteins. In: C. Christiansen, J.S. Johansen, B.J. Riis (eds.) Osteoporosis, NØthaven A/S, Viborg, Denmark, pp. 656–663.

11. Casadaban and S. Cohen. 1980. Analysis of gene control signals by DNA fusion and cloning in *Escherichia coli*: J. Mol. Biol. 16: pp. 118–133.

12. J. Mestecky, 1987. The common mucosal immune system and current strategies for induction of immune response in external secretions. J. Clin. Immunol. 7 (4): pp. 265–276.

13. H.W.D. Matthes, W.H. Zenke, T. Grundstrom, A. Staub, M. Wintzerith and P. Chambon, 1984. Simultaneous rapid chemical synthesis of over 100 oligonucleotides on a microscale. The EMBO Journal 3: pp. 801–805.

14.14. T. Maniatis, E.F. Frisch and 3. Sambrook, 1982. Molecular cloning. Cold Spring Harbor Laboratory, Cold Spring Harbor, N.Y.

15.15. G. Köhler and C. Milsrein, 1975. Continuous cultures of fused cells secreting antibody of predefined specificity. Nature, 256: pp. 495–497.

16. G. Klein, J. Luka and J. Zeuthen, 1980. Transformation induced by Epstein-Barr virus and the role of the nuclear antigen. Cold Spring Harbor Symp. Quant. Biol. 44: pp. 253–261.

17. J.W. Goding, 1983. Monoclonal antibodies: Principles and practice. Academic Press, London, 267 pages.

18. E. Southern, 1975, Detection of specific sequences among DN BA fragments separated by gel electrophoresis. *J. Mol. Biol. 98,* pp. 503.

19. Rigby, P.W.J., Dieckmann, M., Rhodes, C., and Berg, P. 1977. Labelling deoxyribonucleic acid to high specific activity in vitro by nick translation with DNA polymerase. I.J.Mol.Biol. 113: pp. 237–251.

20. Gebeyechu, G., Kao, P.Y., SooChan, P., Sins, D.A., and Klevan, L. 1987. Novel biotinylated nucleoticle—analogs for labelling and colorimetric detection of DNA. Nucleic Acids Res. 15: p.p. 4513–4534.

21. R.K. Seiki, S.J. Scharf, F. Faloona, K.B. Mullis, G.T. Horn. H.A. Ehrlich and N.A. Arnhiem, 1985, Enzymatlc amplification of β-globin genomic sequences and restriction site analysis for diagnosis of sickle-cell anemia. Science 230: pp. 1350–1354.

22. J.P. Nielsen, M. Bisgaard, and K.B. Pedersen, 1986, Production of toxin in strains previously classified as *P. multocida*. Acta Path. Microbiol. Immunol Scand. Sec. B, 94: pp. 203–204.

23. S. Fezekes, Groth, S. and D. Scheidegger, Production of monoclonal antibodies: Strategy and tactics, J. Immunol. Meth. 35, 1980, pp. 1–21.

24. U.K. Laemmli, 1970. Cleavage of structural proteins during the assembly of the head of bacteriophage T4. Nature 227: pp. 680–685.

25. J. Kyhse-Andersen, 1984, Electroblotting of multiple gels: A simple apparatus without buffer tank for rapid transfer of proteins from polyacrylamide to nitrocellulose. J. Biochem. Biophys. Methods 10: pp. 203–209.

26. O.J. Bjerrum, K.P. Larsen and M. Wilken, 1983. Some recent developments of the electroimmunochemical analysis of membrane proteins. Application of Zwittergent, Triton X-114 and western blotting technique, pp. 79–124. In H. Tschesche (ed.), Modem methods in protein chemistry. Walther de Gruyter Berlin, N.Y.

27. L.J. Anderson, J.C. Hierholzer, Y.O. Stone, C. Tsou and B.F. Fernie, 1986. Identification of epitopes on respiratory syncytial virus proteins by competitive binding immunoassay. J. Clin. Microbiol. 23: pp. 475–480.

28. J.L. Guesdon, T. Ternynck and T. Avrameas, 1979. The use of avidin-biotin interaction in immunoenzymatic techniques. J. Histochem. Cytochem. 27: pp. 1131–1139.

29. H. Towbin, T. Staehlin and J. Gordon, 1979, Electrophoretic transfer of proteins from polyacrylamide gel to nitrocellulose sheets: Procedure and applications. Proc. Natl. Acad. Sci. USA 76: pp. 4350–4354.

30. M.J. Casabadan and S. Cohen, 1980. Analysis of gene control signals by DNA fusion and cloning in *Escherichia coli*. J. Mol. 138: pp. 179–207.

31. W.B. Wood, 1966. Most specificity of DNA produced by *Escherichia coli*: Bacterial mutations affecting the restriction and modification of DNA. J Mol. Biol. 16pp. 118–133.

32. B. Nilsson, M. Uhlen, S. Josephson, S. Gatenbeck and L. Philipson, 1983, An improved positive selection plasmid vector constructed by oligonucleotide mediated mutagenesis, Nucleic Acids Res. 11(22): pp. 8019–8030.

33. F. Sanger, S. Nicklin and A.R. Coulson, 1977. DNA sequencing with chain-terminating inhibitors. Proc. Nazi. Acad. Sci. USA 7: pp. 5463–5467.

34. D.J. Clark and O. MaalØe, 1967. DNA replication and the division cycle in *Escherichia coli*. J. Mol. Biol. 23:99–112.

35. K.K. Stanley, 1983, Solubilization and immune-detection of β-galactosdase hybrid proteins carrying foreign antigenic determinants. Nucleic Acids Res. 11(12): pp. 4077–4092.

36. J.M. Rutter, 1983. Virulence of *Pasteurella multocida* in atrophic rhinitis of gnotobiotic pigs infected with *Borderella bronchiseptica. Res. Vet. Sci.* 34: pp. 287–295.

37. K. Kaiser and N. Murry, 1985: The use of phage lambda replacement vectors in the construction of representative genomic DNA libraries. In: DNA cloning, Vol. I, A practical approach, D.M. Glover (ed.) IRL Press, Oxford.

SEQUENCE LISTING ( 1 ) GENERAL INFORMATION:

( i i i ) NUMBER OF SEQUENCES: 2

( 2 ) INFORMATION FOR SEQ ID NO:1:

(i) SEQUENCE CHARACTERISTICS:
 (A) LENGTH: 4380 base pairs
 (B) TYPE: nucleic acid
 (C) STRANDEDNESS: single
 (D) TOPOLOGY: linear (ii) MOLECULE TYPE: DNA (genomic)

(vi) ORIGINAL SOURCE:
 (A) ORGANISM: Pasteurella multocida (ix) FEATURE:
 (A) NAME/KEY: CDS
 (B) LOCATION: 219..4073

(xi) SEQUENCE DESCRIPTION: SEQ ID NO:1:

| | | |
|---|---|---|
| AACAAGGGAA AATAGCTAGA TTAGACGATA TCGATAATAT CATAAATAAT ATTTAAAAAT | 60 |
| TACGCCCCTT GACCTAGAGG GGCTTTTTTA TTACATCAAA AAAATAAACC CAAACACTGC | 120 |
| GAATGTTGG GGTTTTATTT ATAACCAAAA TACATTAATA TGTTTATTAA GTAAGCATTA | 180 |
| TCTTACTTTA GGAATAAACT AACATAGAGG TTATGGAT ATG AAA ACA AAA CAT | 233 |

```
                                             Met Lys Thr Lys His
                                              1               5

TTT TTT AAC TCA GAT TTT ACT GTA AAA GGA AAA AGT GCC GAT GAA ATT      281
Phe Phe Asn Ser Asp Phe Thr Val Lys Gly Lys Ser Ala Asp Glu Ile
            10                  15                  20

TTT AGA AGA TTG TGT ACT GAT CAT CCT GAC AAG CAA TTA AAC AAT GTA      329
Phe Arg Arg Leu Cys Thr Asp His Pro Asp Lys Gln Leu Asn Asn Val
                25                  30                  35

AAA TGG AAA GAA GTT TTT ATT AAT CGT TTT GGT CAG ATG ATG CTA GAT      377
Lys Trp Lys Glu Val Phe Ile Asn Arg Phe Gly Gln Met Met Leu Asp
        40                  45                  50

ACT CCT AAT CCG AGA AAG ATT GTA GAA AAA ATT ATT AAT GAA GGG CTT      425
Thr Pro Asn Pro Arg Lys Ile Val Glu Lys Ile Ile Asn Glu Gly Leu
    55                  60                  65

GAA AAA CAA GGC CTG AAA AAT ATA GAT CCT GAA AAC ACA TAT TTC AAC      473
Glu Lys Gln Gly Leu Lys Asn Ile Asp Pro Glu Asn Thr Tyr Phe Asn
70                  75                  80                  85

ATT TTT TCA TCT TCT GAC AGC TCC GAT GGG AAC GTT TTT CAT TAT AAC      521
Ile Phe Ser Ser Ser Asp Ser Ser Asp Gly Asn Val Phe His Tyr Asn
                90                  95                  100

TCT TTA TCA GAA TCC TAT CGA GTT ACT GAT GCC TGC CTA ATG AAT ATT      569
Ser Leu Ser Glu Ser Tyr Arg Val Thr Asp Ala Cys Leu Met Asn Ile
            105                 110                 115

TTT GTG GAG CGT TAT TTT GAT GAT TGG GAC TTG CTA AAT AGC TTA GCC      617
Phe Val Glu Arg Tyr Phe Asp Asp Trp Asp Leu Leu Asn Ser Leu Ala
        120                 125                 130

AGT AAT GGA ATA TAT TCA GTA GGA AAA GAA GGA GCT TAT TAT CCT GAT      665
Ser Asn Gly Ile Tyr Ser Val Gly Lys Glu Gly Ala Tyr Tyr Pro Asp
    135                 140                 145

CAT GAT TAT GGT CCA GAA TAT AAC CCT GTT TGG GGA CCA AAC GAA CAA      713
His Asp Tyr Gly Pro Glu Tyr Asn Pro Val Trp Gly Pro Asn Glu Gln
150                 155                 160                 165

ATT TAC CAT TCT AGA GTG ATT GCA GAT ATC CTT TAT GCT CGC TCC GTA      761
Ile Tyr His Ser Arg Val Ile Ala Asp Ile Leu Tyr Ala Arg Ser Val
                170                 175                 180

TGG GAT GAA TTT AAA AAA TAC TTC ATG GAG TAT TGG CAA AAA TAT GCT      809
Trp Asp Glu Phe Lys Lys Tyr Phe Met Glu Tyr Trp Gln Lys Tyr Ala
            185                 190                 195

CAG CTT TAT ACC GAA ATG TTA TCT GAT ACA TTT CTT GCA ATG GCT ATT      857
Gln Leu Tyr Thr Glu Met Leu Ser Asp Thr Phe Leu Ala Met Ala Ile
        200                 205                 210

CAG CAA TAT ACA CGA CAA ACG CTT ACT GAT GAA GGC TTT CTT ATG GTT      905
Gln Gln Tyr Thr Arg Gln Thr Leu Thr Asp Glu Gly Phe Leu Met Val
```

|  |  |  |  |  |  |  |  |  |  |  |  |  |  |  |  |
|---|---|---|---|---|---|---|---|---|---|---|---|---|---|---|---|
| | 215 | | | | 220 | | | | | | 225 | | | | |

| TGT | AAC | ACA | TAT | TAT | GGC | AAT | AAG | GAA | GAA | GTT | CAA | ATA | ACT | CTA | CTA | 953 |
|---|---|---|---|---|---|---|---|---|---|---|---|---|---|---|---|---|
| Cys | Asn | Thr | Tyr | Tyr | Gly | Asn | Lys | Glu | Glu | Val | Gln | Ile | Thr | Leu | Leu | |
| 230 | | | | | 235 | | | | 240 | | | | | | 245 | |

| GAT | ATC | TAT | GGA | TAC | CCT | TCC | ACT | GAT | ATA | ATT | TGT | ATA | GAG | CAA | AAA | 1001 |
|---|---|---|---|---|---|---|---|---|---|---|---|---|---|---|---|---|
| Asp | Ile | Tyr | Gly | Tyr | Pro | Ser | Thr | Asp | Ile | Ile | Cys | Ile | Glu | Gln | Lys | |
| | | | 250 | | | | 255 | | | | 260 | | | | | |

| GGG | CTT | CCT | ACT | CCT | AAA | GTG | ATA | CTT | TAC | ATT | CCT | GGA | GGA | ACA | CAA | 1049 |
|---|---|---|---|---|---|---|---|---|---|---|---|---|---|---|---|---|
| Gly | Leu | Pro | Thr | Pro | Lys | Val | Ile | Leu | Tyr | Ile | Pro | Gly | Gly | Thr | Gln | |
| | | | 265 | | | | 270 | | | | 275 | | | | | |

| CCA | TTT | GTT | GAA | TTT | CTT | AAT | ACA | GAT | GAT | CTG | AAA | CAA | TGG | ATT | GCA | 1097 |
|---|---|---|---|---|---|---|---|---|---|---|---|---|---|---|---|---|
| Pro | Phe | Val | Glu | Phe | Leu | Asn | Thr | Asp | Asp | Leu | Lys | Gln | Trp | Ile | Ala | |
| | | 280 | | | | | 285 | | | | | 290 | | | | |

| TGG | CAT | TTA | AAA | GAT | AAC | AAA | CAT | ATG | GTC | CGA | TTC | CGC | AAA | CAT | TTC | 1145 |
|---|---|---|---|---|---|---|---|---|---|---|---|---|---|---|---|---|
| Trp | His | Leu | Lys | Asp | Asn | Lys | His | Met | Val | Arg | Phe | Arg | Lys | His | Phe | |
| 295 | | | | | 300 | | | | | 305 | | | | | | |

| TCG | CTA | AAA | CAA | CGT | CAG | GAA | GGA | GAA | ACG | TTT | ACA | GGT | ATA | GAT | AAA | 1193 |
|---|---|---|---|---|---|---|---|---|---|---|---|---|---|---|---|---|
| Ser | Leu | Lys | Gln | Arg | Gln | Glu | Gly | Glu | Thr | Phe | Thr | Gly | Ile | Asp | Lys | |
| 310 | | | | | 315 | | | | | 320 | | | | | 325 | |

| GCA | CTT | CAA | TAT | ATT | GCA | GAA | GAG | TCC | CCT | GAA | TGG | CCT | GCC | AAT | AAA | 1241 |
|---|---|---|---|---|---|---|---|---|---|---|---|---|---|---|---|---|
| Ala | Leu | Gln | Tyr | Ile | Ala | Glu | Glu | Ser | Pro | Glu | Trp | Pro | Ala | Asn | Lys | |
| | | | | 330 | | | | | 335 | | | | | 340 | | |

| TAC | ATC | CTT | TAT | AAT | CCG | ACA | CAT | TTA | GAA | ACA | GAA | AAT | TTA | TTT | AAC | 1289 |
|---|---|---|---|---|---|---|---|---|---|---|---|---|---|---|---|---|
| Tyr | Ile | Leu | Tyr | Asn | Pro | Thr | His | Leu | Glu | Thr | Glu | Asn | Leu | Phe | Asn | |
| | | | 345 | | | | | 350 | | | | | 355 | | | |

| ATC | ATG | ATG | AAG | CGA | ACA | GAA | CAG | CGG | ATG | CTT | GAA | GAT | AGT | GAT | GTA | 1337 |
|---|---|---|---|---|---|---|---|---|---|---|---|---|---|---|---|---|
| Ile | Met | Met | Lys | Arg | Thr | Glu | Gln | Arg | Met | Leu | Glu | Asp | Ser | Asp | Val | |
| | | 360 | | | | | 365 | | | | | 370 | | | | |

| CAG | ATT | AGA | TCA | AAT | TCA | GAA | GCT | ACC | CGT | GAC | TAT | GCT | CTT | TCA | TTA | 1385 |
|---|---|---|---|---|---|---|---|---|---|---|---|---|---|---|---|---|
| Gln | Ile | Arg | Ser | Asn | Ser | Glu | Ala | Thr | Arg | Asp | Tyr | Ala | Leu | Ser | Leu | |
| 375 | | | | | 380 | | | | | 385 | | | | | | |

| CTC | GAA | ACC | TTT | ATT | TCA | CAG | TTA | TCT | GCA | ATA | GAT | ATG | TTA | GTA | CCA | 1433 |
|---|---|---|---|---|---|---|---|---|---|---|---|---|---|---|---|---|
| Leu | Glu | Thr | Phe | Ile | Ser | Gln | Leu | Ser | Ala | Ile | Asp | Met | Leu | Val | Pro | |
| 390 | | | | | 395 | | | | | 400 | | | | | 405 | |

| GCA | GTA | GGT | ATC | CCA | ATT | AAT | TTT | GCC | CTA | TCA | GCT | ACA | GCA | TTA | GGA | 1481 |
|---|---|---|---|---|---|---|---|---|---|---|---|---|---|---|---|---|
| Ala | Val | Gly | Ile | Pro | Ile | Asn | Phe | Ala | Leu | Ser | Ala | Thr | Ala | Leu | Gly | |
| | | | | 410 | | | | 415 | | | | | 420 | | | |

| CTT | AGC | TCG | GAT | ATT | GTA | GTT | AAT | GGA | GAT | TCA | TAT | GAA | AAG | AGA | AAA | 1529 |
|---|---|---|---|---|---|---|---|---|---|---|---|---|---|---|---|---|
| Leu | Ser | Ser | Asp | Ile | Val | Val | Asn | Gly | Asp | Ser | Tyr | Glu | Lys | Arg | Lys | |
| | | | 425 | | | | 430 | | | | | 435 | | | | |

| TAT | GGA | ATT | GGG | TCC | TTA | GTG | CAA | TCT | GCA | TTA | TTC | ACA | GGA | ATT | AAT | 1577 |
|---|---|---|---|---|---|---|---|---|---|---|---|---|---|---|---|---|
| Tyr | Gly | Ile | Gly | Ser | Leu | Val | Gln | Ser | Ala | Leu | Phe | Thr | Gly | Ile | Asn | |
| | | 440 | | | | | 445 | | | | | 450 | | | | |

| CTT | ATT | CCA | GTT | ATT | TCG | GAA | ACC | GCA | GAA | ATT | TTA | TCT | TCT | TTC | TCT | 1625 |
|---|---|---|---|---|---|---|---|---|---|---|---|---|---|---|---|---|
| Leu | Ile | Pro | Val | Ile | Ser | Glu | Thr | Ala | Glu | Ile | Leu | Ser | Ser | Phe | Ser | |
| 455 | | | | | 460 | | | | | 465 | | | | | | |

| AGA | ACA | GAA | GAA | GAT | ATT | CCA | GCT | TTT | TTC | ACT | GAA | GAA | CAA | GCT | TTA | 1673 |
|---|---|---|---|---|---|---|---|---|---|---|---|---|---|---|---|---|
| Arg | Thr | Glu | Glu | Asp | Ile | Pro | Ala | Phe | Phe | Thr | Glu | Glu | Gln | Ala | Leu | |
| 470 | | | | | 475 | | | | | 480 | | | | | 485 | |

| GCT | CAA | CGC | TTT | GAA | ATA | GTA | GAA | GAA | GAA | TTA | CAT | TCT | ATC | TCA | CCT | 1721 |
|---|---|---|---|---|---|---|---|---|---|---|---|---|---|---|---|---|
| Ala | Gln | Arg | Phe | Glu | Ile | Val | Glu | Glu | Glu | Leu | His | Ser | Ile | Ser | Pro | |
| | | | | 490 | | | | | 495 | | | | | 500 | | |

| GAT | GAT | CCT | CCT | CGA | GAA | ATT | ACT | GAC | GAA | AAT | TTA | CAT | AAA | ATT | CGT | 1769 |
|---|---|---|---|---|---|---|---|---|---|---|---|---|---|---|---|---|
| Asp | Asp | Pro | Pro | Arg | Glu | Ile | Thr | Asp | Glu | Asn | Leu | His | Lys | Ile | Arg | |
| | | | 505 | | | | | 510 | | | | | 515 | | | |

| CTG | GTA | CGT | CTT | AAC | AAT | GAA | AAT | CAA | CCT | TTA | GTT | GTG | TTA | CGA | AGA | 1817 |
|---|---|---|---|---|---|---|---|---|---|---|---|---|---|---|---|---|
| Leu | Val | Arg | Leu | Asn | Asn | Glu | Asn | Gln | Pro | Leu | Val | Val | Leu | Arg | Arg | |
| | | 520 | | | | | 525 | | | | | 530 | | | | |

| TTA | GGA | GGA | AAT | AAA | TTT | ATC | AGA | ATC | GAG | CCT | ATA | ACA | TTC | CAG | GAA | 1865 |
|---|---|---|---|---|---|---|---|---|---|---|---|---|---|---|---|---|
| Leu | Gly | Gly | Asn | Lys | Phe | Ile | Arg | Ile | Glu | Pro | Ile | Thr | Phe | Gln | Glu | |
| 535 | | | | | 540 | | | | | 545 | | | | | | |

| | | | | | | | | | | | | | | | | |
|---|---|---|---|---|---|---|---|---|---|---|---|---|---|---|---|---|
| ATA | AAA | GGT | TCT | TTA | GTA | AGT | GAA | GTT | ATA | AAT | CCA | GTG | ACT | AAT | AAA | 1913 |
| Ile | Lys | Gly | Ser | Leu | Val | Ser | Glu | Val | Ile | Asn | Pro | Val | Thr | Asn | Lys | |
| 550 | | | | | 555 | | | | 560 | | | | | | 565 | |
| ACG | TAC | TAC | GTA | AGC | AAT | GCT | AAA | CTA | TTA | GGG | GGC | TCT | CCT | TAT | AGT | 1961 |
| Thr | Tyr | Tyr | Val | Ser | Asn | Ala | Lys | Leu | Leu | Gly | Gly | Ser | Pro | Tyr | Ser | |
| | | | | 570 | | | | | 575 | | | | | 580 | | |
| CCT | TTC | CGT | ATT | GGA | TTA | GAA | GGT | GTT | TGG | ACA | CCA | GAG | GTA | TTA | AAA | 2009 |
| Pro | Phe | Arg | Ile | Gly | Leu | Glu | Gly | Val | Trp | Thr | Pro | Glu | Val | Leu | Lys | |
| | | | 585 | | | | | 590 | | | | | 595 | | | |
| GCA | AGA | GCT | TCC | GTT | ATT | GGA | AAG | CCT | ATT | GGA | GAA | TCA | TAT | AAA | AGA | 2057 |
| Ala | Arg | Ala | Ser | Val | Ile | Gly | Lys | Pro | Ile | Gly | Glu | Ser | Tyr | Lys | Arg | |
| | | 600 | | | | | 605 | | | | | 610 | | | | |
| ATA | TTA | GCC | AAA | CTA | CAA | AGA | ATA | CAT | AAC | AGT | AAT | ATC | TTA | GAT | GAG | 2105 |
| Ile | Leu | Ala | Lys | Leu | Gln | Arg | Ile | His | Asn | Ser | Asn | Ile | Leu | Asp | Glu | |
| 615 | | | | | 620 | | | | | 625 | | | | | | |
| CGA | CAA | GGT | TTA | ATG | CAT | GAA | CTC | ATG | GAG | CTT | ATT | GAT | CTT | TAT | GAA | 2153 |
| Arg | Gln | Gly | Leu | Met | His | Glu | Leu | Met | Glu | Leu | Ile | Asp | Leu | Tyr | Glu | |
| 630 | | | | | 635 | | | | | 640 | | | | | 645 | |
| GAA | TCG | CAA | CCT | TCT | TCA | GAG | CGT | TTG | AAT | GCT | TTT | CGT | GAA | CTG | CGT | 2201 |
| Glu | Ser | Gln | Pro | Ser | Ser | Glu | Arg | Leu | Asn | Ala | Phe | Arg | Glu | Leu | Arg | |
| | | | | 650 | | | | | 655 | | | | | 660 | | |
| ACT | CAA | TTA | GAA | AAA | GCG | CTT | TAT | CTT | CCT | GAA | ATG | GAA | GCA | TTA | AAA | 2249 |
| Thr | Gln | Leu | Glu | Lys | Ala | Leu | Tyr | Leu | Pro | Glu | Met | Glu | Ala | Leu | Lys | |
| | | | 665 | | | | | 670 | | | | | 675 | | | |
| AAA | CAA | ATA | CTA | CAG | ATT | CCT | AAC | AAA | GGT | TCT | GGT | GCC | GCT | CGA | TTT | 2297 |
| Lys | Gln | Ile | Leu | Gln | Ile | Pro | Asn | Lys | Gly | Ser | Gly | Ala | Ala | Arg | Phe | |
| | | 680 | | | | | 685 | | | | | 690 | | | | |
| TTA | CTT | CGT | ACA | GCC | ATG | AAT | GAA | ATG | GCT | GGA | AAA | ACC | AGT | GAA | AGC | 2345 |
| Leu | Leu | Arg | Thr | Ala | Met | Asn | Glu | Met | Ala | Gly | Lys | Thr | Ser | Glu | Ser | |
| 695 | | | | | 700 | | | | | 705 | | | | | | |
| ACG | GCT | GAT | TTA | ATA | CGC | TTT | GCC | TTG | CAA | GAT | ACA | GTA | ATT | TCA | GCG | 2393 |
| Thr | Ala | Asp | Leu | Ile | Arg | Phe | Ala | Leu | Gln | Asp | Thr | Val | Ile | Ser | Ala | |
| 710 | | | | | 715 | | | | | 720 | | | | | 725 | |
| CCT | TTT | CGC | GGA | TAT | GCT | GGT | GCG | ATT | CCA | GAG | GCA | ATA | GAC | TTT | CCT | 2441 |
| Pro | Phe | Arg | Gly | Tyr | Ala | Gly | Ala | Ile | Pro | Glu | Ala | Ile | Asp | Phe | Pro | |
| | | | | 730 | | | | | 735 | | | | | 740 | | |
| GTA | AAA | TAT | GTA | ATA | GAA | GAC | ATA | TCT | GTA | TTT | GAT | AAA | ATA | CAG | ACA | 2489 |
| Val | Lys | Tyr | Val | Ile | Glu | Asp | Ile | Ser | Val | Phe | Asp | Lys | Ile | Gln | Thr | |
| | | | 745 | | | | | 750 | | | | | 755 | | | |
| AAT | TAC | TGG | GAA | CTT | CCT | GCT | TAT | GAA | AGC | TGG | AAC | GAA | GGA | AGT | AAT | 2537 |
| Asn | Tyr | Trp | Glu | Leu | Pro | Ala | Tyr | Glu | Ser | Trp | Asn | Glu | Gly | Ser | Asn | |
| | | 760 | | | | | 765 | | | | | 770 | | | | |
| AGC | CGA | TTA | CTG | CCT | GGT | TTG | TTA | CGT | GAA | TCG | CAA | AGC | AAG | GGG | ATG | 2585 |
| Ser | Arg | Leu | Leu | Pro | Gly | Leu | Leu | Arg | Glu | Ser | Gln | Ser | Lys | Gly | Met | |
| 775 | | | | | 780 | | | | | 785 | | | | | | |
| TTA | AGT | AAG | TGT | CGT | ATC | ATA | GAA | AAT | AGC | CTT | TAT | ATT | GGA | CAT | AGC | 2633 |
| Leu | Ser | Lys | Cys | Arg | Ile | Ile | Glu | Asn | Ser | Leu | Tyr | Ile | Gly | His | Ser | |
| 790 | | | | | 795 | | | | | 800 | | | | | 805 | |
| TAT | GAA | GAA | ATG | TTT | TAC | AGC | ATT | TCT | CCA | TAT | TCA | AAC | CAG | GTT | GGA | 2681 |
| Tyr | Glu | Glu | Met | Phe | Tyr | Ser | Ile | Ser | Pro | Tyr | Ser | Asn | Gln | Val | Gly | |
| | | | | 810 | | | | | 815 | | | | | 820 | | |
| GGG | CCT | TAT | GAA | TTA | TAT | CCT | TTC | ACT | TTT | TCA | GTA | ATG | CTT | CAA | GAA | 2729 |
| Gly | Pro | Tyr | Glu | Leu | Tyr | Pro | Phe | Thr | Phe | Ser | Met | Leu | Gln | Glu | | |
| | | | 825 | | | | | 830 | | | | | 835 | | | |
| GTA | CAA | GGT | GAT | TTA | GGA | TTT | GAG | CAG | GCC | TTT | GCC | ACA | CGT | AAC | TTT | 2777 |
| Val | Gln | Gly | Asp | Leu | Gly | Phe | Glu | Gln | Ala | Phe | Ala | Thr | Arg | Asn | Phe | |
| | | | 840 | | | | | 845 | | | | | 850 | | | |
| TTC | AAT | ACT | CTT | GTT | TCT | GAT | CGA | CTA | TCC | TTA | ATG | GAA | AAT | ACG | ATG | 2825 |
| Phe | Asn | Thr | Leu | Val | Ser | Asp | Arg | Leu | Ser | Leu | Met | Glu | Asn | Thr | Met | |
| 855 | | | | | 860 | | | | | 865 | | | | | | |
| TTA | CTT | ACA | GAA | AGT | TTT | GAT | TAT | ACA | CCT | TGG | GAT | GCT | ATT | TAT | GGA | 2873 |
| Leu | Leu | Thr | Glu | Ser | Phe | Asp | Tyr | Thr | Pro | Trp | Asp | Ala | Ile | Tyr | Gly | |

| | | | |
|---|---|---|---|
| 870 | 875 | 880 | 885 |

GAT ATT AAT TAT GAT GAA CAA TTT GCT GCA ATG TCT ATT AAT GAA CGC   2921
Asp Ile Asn Tyr Asp Glu Gln Phe Ala Ala Met Ser Ile Asn Glu Arg
            890             895             900

ATA GAA AAA TGT ATG AAT ACC TAT AGA GGT GTG GCA TTC CAA AAC TCT   2969
Ile Glu Lys Cys Met Asn Thr Tyr Arg Gly Val Ala Phe Gln Asn Ser
            905             910             915

TCA AAA AGT ATT GAC TTT TTC CTA AAT AAT CTA ACC ACA TTC ATT GAT   3017
Ser Lys Ser Ile Asp Phe Phe Leu Asn Asn Leu Thr Thr Phe Ile Asp
            920             925             930

AAT GGA CTA ACC GAA ATT GCT ATA TCT GAT TTA CCG TAT GAT ATT GTG   3065
Asn Gly Leu Thr Glu Ile Ala Ile Ser Asp Leu Pro Tyr Asp Ile Val
            935             940             945

CAA CAA GAA ATC TCT CAA TTC TTA CAA GGA AGT AAT GAA TGG AAA ACA   3113
Gln Gln Glu Ile Ser Gln Phe Leu Gln Gly Ser Asn Glu Trp Lys Thr
950             955             960             965

CTT GAT GCC ATG TTA TTT AAC TTA GAT AAA GGA GAT ATT AAT GGT GCT   3161
Leu Asp Ala Met Leu Phe Asn Leu Asp Lys Gly Asp Ile Asn Gly Ala
            970             975             980

TTC AGA AAG CTT CTG CAA TCA GCA AAA GAT AAT AAT ATA AAA TTT AGA   3209
Phe Arg Lys Leu Leu Gln Ser Ala Lys Asp Asn Asn Ile Lys Phe Arg
            985             990             995

GCT ATA GGG CAT TCA GAT AAT TCT GTT CCG CCA TTT AAT AAC CCT TAT   3257
Ala Ile Gly His Ser Asp Asn Ser Val Pro Pro Phe Asn Asn Pro Tyr
            1000            1005            1010

AAG TCT TTA TAT TAT AAA GGA AAT ATA ATA GCT GAA GCA ATT GAA AAA   3305
Lys Ser Leu Tyr Tyr Lys Gly Asn Ile Ile Ala Glu Ala Ile Glu Lys
            1015            1020            1025

CTA GAT CGA GAA GGT CAA AAA TTT GTT GTA TTT GCT GAT AGT TCT CTG   3353
Leu Asp Arg Glu Gly Gln Lys Phe Val Val Phe Ala Asp Ser Ser Leu
1030            1035            1040            1045

CTC AAC AGC ACG CCT GGG ACA GGT CGT CCT ATG CCA GGA CTA GTT CAA   3401
Leu Asn Ser Thr Pro Gly Thr Gly Arg Pro Met Pro Gly Leu Val Gln
            1050            1055            1060

TAT TTA AAA ATA CCA GCA ACT GTA GTA GAT AGC GAT GGT GCA TGG CAA   3449
Tyr Leu Lys Ile Pro Ala Thr Val Val Asp Ser Asp Gly Ala Trp Gln
            1065            1070            1075

TTT CTT CCA GAT GTA GCT TCA AGC AGA GTT CCT ATT GAA GTT ACA GAG   3497
Phe Leu Pro Asp Val Ala Ser Ser Arg Val Pro Ile Glu Val Thr Glu
            1080            1085            1090

TTA GAA AAT TGG CAA GTC TTA ACT CCT CCA CAA GGT AAG ATT CTT GGA   3545
Leu Glu Asn Trp Gln Val Leu Thr Pro Pro Gln Gly Lys Ile Leu Gly
            1095            1100            1105

TTA AAG CAA TTT AAG TTA ACG GCA GGT TTT CCA ACA GAA CAA AGT CGC   3593
Leu Lys Gln Phe Lys Leu Thr Ala Gly Phe Pro Thr Glu Gln Ser Arg
1110            1115            1120            1125

TTA CCT CTT TTA GAG AAT TCG GTT TCT GAA GAT TTA AGG GAA GAA TTA   3641
Leu Pro Leu Leu Glu Asn Ser Val Ser Glu Asp Leu Arg Glu Glu Leu
            1130            1135            1140

ATG CAA AAG ATT GAT GCA ATA AAA AAT GAT GTG AAA ATG AAT AGT TTA   3689
Met Gln Lys Ile Asp Ala Ile Lys Asn Asp Val Lys Met Asn Ser Leu
            1145            1150            1155

GTG TGT ATG GAA GCT GGC TCT TGT GAT TCA GTA AGC CCT AAG GTA GCT   3737
Val Cys Met Glu Ala Gly Ser Cys Asp Ser Val Ser Pro Lys Val Ala
            1160            1165            1170

GCC CGT CTT AAA GAT ATG GGG TTA GAA GCT GGG ATG GGT GCT TCT ATT   3785
Ala Arg Leu Lys Asp Met Gly Leu Glu Ala Gly Met Gly Ala Ser Ile
            1175            1180            1185

ACC TGG TGG AGA CGT GAA GGC GGG ATG GAA TTT TCA CAT CAG ATG CAT   3833
Thr Trp Trp Arg Arg Glu Gly Gly Met Glu Phe Ser His Gln Met His
1190            1195            1200            1205

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ACT | ACT | GCT | TCC | TTT | AAA | TTT | GCT | GGT | AAA | GAG | TTT | GCC | GTG | GAT | GCT | 3881 |
| Thr | Thr | Ala | Ser | Phe | Lys | Phe | Ala | Gly | Lys | Glu | Phe | Ala | Val | Asp | Ala |      |
|     |     |     |     | 1210 |     |     |     |     | 1215 |     |     |     |     | 1220 |     |      |
| TCA | CAT | TTA | CAA | TTT | GTA | CAC | GAC | CAA | TTA | GAT | ACA | ACT | ATC | CTG | ATA | 3929 |
| Ser | His | Leu | Gln | Phe | Val | His | Asp | Gln | Leu | Asp | Thr | Thr | Ile | Leu | Ile |      |
|     |     |     | 1225 |     |     |     |     | 1230 |     |     |     |     | 1235 |     |     |      |
| CTA | CCT | GTA | GAT | GAT | TGG | GCT | TTA | GAA | ATA | GCT | CAA | AGA | AAT | CGG | GCT | 3977 |
| Leu | Pro | Val | Asp | Asp | Trp | Ala | Leu | Glu | Ile | Ala | Gln | Arg | Asn | Arg | Ala |      |
|     |     | 1240 |     |     |     |     | 1245 |     |     |     |     | 1250 |     |     |     |      |
| ATT | AAT | CCT | TTT | GTG | GAA | TAT | GTT | AGT | AAA | ACA | GGA | AAC | ATG | TTA | GCA | 4025 |
| Ile | Asn | Pro | Phe | Val | Glu | Tyr | Val | Ser | Lys | Thr | Gly | Asn | Met | Leu | Ala |      |
|     | 1255 |     |     |     |     | 1260 |     |     |     |     | 1265 |     |     |     |     |      |
| CTC | TTC | ATG | CCT | CCT | CTT | TTC | ACA | AAG | CCT | CGC | TTA | ACA | AGA | GCA | CTA | 4073 |
| Leu | Phe | Met | Pro | Pro | Leu | Phe | Thr | Lys | Pro | Arg | Leu | Thr | Arg | Ala | Leu |      |
| 1270 |     |     |     | 1275 |     |     |     |     | 1280 |     |     |     |     | 1285 |     |      |

|             |           |      |
| ----------- | --------- | ---- |
| TAACTAATTA  | AAAACTGTAT | TAAAGCCTTA TATTATAAGG CTTTAATTTT CTTTCAAGAA | 4133 |
| TTATTAAGTA  | GAAGAATCAA | AATCAATGAG ATAGATAAAA TCAAATGTTA TTACCAATAC | 4193 |
| AACTTTCTTA  | AGTATACTTT | TGAATTTTT TGCGTTAATA AATTTATAAT ACCCTTAACT | 4253 |
| CAATAAAAGA  | AGTTATTGAG | AAGTTTAAAT CTTGTGAGCA AGATGAAGAT ATAATTTCAG | 4313 |
| CAATCGATCT  | TATTAGCGCT | TCATATAGAA GGGCTGTGGA TGCAGTGGAA CAAAGATTCG | 4373 |
| GTTCTAG     |           | 4380 |

( 2 ) INFORMATION FOR SEQ ID NO:2:

( i ) SEQUENCE CHARACTERISTICS:
        ( A ) LENGTH: 1285 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Lys | Thr | Lys | His | Phe | Phe | Asn | Ser | Asp | Phe | Thr | Val | Lys | Gly | Lys |
| 1 | | | | 5 | | | | | 10 | | | | | 15 |
| Ser | Ala | Asp | Glu | Ile | Phe | Arg | Arg | Leu | Cys | Thr | Asp | His | Pro | Asp | Lys |
| | | | 20 | | | | | 25 | | | | | 30 | |
| Gln | Leu | Asn | Asn | Val | Lys | Trp | Lys | Glu | Val | Phe | Ile | Asn | Arg | Phe | Gly |
| | | | 35 | | | | | 40 | | | | | 45 | |
| Gln | Met | Met | Leu | Asp | Thr | Pro | Asn | Pro | Arg | Lys | Ile | Val | Glu | Lys | Ile |
| | 50 | | | | | 55 | | | | | 60 | | | | |
| Ile | Asn | Glu | Gly | Leu | Glu | Lys | Gln | Gly | Leu | Lys | Asn | Ile | Asp | Pro | Glu |
| 65 | | | | | 70 | | | | | 75 | | | | | 80 |
| Asn | Thr | Tyr | Phe | Asn | Ile | Phe | Ser | Ser | Ser | Asp | Ser | Ser | Asp | Gly | Asn |
| | | | | 85 | | | | | 90 | | | | | 95 | |
| Val | Phe | His | Tyr | Asn | Ser | Leu | Ser | Glu | Ser | Tyr | Arg | Val | Thr | Asp | Ala |
| | | | | 100 | | | | | 105 | | | | | 110 | |
| Cys | Leu | Met | Asn | Ile | Phe | Val | Glu | Arg | Tyr | Phe | Asp | Asp | Trp | Asp | Leu |
| | | | 115 | | | | | 120 | | | | | 125 | | |
| Leu | Asn | Ser | Leu | Ala | Ser | Asn | Gly | Ile | Tyr | Ser | Val | Gly | Lys | Glu | Gly |
| | | 130 | | | | | 135 | | | | | 140 | | | |
| Ala | Tyr | Tyr | Pro | Asp | His | Asp | Tyr | Gly | Pro | Glu | Tyr | Asn | Pro | Val | Trp |
| 145 | | | | | 150 | | | | | 155 | | | | | 160 |
| Gly | Pro | Asn | Glu | Gln | Ile | Tyr | His | Ser | Arg | Val | Ile | Ala | Asp | Ile | Leu |
| | | | | 165 | | | | | 170 | | | | | 175 | |
| Tyr | Ala | Arg | Ser | Val | Trp | Asp | Glu | Phe | Lys | Lys | Tyr | Phe | Met | Glu | Tyr |
| | | | 180 | | | | | 185 | | | | | 190 | | |
| Trp | Gln | Lys | Tyr | Ala | Gln | Leu | Tyr | Thr | Glu | Met | Leu | Ser | Asp | Thr | Phe |
| | | | 195 | | | | | 200 | | | | | 205 | | |

```
Leu  Ala  Met  Ala  Ile  Gln  Gln  Tyr  Thr  Arg  Gln  Thr  Leu  Thr  Asp  Glu
210                 215                      220

Gly  Phe  Leu  Met  Val  Cys  Asn  Thr  Tyr  Tyr  Gly  Asn  Lys  Glu  Glu  Val
225                      230                 235                           240

Gln  Ile  Thr  Leu  Leu  Asp  Ile  Tyr  Gly  Tyr  Pro  Ser  Thr  Asp  Ile  Ile
                    245                 250                      255

Cys  Ile  Glu  Gln  Lys  Gly  Leu  Pro  Thr  Pro  Lys  Val  Ile  Leu  Tyr  Ile
               260                      265                      270

Pro  Gly  Gly  Thr  Gln  Pro  Phe  Val  Glu  Phe  Leu  Asn  Thr  Asp  Asp  Leu
          275                      280                      285

Lys  Gln  Trp  Ile  Ala  Trp  His  Leu  Lys  Asp  Asn  Lys  His  Met  Val  Arg
     290                 295                      300

Phe  Arg  Lys  His  Phe  Ser  Leu  Lys  Gln  Arg  Gln  Glu  Gly  Glu  Thr  Phe
305                 310                      315                           320

Thr  Gly  Ile  Asp  Lys  Ala  Leu  Gln  Tyr  Ile  Ala  Glu  Glu  Ser  Pro  Glu
               325                      330                      335

Trp  Pro  Ala  Asn  Lys  Tyr  Ile  Leu  Tyr  Asn  Pro  Thr  His  Leu  Glu  Thr
               340                      345                      350

Glu  Asn  Leu  Phe  Asn  Ile  Met  Met  Lys  Arg  Thr  Glu  Gln  Arg  Met  Leu
               355                      360                      365

Glu  Asp  Ser  Asp  Val  Gln  Ile  Arg  Ser  Asn  Ser  Glu  Ala  Thr  Arg  Asp
               370                      375                      380

Tyr  Ala  Leu  Ser  Leu  Leu  Glu  Thr  Phe  Ile  Ser  Gln  Leu  Ser  Ala  Ile
385                      390                      395                      400

Asp  Met  Leu  Val  Pro  Ala  Val  Gly  Ile  Pro  Ile  Asn  Phe  Ala  Leu  Ser
                    405                      410                      415

Ala  Thr  Ala  Leu  Gly  Leu  Ser  Ser  Asp  Ile  Val  Val  Asn  Gly  Asp  Ser
               420                      425                      430

Tyr  Glu  Lys  Arg  Lys  Tyr  Gly  Ile  Gly  Ser  Leu  Val  Gln  Ser  Ala  Leu
          435                      440                      445

Phe  Thr  Gly  Ile  Asn  Leu  Ile  Pro  Val  Ile  Ser  Glu  Thr  Ala  Glu  Ile
450                      455                      460

Leu  Ser  Ser  Phe  Ser  Arg  Thr  Glu  Glu  Asp  Ile  Pro  Ala  Phe  Phe  Thr
465                      470                      475                      480

Glu  Glu  Gln  Ala  Leu  Ala  Gln  Arg  Phe  Glu  Ile  Val  Glu  Glu  Glu  Leu
               485                      490                      495

His  Ser  Ile  Ser  Pro  Asp  Asp  Pro  Pro  Arg  Glu  Ile  Thr  Asp  Glu  Asn
               500                      505                      510

Leu  His  Lys  Ile  Arg  Leu  Val  Arg  Leu  Asn  Asn  Glu  Asn  Gln  Pro  Leu
          515                      520                      525

Val  Val  Leu  Arg  Arg  Leu  Gly  Gly  Asn  Lys  Phe  Ile  Arg  Ile  Glu  Pro
     530                      535                      540

Ile  Thr  Phe  Gln  Glu  Ile  Lys  Gly  Ser  Leu  Val  Ser  Glu  Val  Ile  Asn
545                      550                      555                      560

Pro  Val  Thr  Asn  Lys  Thr  Tyr  Tyr  Val  Ser  Asn  Ala  Lys  Leu  Leu  Gly
               565                      570                      575

Gly  Ser  Pro  Tyr  Ser  Pro  Phe  Arg  Ile  Gly  Leu  Glu  Gly  Val  Trp  Thr
               580                      585                      590

Pro  Glu  Val  Leu  Lys  Ala  Arg  Ala  Ser  Val  Ile  Gly  Lys  Pro  Ile  Gly
          595                      600                      605

Glu  Ser  Tyr  Lys  Arg  Ile  Leu  Ala  Lys  Leu  Gln  Arg  Ile  His  Asn  Ser
     610                      615                      620

Asn  Ile  Leu  Asp  Glu  Arg  Gln  Gly  Leu  Met  His  Glu  Leu  Met  Glu  Leu
625                      630                      635                      640
```

-continued

| | | | | | | | | | | | | | | |
|---|---|---|---|---|---|---|---|---|---|---|---|---|---|---|
|Ile|Asp|Leu|Tyr|Glu 645|Glu|Ser|Gln|Pro 650|Ser|Glu|Arg|Leu|Asn|Ala 655|
|Phe|Arg|Glu|Leu 660|Arg|Thr|Gln|Leu|Glu 665|Lys|Ala|Leu|Tyr 670|Leu|Pro|Glu|
|Met|Glu|Ala 675|Leu|Lys|Lys|Gln|Ile 680|Leu|Gln|Ile|Pro|Asn 685|Lys|Gly|Ser|
|Gly|Ala 690|Ala|Arg|Phe|Leu|Leu 695|Arg|Thr|Ala|Met|Asn 700|Glu|Met|Ala|Gly|
|Lys 705|Thr|Ser|Glu|Ser|Thr 710|Ala|Asp|Leu|Ile|Arg 715|Phe|Ala|Leu|Gln|Asp 720|
|Thr|Val|Ile|Ser|Ala 725|Pro|Phe|Arg|Gly|Tyr 730|Ala|Gly|Ala|Ile|Pro 735|Glu|
|Ala|Ile|Asp|Phe 740|Pro|Val|Lys|Tyr|Val 745|Ile|Glu|Asp|Ile 750|Ser|Val|Phe|
|Asp|Lys|Ile 755|Gln|Thr|Asn|Tyr|Trp 760|Glu|Leu|Pro|Ala|Tyr 765|Glu|Ser|Trp|
|Asn|Glu 770|Gly|Ser|Asn|Ser|Arg 775|Leu|Leu|Pro|Gly|Leu 780|Leu|Arg|Glu|Ser|
|Gln 785|Ser|Lys|Gly|Met|Leu 790|Ser|Lys|Cys|Arg|Ile 795|Ile|Glu|Asn|Ser|Leu 800|
|Tyr|Ile|Gly|His|Ser 805|Tyr|Glu|Glu|Met|Phe 810|Tyr|Ser|Ile|Ser|Pro 815|Tyr|
|Ser|Asn|Gln|Val 820|Gly|Gly|Pro|Tyr|Glu 825|Leu|Tyr|Pro|Phe|Thr 830|Phe|Phe|
|Ser|Met|Leu 835|Gln|Glu|Val|Gln|Gly 840|Asp|Leu|Gly|Phe|Glu 845|Gln|Ala|Phe|
|Ala|Thr 850|Arg|Asn|Phe|Phe|Asn 855|Thr|Leu|Val|Ser|Asp 860|Arg|Leu|Ser|Leu|
|Met 865|Glu|Asn|Thr|Met|Leu 870|Leu|Thr|Glu|Ser|Phe 875|Asp|Tyr|Thr|Pro|Trp 880|
|Asp|Ala|Ile|Tyr|Gly 885|Asp|Ile|Asn|Tyr|Asp 890|Glu|Gln|Phe|Ala|Ala 895|Met|
|Ser|Ile|Asn|Glu 900|Arg|Ile|Glu|Lys|Cys 905|Met|Asn|Thr|Tyr|Arg 910|Gly|Val|
|Ala|Phe|Gln 915|Asn|Ser|Ser|Lys|Ser 920|Ile|Asp|Phe|Phe|Leu 925|Asn|Asn|Leu|
|Thr|Thr 930|Phe|Ile|Asp|Asn|Gly 935|Leu|Thr|Glu|Ile|Ala 940|Ile|Ser|Asp|Leu|
|Pro 945|Tyr|Asp|Ile|Val|Gln 950|Glu|Ile|Ser|Gln 955|Phe|Leu|Gln|Gly|Ser 960|
|Asn|Glu|Trp|Lys|Thr 965|Leu|Asp|Ala|Met|Leu 970|Phe|Asn|Leu|Asp|Lys 975|Gly|
|Asp|Ile|Asn|Gly 980|Ala|Phe|Arg|Lys|Leu 985|Leu|Gln|Ser|Ala|Lys 990|Asp|Asn|
|Asn|Ile|Lys 995|Phe|Arg|Ala|Ile|Gly 1000|His|Ser|Asp|Asn|Ser 1005|Val|Pro|Pro|
|Phe|Asn|Asn 1010|Pro|Tyr|Lys|Ser|Leu 1015|Tyr|Tyr|Lys|Gly|Asn 1020|Ile|Ile|Ala|
|Glu|Ala|Ile 1025|Glu|Lys|Leu|Asp 1030|Arg|Glu|Gly|Gln|Lys 1035|Phe|Val|Val|Phe 1040|
|Ala|Asp|Ser|Ser|Leu 1045|Leu|Asn|Ser|Thr|Pro 1050|Gly|Thr|Gly|Arg|Pro 1055|Met|
|Pro|Gly|Leu|Val 1060|Gln|Tyr|Leu|Lys|Ile 1065|Pro|Ala|Thr|Val|Val 1070|Asp|Ser|
|Asp|Gly|Ala|Trp|Gln|Phe|Leu|Pro|Asp|Val|Ala|Ser|Ser|Arg|Val|Pro|

|     | 1075 |     |     | 1080 |     |     |     |     | 1085 |     |     |     |     |
|-----|------|-----|-----|------|-----|-----|-----|-----|------|-----|-----|-----|-----|
| Ile | Glu  | Val | Thr | Glu  | Leu | Glu | Asn | Trp | Gln  | Val | Leu | Thr | Pro | Pro | Gln |
|     | 1090 |     |     |      1095 |     |     |     |     |  1100 |     |     |     |     |

Gly Lys Ile Leu Gly Leu Lys Gln Phe Lys Leu Thr Ala Gly Phe Pro
1105            1110            1115                    1120

Thr Glu Gln Ser Arg Leu Pro Leu Leu Glu Asn Ser Val Ser Glu Asp
                1125            1130            1135

Leu Arg Glu Glu Leu Met Gln Lys Ile Asp Ala Ile Lys Asn Asp Val
            1140            1145            1150

Lys Met Asn Ser Leu Val Cys Met Glu Ala Gly Ser Cys Asp Ser Val
            1155            1160            1165

Ser Pro Lys Val Ala Ala Arg Leu Lys Asp Met Gly Leu Glu Ala Gly
        1170            1175            1180

Met Gly Ala Ser Ile Thr Trp Trp Arg Arg Glu Gly Gly Met Glu Phe
1185            1190            1195                    1200

Ser His Gln Met His Thr Thr Ala Ser Phe Lys Phe Ala Gly Lys Glu
                1205            1210            1215

Phe Ala Val Asp Ala Ser His Leu Gln Phe Val His Asp Gln Leu Asp
            1220            1225            1230

Thr Thr Ile Leu Ile Leu Pro Val Asp Asp Trp Ala Leu Glu Ile Ala
        1235            1240            1245

Gln Arg Asn Arg Ala Ile Asn Pro Phe Val Glu Tyr Val Ser Lys Thr
    1250            1255            1260

Gly Asn Met Leu Ala Leu Phe Met Pro Pro Leu Phe Thr Lys Pro Arg
1265            1270            1275                    1280

Leu Thr Arg Ala Leu
            1285

We claim:

1. An isolated and purified DNA molecule that encodes a polypeptide product comprising the amino acid sequence of SEQ. ID. NO. 1, lacking amino acid 30 to 150.

2. A DNA molecule of claim 1, further comprising another nucleotide sequence that codes for a another polypeptide, wherein said DNA molecule encodes a fusion protein (i) comprised of said coding region O and said other polypeptide.

3. An expression vector comprising A DNA molecule of claim 1.

4. A microorganism containing the expression vector of claim 3.

5. A microoroganism of claim 4, wherein said microorganism is a bacterium.

6. A bacterium of claim 5, wherein said bacterium is *Escherichia coli*.

7. A method for the production of a of *Pasteurella multocida* toxin polypeptide, comprising the steps of
   (i) transforming a suitable host organism with a DNA molecule according to claim 1;
   (ii) culturing said host organism to express said polypeptide product;
   (iii) separating said polypeptide product from said host organism; and
   (iv) recovering said polypeptide product in a purified form.

8. A method according to claim 7, further comprising after step (iv) a step of subjecting said polypeptide product to a chemical treatment which affects the toxicity of said polypeptide product.

9. A method according to claim 8, wherein the chemical treatment is selected from the group consisting of formaldehyde treatment, glutaraldehyde treatment, and proteolytic enzyme treatment.

* * * * *